(12) United States Patent
Tang et al.

(10) Patent No.: US 9,518,921 B2
(45) Date of Patent: Dec. 13, 2016

(54) SILICA NANOPARTICLES WITH AGGREGATION INDUCED EMISSION CHARACTERISTICS AS FLUORESCENT BIOPROBE FOR INTRACELLULAR IMAGING AND PROTEIN CARRIER

(71) Applicant: THE HONG KONG UNIVERSITY OF SCIENCE AND TECHNOLOGY, Hong Kong (CN)

(72) Inventors: Benzhong Tang, Hong Kong (CN); Wing Yip Lam, Hong Kong (CN); Jianzhao Liu, Hong Kong (CN); Faisal Mahtab, Khyber Pakhtunkhwa (PK); Yang Liu, Hong Kong (CN); Yong Yu, Hong Kong (CN)

(73) Assignee: THE HONG KONG UNIVERSITY OF SCIENCE AND TECHNOLOGY, Clear Water Bay, Kowloon (HK)

( * ) Notice: Subject to any disclaimer, the term of this patent is extended or adjusted under 35 U.S.C. 154(b) by 106 days.

(21) Appl. No.: 13/728,150

(22) Filed: Dec. 27, 2012

(65) Prior Publication Data
US 2013/0210047 A1 Aug. 15, 2013

Related U.S. Application Data

(63) Continuation-in-part of application No. 13/422,374, filed on Mar. 16, 2012.

(60) Provisional application No. 61/581,049, filed on Dec. 28, 2011.

(51) Int. Cl.

| | | |
|---|---|---|
| G01N 21/64 | (2006.01) | |
| G01N 33/543 | (2006.01) | |
| G01N 33/533 | (2006.01) | |
| G01N 33/58 | (2006.01) | |
| C07D 207/448 | (2006.01) | |
| C09B 69/00 | (2006.01) | |
| C07D 207/46 | (2006.01) | |
| C07F 7/08 | (2006.01) | |
| C07F 7/18 | (2006.01) | |
| C09B 23/14 | (2006.01) | |
| B82Y 15/00 | (2011.01) | |

(52) U.S. Cl.
CPC ....... *G01N 21/6428* (2013.01); *C07D 207/448* (2013.01); *C07D 207/46* (2013.01); *C07F 7/0807* (2013.01); *C07F 7/1836* (2013.01); *C09B 23/14* (2013.01); *C09B 23/148* (2013.01); *C09B 69/008* (2013.01); *G01N 33/533* (2013.01); *G01N 33/54326* (2013.01); *G01N 33/54346* (2013.01); *G01N 33/582* (2013.01); *G01N 33/587* (2013.01); *B82Y 15/00* (2013.01); *Y10S 977/773* (2013.01); *Y10S 977/92* (2013.01)

(58) Field of Classification Search
None
See application file for complete search history.

(56) References Cited

U.S. PATENT DOCUMENTS

| | | | |
|---|---|---|---|
| 6,020,206 | A | 2/2000 | Vargeese et al. |
| 7,601,391 | B2 | 10/2009 | Woo et al. |
| 7,883,900 | B2 | 2/2011 | Kang |
| 7,968,735 | B2 | 6/2011 | Renard et al. |
| 2010/0190658 | A1 | 7/2010 | Van Der Eycken et al. |
| 2013/0089889 | A1 | 4/2013 | Tang et al. |
| 2013/0266953 | A1 | 10/2013 | Tang et al. |
| 2014/0255696 | A1 | 9/2014 | Tang et al. |

FOREIGN PATENT DOCUMENTS

| | | |
|---|---|---|
| JP | 61003066 | 1/1986 |
| JP | 61110036 | 5/1986 |
| JP | 2008185364 | 8/2008 |

OTHER PUBLICATIONS

Mahtab et al, Advanced Functional Materials, 2011, 21, pp. 1733-1740.*
"Click Chemistry," Organic Chemistry Portal, <http://www.organic-chemistry.org/namedreactions/click-chemistry.shtm>, Dec. 2, 2010.*
Jorge O. Escobedo, Oleksandr Rusin, Weihua Wang, Onur Alpturk, Kyu Kwang Kim, Xiangyang Xu, Robert M. Strongin, Detection of Biological Thiols, 2006, 139-162.
Phani Kumar Pullela, Taurai Chiku, Michael J. Carvan III, Daniel S. Sem, Fluorescence-based detection of thiols in vitro and in vivo using dithiol probes, Analytical Biochemistry, 2006, 352, 265-273.
Long Yi, Heyang Li, Lu Sun, Liangliang Liu, Cihong Zhang, Zhen Xi, A Highly Sensitive Fluorescence Probe for Fast Thiol-Quantification Assay of Glutathione Reductase, Communications: Fluorescent Probes, Angew. Chem. Int. Ed., 2009, 48, 4034-4037.
Chang-Keun Lim, Sehoon Kim, Ick Chan Kwon, Cheol-Hee Ahn, Soo Young Park, Dye-Condensed Biopolymeric Hybrids: Chromophoric Aggregation and Self-Assembly toward Fluorescent Bionanoparticles for Near Infrared Bioimaging, Chem. Mater., 2009, 21, 5819-5825.

* cited by examiner

*Primary Examiner* — Alicia L Otton
(74) *Attorney, Agent, or Firm* — Nath, Goldberg & Meyer; Joshua B. Goldberg

(57) ABSTRACT

Provided herein are magnetic silica fluorescent nanoparticles and fluorescent silica nanoparticles comprising an aggregation induced emission luminogen and magnetite nanoparticles and use of the same as a fluorescent bioprobe for intracellular imaging and a protein carrier. Also provided are processes for preparing and fabricating the same.

30 Claims, 40 Drawing Sheets

SILICA NANOPARTICLES WITH AGGREGATION INDUCED EMISSION CHARACTERISTICS AS FLUORESCENT BIOPROBE FOR INTRACELLULAR IMAGING AND PROTEIN CARRIER

RELATED APPLICATIONS

The present patent application is a continuation in part of prior patent application Ser. No. 13/422,374, filed Mar. 16, 2012, which is incorporated by reference herein in its entirety. Furthermore, the present patent application also claims priority to provisional Patent Application No. 61/581,049, filed Dec. 28, 2011, which was filed by the inventors hereof and is incorporated by reference herein in its entirety.

TECHNICAL FIELD

The present subject matter relates to a series of conjugated luminogen compounds exhibiting aggregation induced emission (AIE) properties and the use of the same for biosensing target molecules. In particular, the present subject matter relates to conjugated luminogen compounds comprising an AIE luminogen and magnetite nanoparticles and the use of the same as fluorescent probes for bioimaging and protein carriers.

BACKGROUND

Fluorescent nanoparticles have been found useful as visualization tools for biological sensing, probing, imaging, and monitoring. The development of fluorescent probes for biomolecular detection has emerged as an exciting area of research because of its importance in bioscience and biotechnological applications, as well as its impact on public health. The fluorescent assay process offers a number of advantages over other analytical techniques, such as rapid response, high sensitivity, low background noise, and wide dynamic working range. Thanks to the enthusiastic effort of scientists devoted to this area of research, a large variety of fluorescent bioprobes have been developed. However, many of the bioprobes work in a "turn off" mode. For example, the emission of a fluorophore is switched "off" when it interacts with a quenching species in a biological system through a mechanism of fluorescence resonance energy transfer.

Typical materials used as biosensors include natural polymers, inorganic nanoparticles, and organic dyes. Green fluorescent protein (GFP), for example, has been used as a reporter of expression for morphological differentiation. The biosensing process, however, requires complicated and time-consuming transfection procedures, which can lead to unexpected morphologies and undesired abnormality in the target cells. Inorganic nanoparticles, such as semiconductor quantum dots (QDs), are highly luminescent and resistant to photobleaching but limited in variety and inherently toxic to living cells because QDs are commonly made of heavy metals and chalcogens (e.g., CdS, CdSe, CdTe, PbS, and PbSe).

Among the nanoparticles, QDs have attracted a lot of attention, particularly in the area of cellular marking and imaging. QDs enjoy such advantages as size-tunable emission color, long luminescence lifetime, and resistance to photobleaching. However, QDs are limited in variety, difficult to access, chemically unstable in harsh environments, difficult to dispose of, and highly cytotoxic to living cells because they are commonly made of heavy metals and chalcogens (e.g., CdS, CdSe, CdTe, PbS, and PbSe). These limitations present challenges to scientists from academic to industrial sectors.

Organic dyes are rich in variety and have been widely used as readily processable light-emitting materials, particularly in the area of organic optoelectronics. Due to their poor miscibility with water, organic dyes are prone to aggregate in aqueous media, which normally weakens their light emissions. This effect is commonly known as aggregation-caused quenching (ACQ).

Alternatively, organic fluorophores, such as fluorescein and rhodamine, have been used. Thanks to the elaborate efforts of various scientists, a wide variety of luminogenic materials covering a wide range of absorption and emission wavelengths have been prepared and specialized for particular applications. However, when these fluorophores are worked into acidic or basic media with enzymes and ions, their emissions are quenched through multiple nonradiative pathways.

For sensitive detection, trace analysis, diagnostic assays, and real-time monitoring, fluorescent bioprobes must emit intense visible light upon photoexcitation. However, light emissions from most fluorophores are rather weak. This aggregation-caused quenching (ACQ) is due to emission quenching caused by the aggregation of fluorophores in the solid state. When dispersed in aqueous media or bound to biomolecules, fluorophore molecules are inclined to aggregate, which usually quenches their fluorescence, and thus, greatly limits their effectiveness as bioprobes. The ACQ effect also makes it difficult to assay low-abundance molecular species in biological systems because the fluorescence signals from minimal amounts of fluorophores matching the bioanalyte levels may be too weak to be determined accurately. In addition, at high fluorophore concentrations, the emissions are further weakened, rather than enhanced, due to the ACQ effect.

Accordingly, there is a great need for the development of fluorescent bioprobes for bioimaging that are resistant to the ACQ effect. Furthermore, the fluorescent bioprobes must have high biological compatibility, strong photobleaching resistance, efficient light emission, high selectivity and sensitivity, and must be nontoxic to living cells.

SUMMARY

Accordingly, there is a great need for the development of fluorescent bioprobes for bioimaging that are resistant to the ACQ effect. Furthermore, the fluorescent bioprobes must have high biological compatibility, strong photobleaching resistance, efficient light emission, high selectivity and sensitivity, and must be nontoxic to living cells.

The present subject matter relates to fluorescent bioprobes comprising nanoaggregates of organic luminogens that exhibit aggregation-induced emission (AIE), rather than ACQ when aggregated in the solid state. This unique AIE effect has been utilized to develop new bioprobes of "turn on" type, which enjoy much higher sensitivity than their "turn off" counterparts.

In contrast to the conventional GFP- and QD-based biosensors, the AIE fluorescent bioprobes described herein are easy to use and nontoxic to living cells. The instant bioprobes are also superior to conventional organic dye systems in that they are ACQ-free, electrically neutral, biocompatible, and usable at high concentrations.

Specifically, the present subject matter relates to a series of luminogen molecules, such as tetraphenylethylene (TPE) and hexaphenylsilole, which are nonemissive in solution, but are induced to emit efficiently when aggregated. Due to their AIE properties, the fluorescence quantum yields of the luminogens are dramatically increased, changing them from faint fluorophores to strong emitters.

Furthermore, encapsulation of luminogens, by physical methods or covalent bonds to the host materials, protects them against chemically reactive species, such as oxygen. Therefore, the present subject matter is related to the encapsulation of AIE luminogens by silica nanoparticles. Furthermore, the present subject matter is related to magnetic fluorescent and/or fluorescent silica nanoparticles (MFSNPs and FSNPs) with aggregation induced emission properties and practical applications as fluorescent probes for bioimaging and protein carriers. Magnetic nanoparticles and AIE luminogens are prepared and integrated into the silica network through new synthetic approaches.

Specifically, the present subject matter is directed to a fluorescent bioprobe for intracellular imaging comprising an aggregation induced emission luminogen and magnetite nanoparticles; wherein the luminogen has a backbone structure selected from the group consisting of:

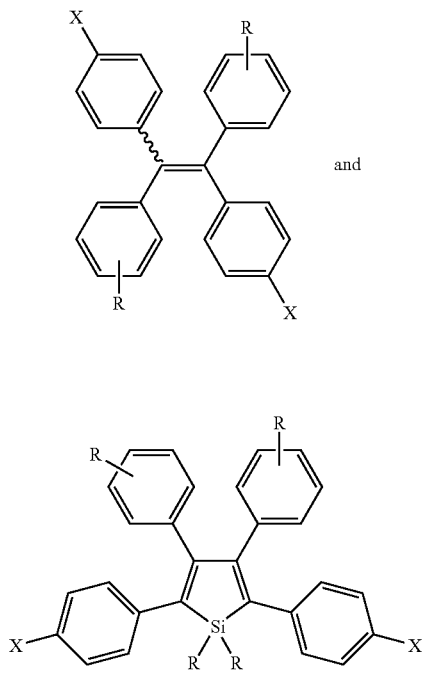

wherein R is selected from the group consisting of H, alkyl, unsaturated alkyl, aryl, vinyl, acetyl, heteteroalkyl, cycloalkyl, heterocycloalkyl, and heteroaryl; X is selected from the group consisting of $(CH_2)_n$, $C_6H_5$, $(Ph)_n$, $O(CH_2)_n$, $NH(CH_2)_n$, $N[(CH_2)_n]_2$, and $(OCH_2CH_2)_n$; and n=0 to 20; wherein X is capable of conjugating with a siloxane; and wherein the fluorescent bioprobe is selected from the group consisting of magnetic fluorescent silica nanoparticles (MFSNPs) and fluorescent silica nanoparticles (FSNP).

In addition, the present subject matter is directed to processes for preparing the MFSNPs and FSNPs. The present subject matter is also related to processes for the fabrication of FSNPs comprising surface grafting of the AIE luminogen onto the magnetite nanoparticles, and processes for surface functionalization of FSNPs.

BRIEF DESCRIPTION OF THE DRAWINGS

Various embodiments will be described in detail with reference to the accompanying drawings.

excitation wavelength (nm): 353 (FSNP-19 and TPE-containing diynes (21)) and (B) 370 (FSNP-20 and silole-containing diynes (24)).

Figure 25:
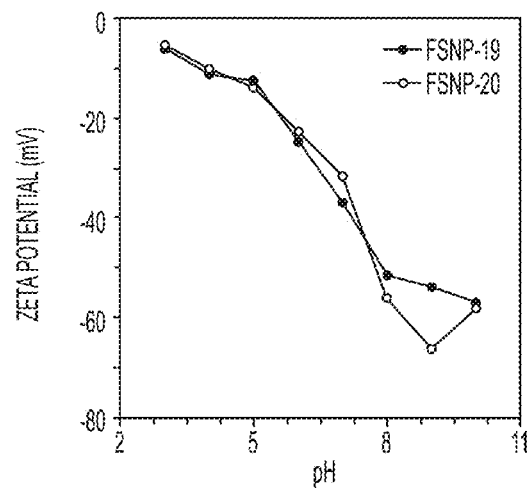

FIG. 25 shows the zeta potentials of FSNP-19 and FSNP-20 in aqueous media

Figure 26:
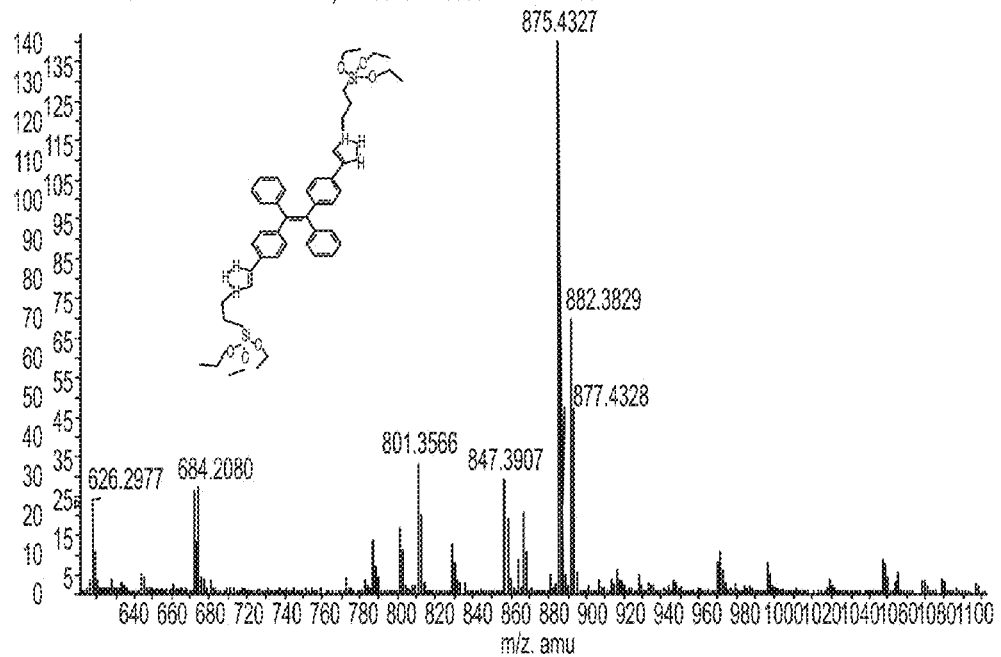

FIG. 26 shows the HRMS spectrum of 1,2-Bis(4-{1-[2-(triethoxysilyl)ethyl]-4-triazolyl}phenyl)-1,2-diphenylethene (32).

Figure 27:
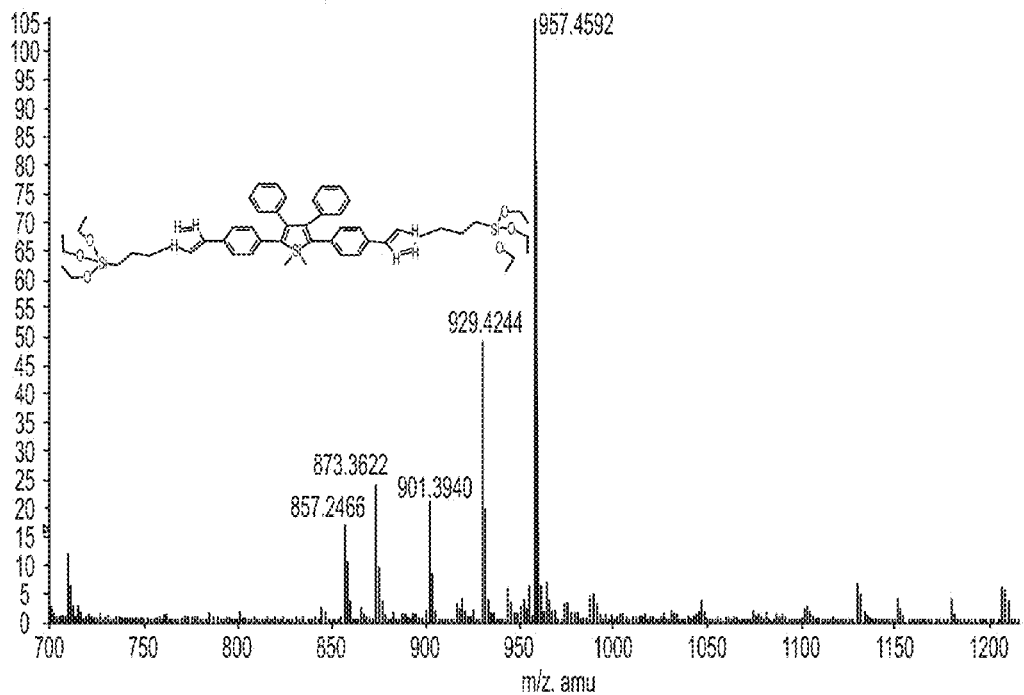

FIG. 27 displays the HRMS spectrum of 2,5-Bis(4-{1-[2-(triethoxysilyl)ethyl]-4-triazolyl}phenyl)-3,4-diphenyl-1,1-dimethylsilole (33).

Figure 28:
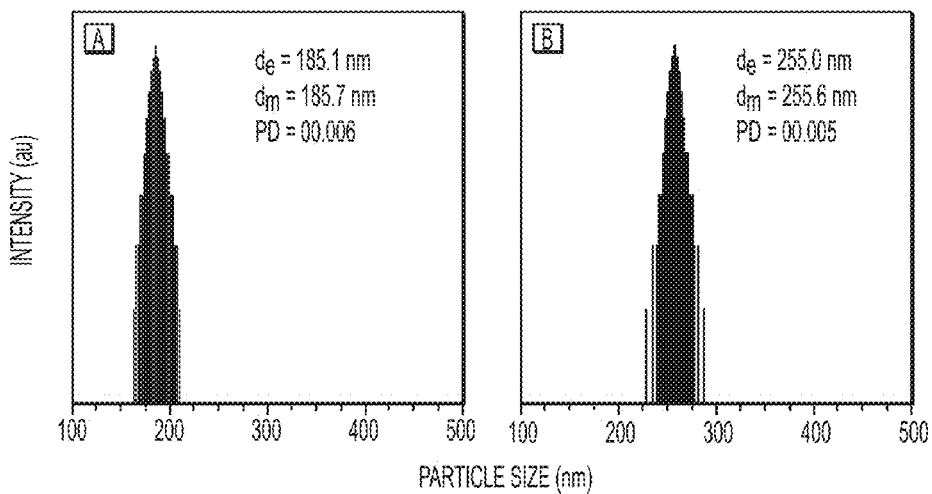

FIG. 28 shows the particle size distributions of FSNP-26 and FSNP-28. Abbreviation: $d_e$=effective diameter, $d_m$=mean diameter, PD=polydispersity.

Figure 29:
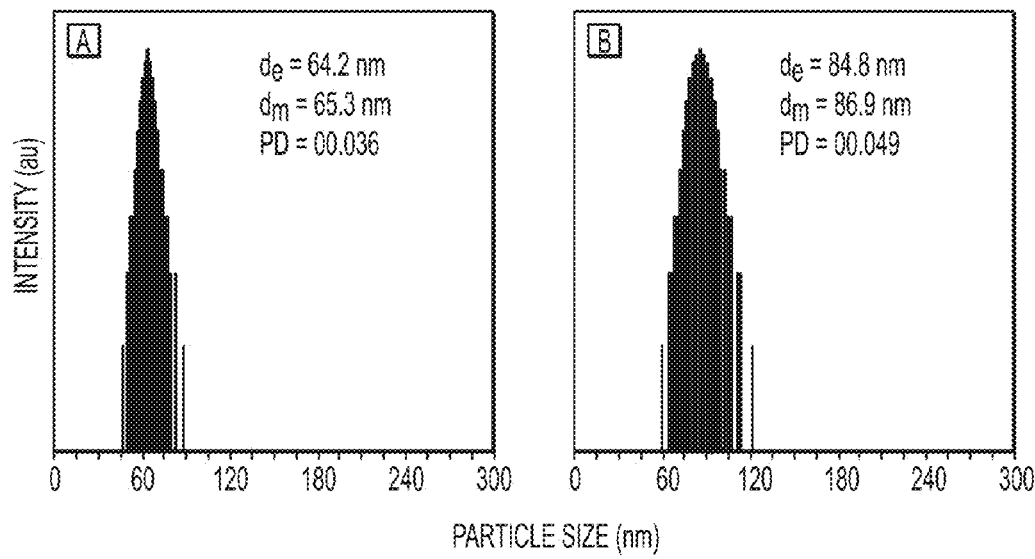

FIG. 29 shows the particle size distributions of FSNP-27 and FSNP-29. Abbreviation: $d_e$=effective diameter, $d_m$=mean diameter, PD=polydispersity.

Figure 30:
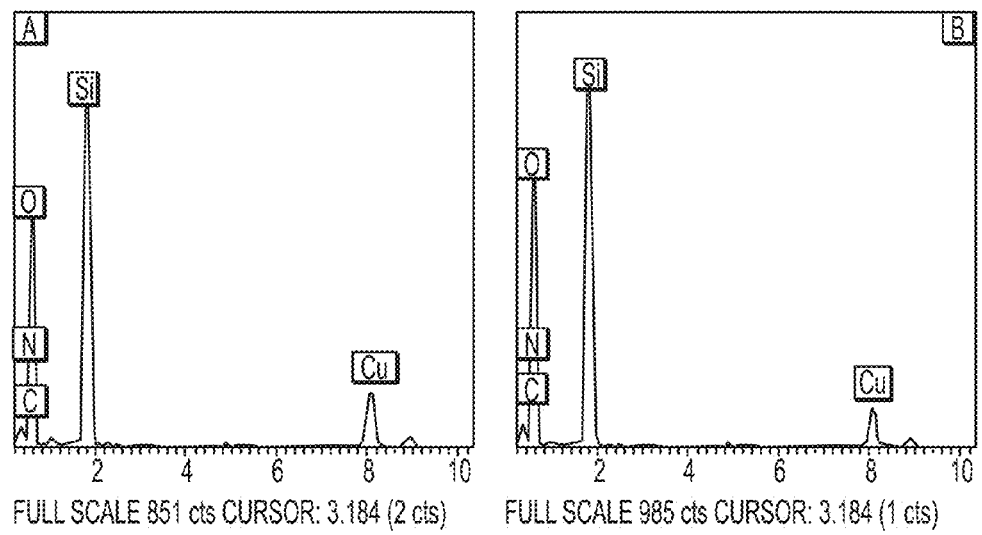

FIG. 30 shows the EDX spectra of FSNP-26 and FSNP-28.

Figure 31:
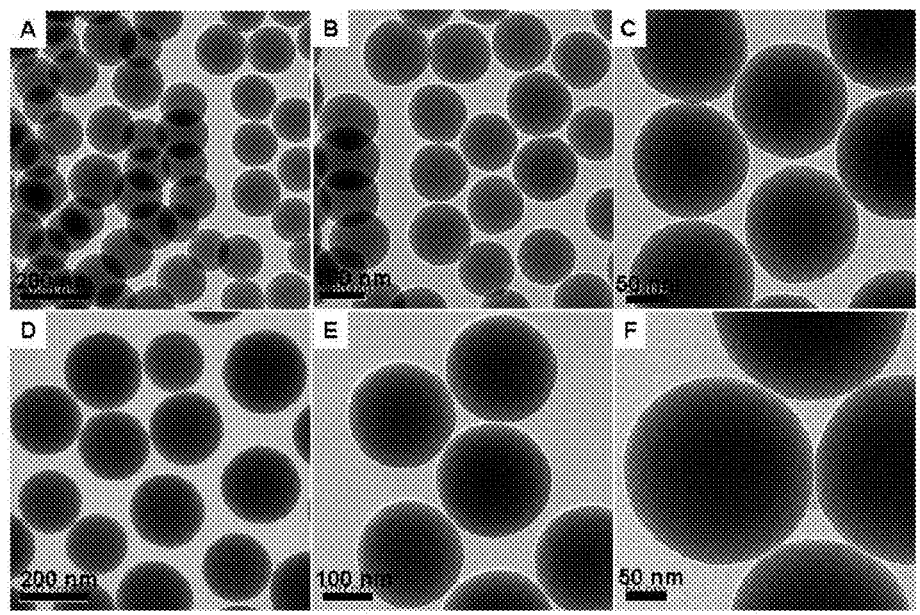

FIG. 31 shows the TEM micrographs of FSNP-26 and FSNP-28 at different magnifications with particle sizes of ~143.37±10.52 and 217.26±20.39 nm, respectively.

Figure 32:
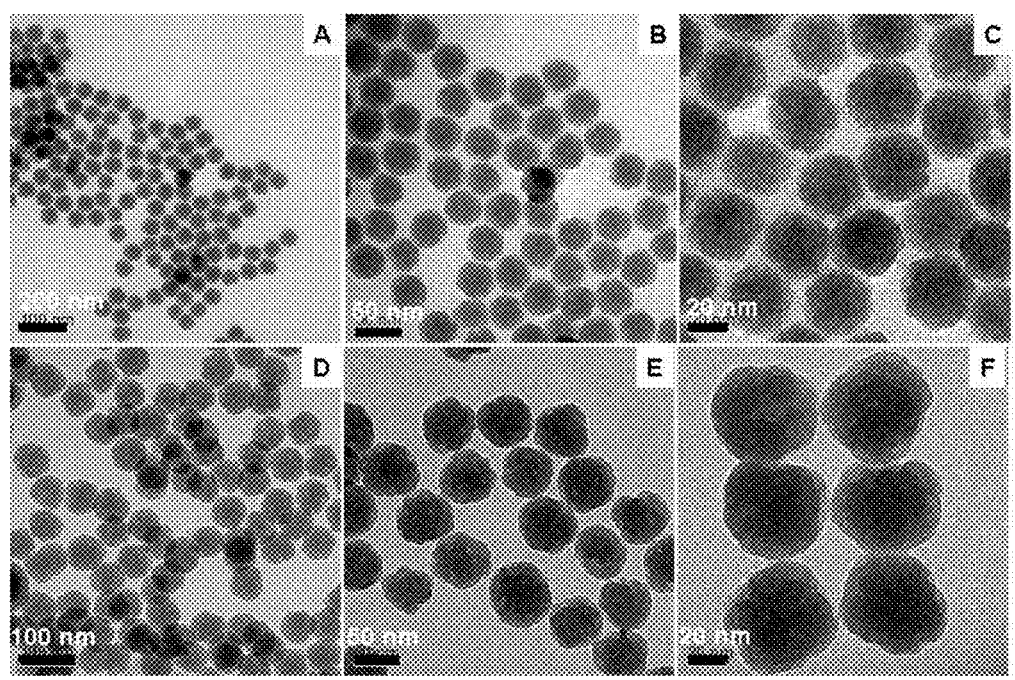

FIG. 32 shows the TEM micrographs of FSNP-27 and FSNP-29 at different magnifications with particle sizes of ~37.68±2.66 and 59.82±4.046 nm, respectively.

Figure 33:
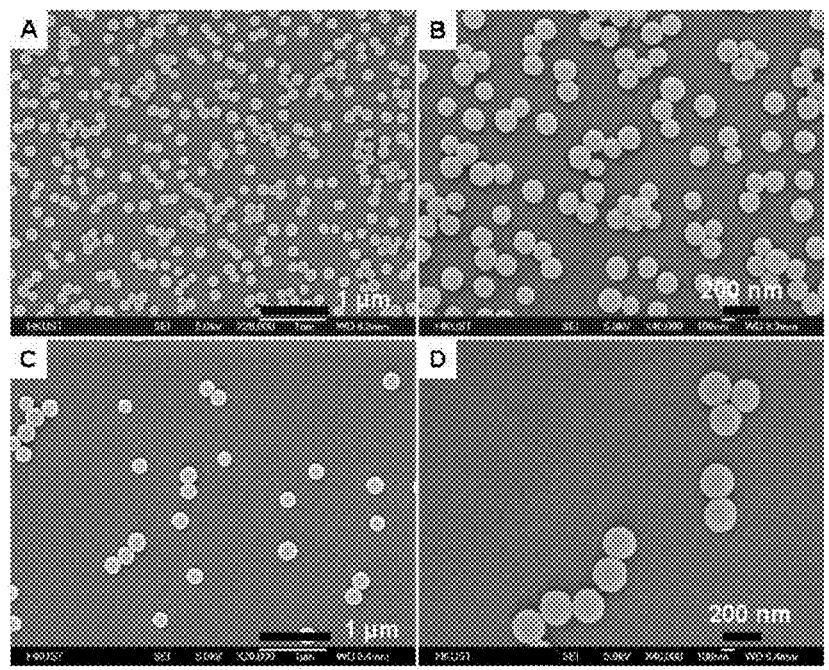

FIG. 33 shows the SEM micrographs of FSNP-26 and FSNP-28 at different magnifications.

Figure 34:
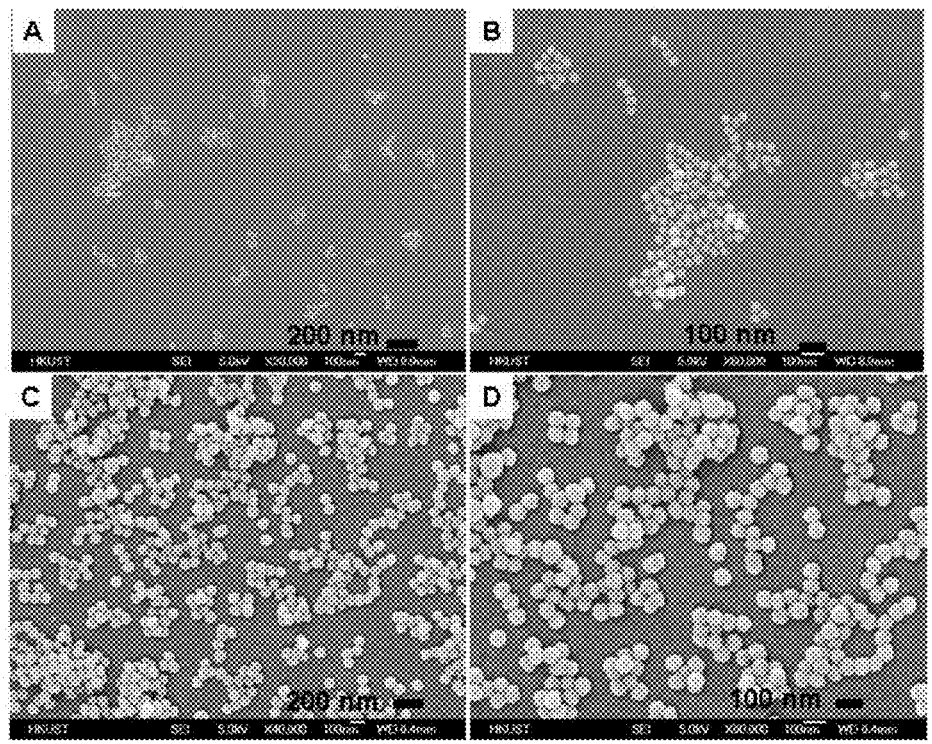

FIG. 34 shows the SEM micrographs of FSNP-27 and FSNP-29 at different magnifications.

Figure 35:
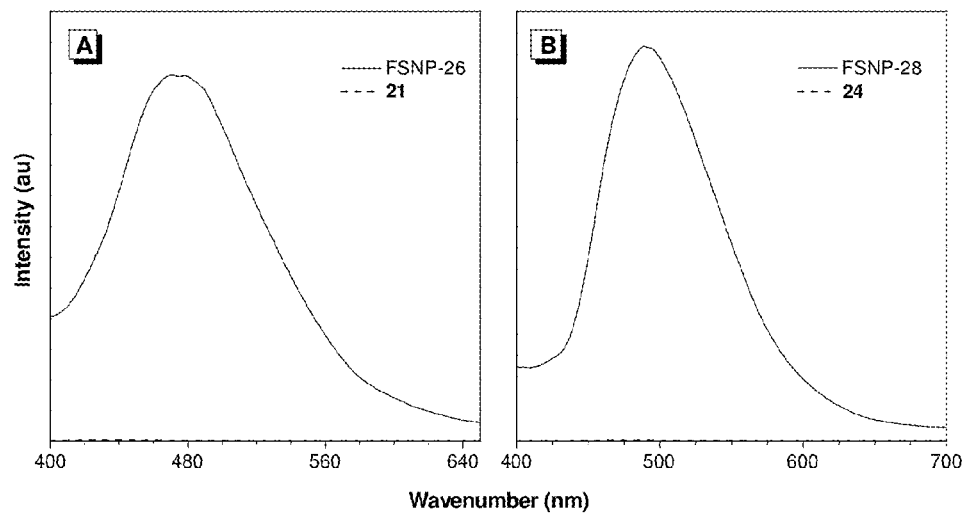

FIG. 35 shows the fluorescence spectra of ethanol solutions of FSNP-26, TPE-containing diynes (21), FSNP-28, and silole-containing diynes (24). Concentration: 200 µg/mL; excitation wavelength (nm): 353 (FSNP-26 and TPE-containing diynes (21)) and 370 (FSNP-28 and silole-containing diynes (24)).

Figure 36:
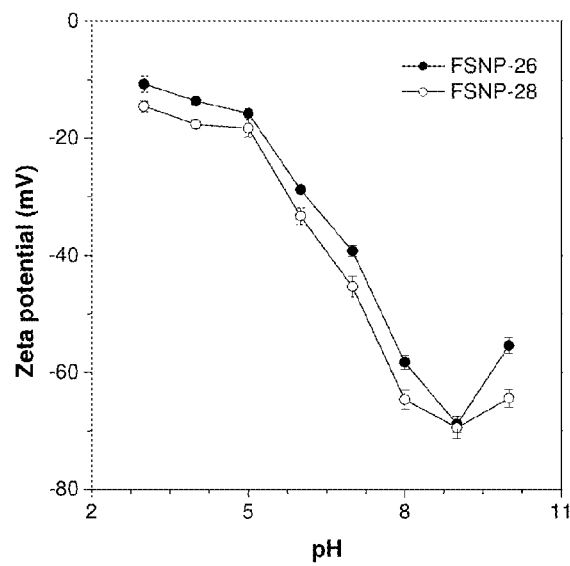

FIG. 36 shows the zeta potentials of FSNP-26 and FSNP-28 in aqueous media.

Figure 37:
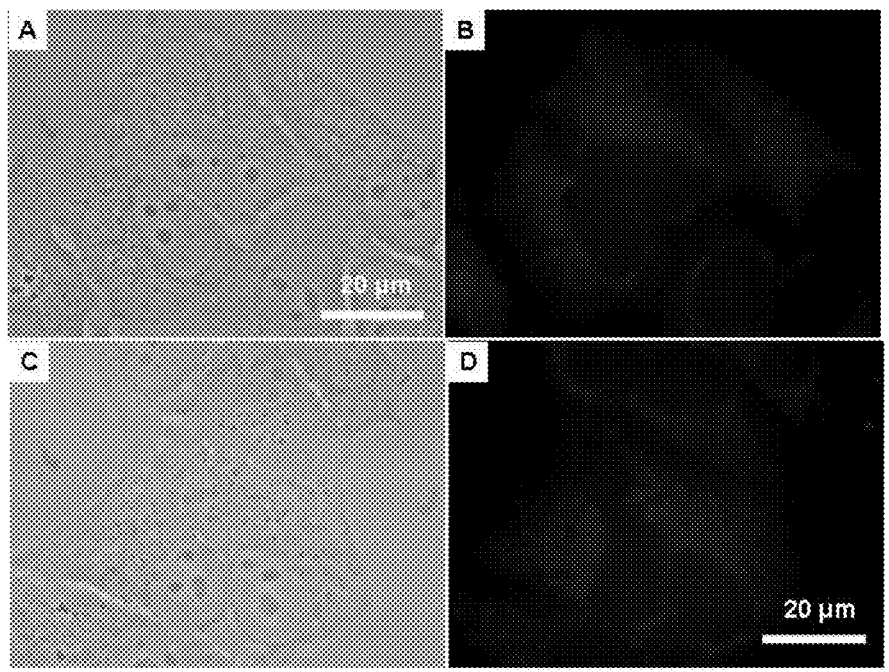

FIG. 37 shows the bright-field and fluorescent images of HeLa cells labelled with FSNP-26 and FSNP-27.

Figure 38:
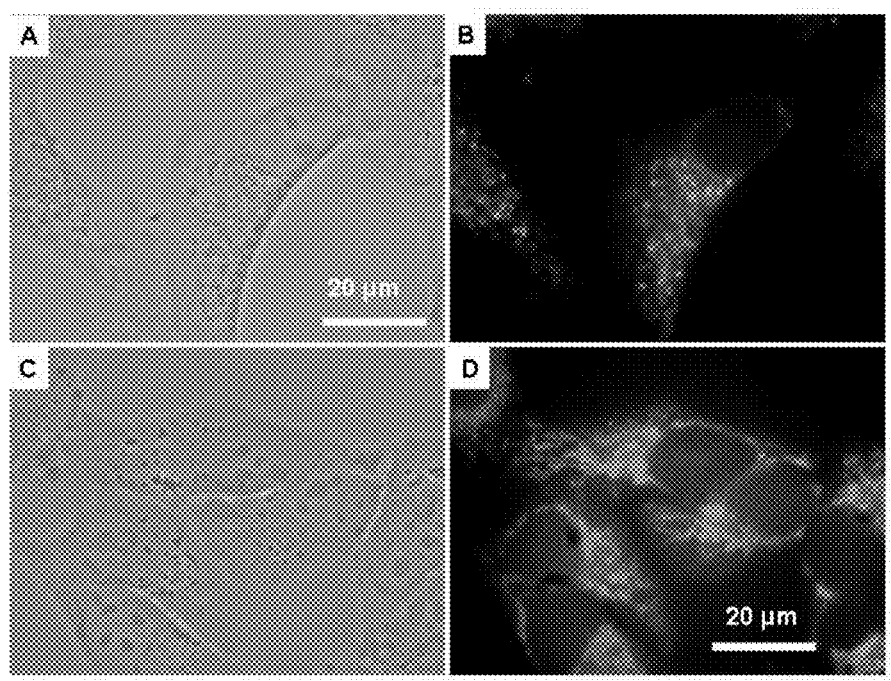

FIG. 38 shows the bright-field and fluorescent images of HeLa cells labelled with FSNP-28 and FSNP-29.

Figure 39:
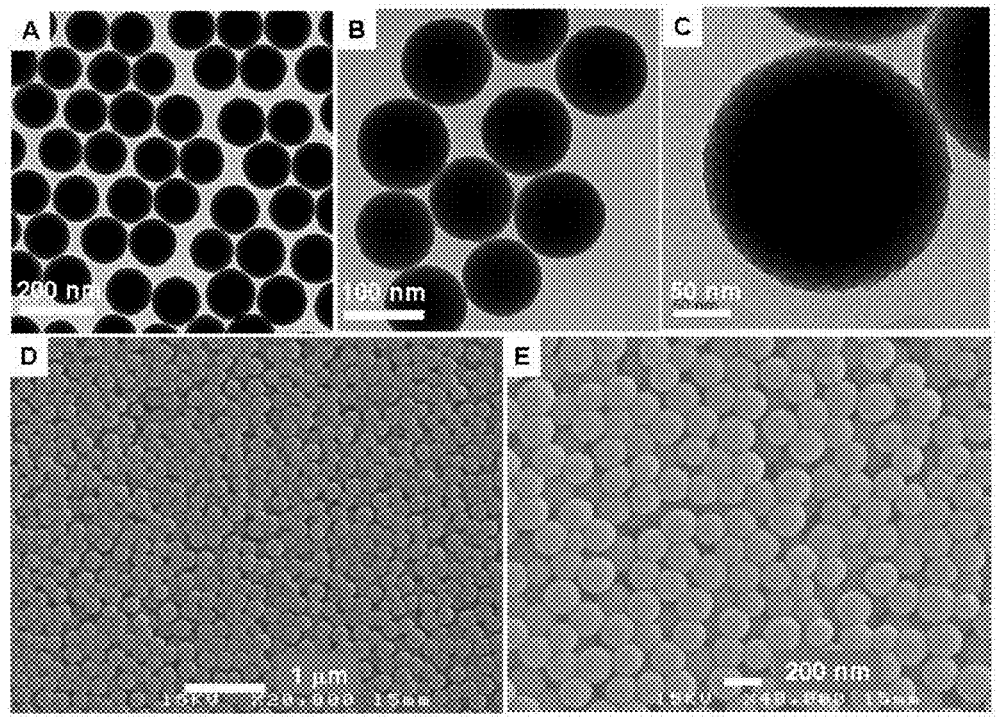

FIG. 39 shows the TEM and SEM micrographs of FSNP-34 at different magnifications.

Figure 40:
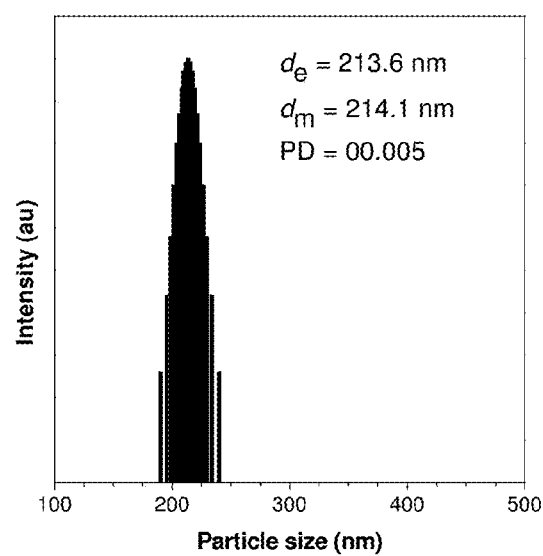

FIG. 40 shows the particle size distributions of FSNP-34. Abbreviation: $d_e$=effective diameter, $d_m$=mean diameter, PD=polydispersity.

Figure 41:
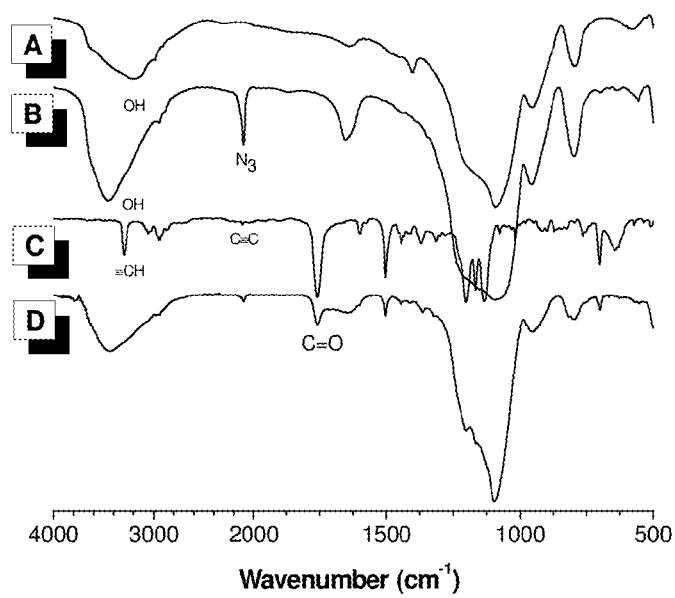

FIG. 41 shows the IR spectra of SNP-Br, FSNP-$N_3$, TPE-containing diynes (38), and FSNP-34.

Figure 42:
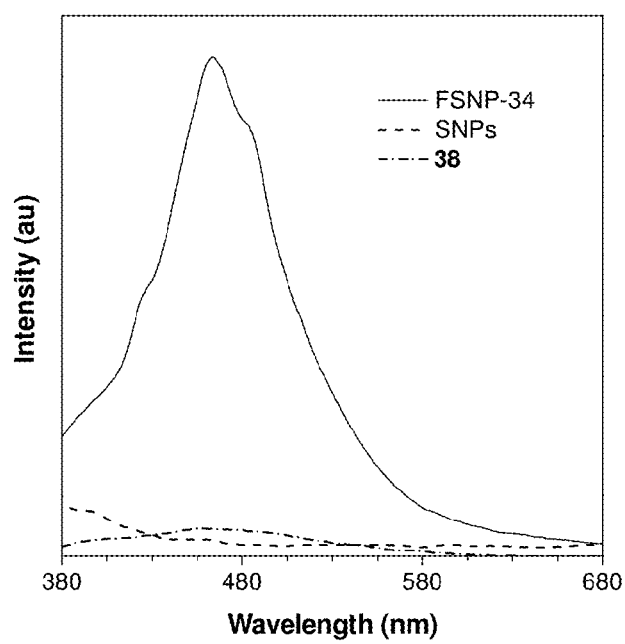

FIG. 42 shows the fluorescence spectra of FSNP-34, SNPs, and TPE-containing diynes (38) in ethanol. Concentration: 200 µg/mL; excitation wavelength: 353 nm.

Figure 43:
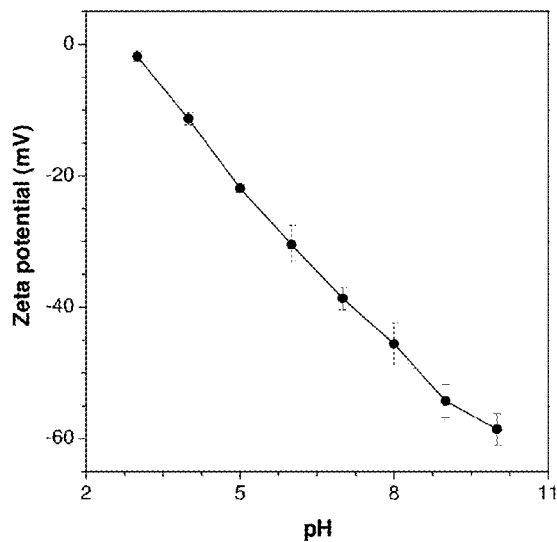

FIG. 43 shows the zeta potentials of FSNP-34 in aqueous medium at different pH.

Figure 44:
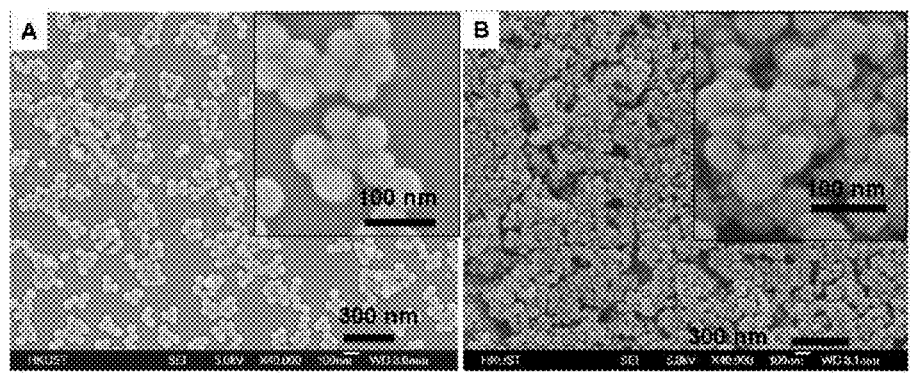

FIG. 44 shows the SEM micrographs of FSNP-39-$N_3$ and FSNP-39-Glu.

Figure 45:
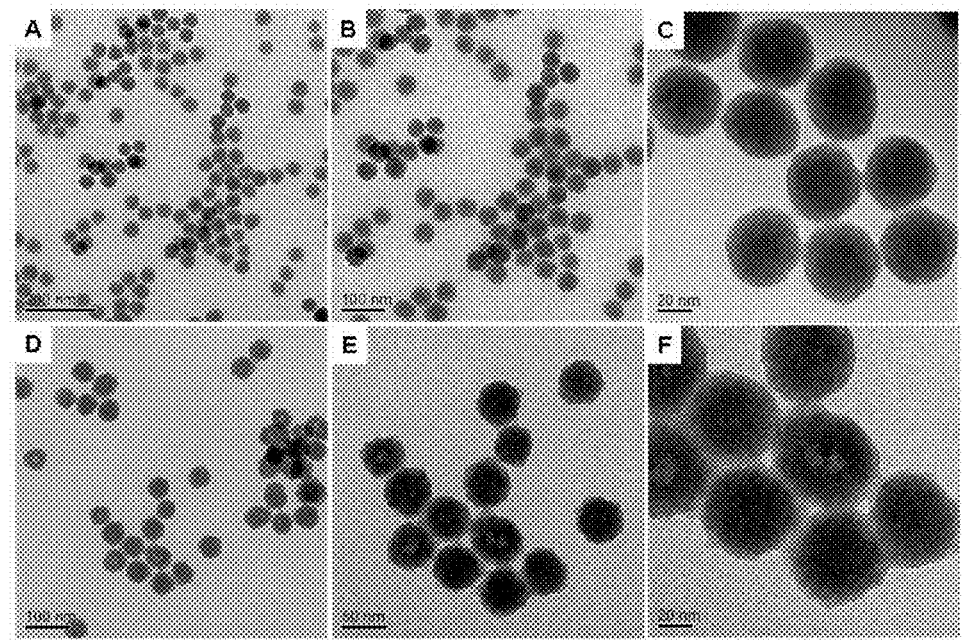

FIG. 45 shows the TEM micrographs of FSNP-39-$N_3$ and FSNP-39-Glu at different magnifications with particle sizes of ~42.20±1.55 and 50.93±4.41 nm, respectively.

Figure 46:
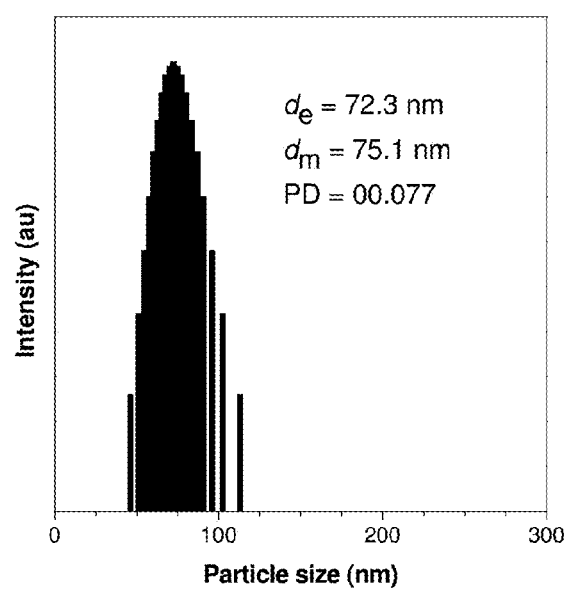

FIG. 46 shows the particle size distributions of FSNP-39-Glu. Abbreviation: $d_e$=effective diameter, $d_m$=mean diameter, PD=polydispersity.

Figure 47:
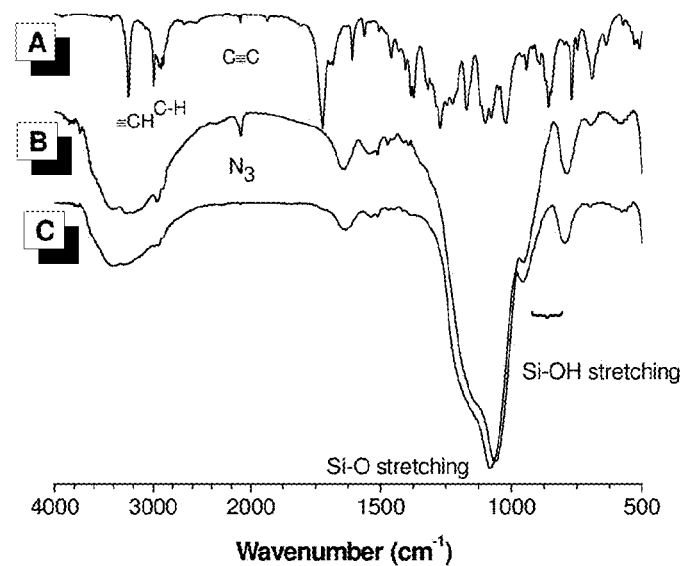

FIG. 47 shows the IR spectra of sugar-containing phenylacetylene (40), FSNP-39-$N_3$, and FSNP-39-Glu.

Figure 48:
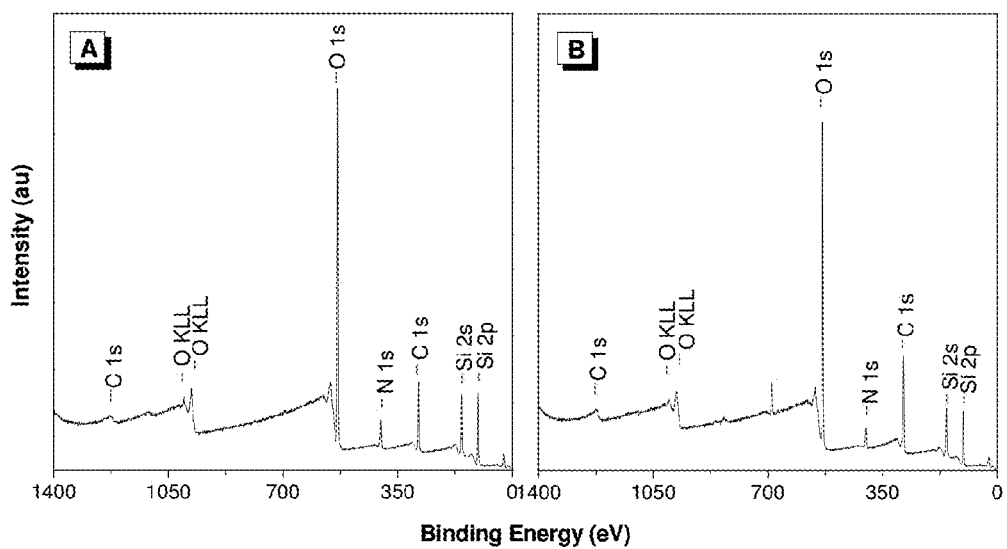

FIG. 48 shows the XPS spectra of FSNP-39-$N_3$ and FSNP-39-Glu.

Figure 49:
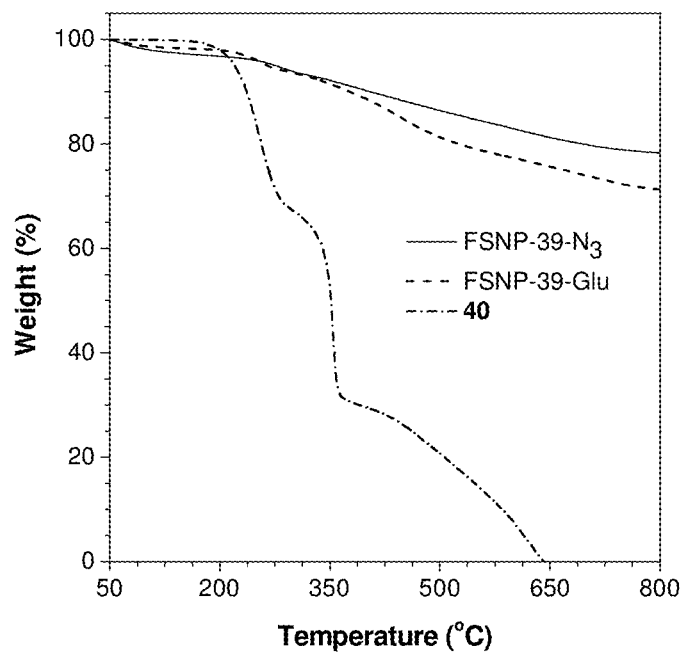

FIG. 49 shows the TGA curves of FSNP-39-$N_3$, FSNP-39-Glu, and sugar-containing phenylacetylene (40).

Figure 50:
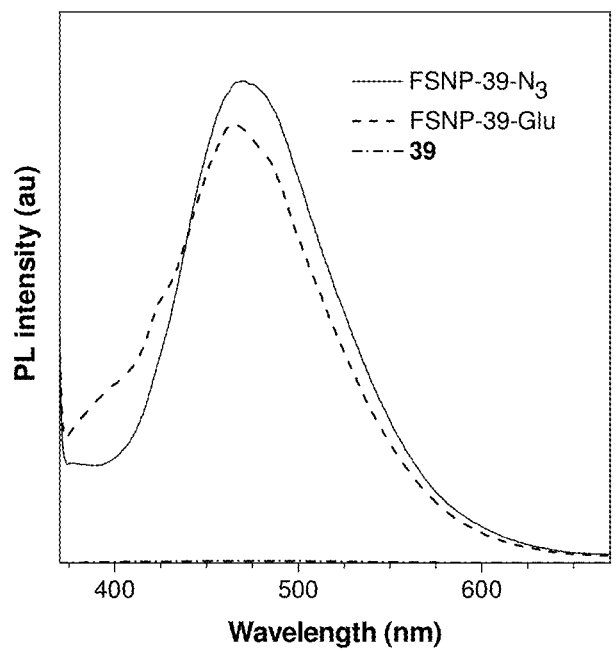

FIG. 50 shows the photoluminescence spectra of FSNP-39-$N_3$, FSNP-39-Glu, and 39 in ethanol. Concentration: 200 µg/mL; excitation wavelength: 353 nm.

Figure 51:
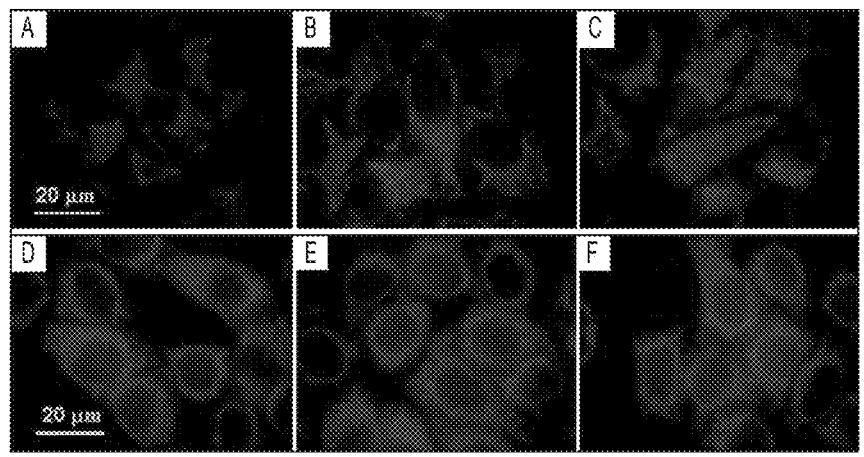

FIG. 51 shows the fluorescent images of HeLa cells and Hepatocytes incubated with FSNP-39-Glu for 3, 5, and 12 h.

Figure 52:
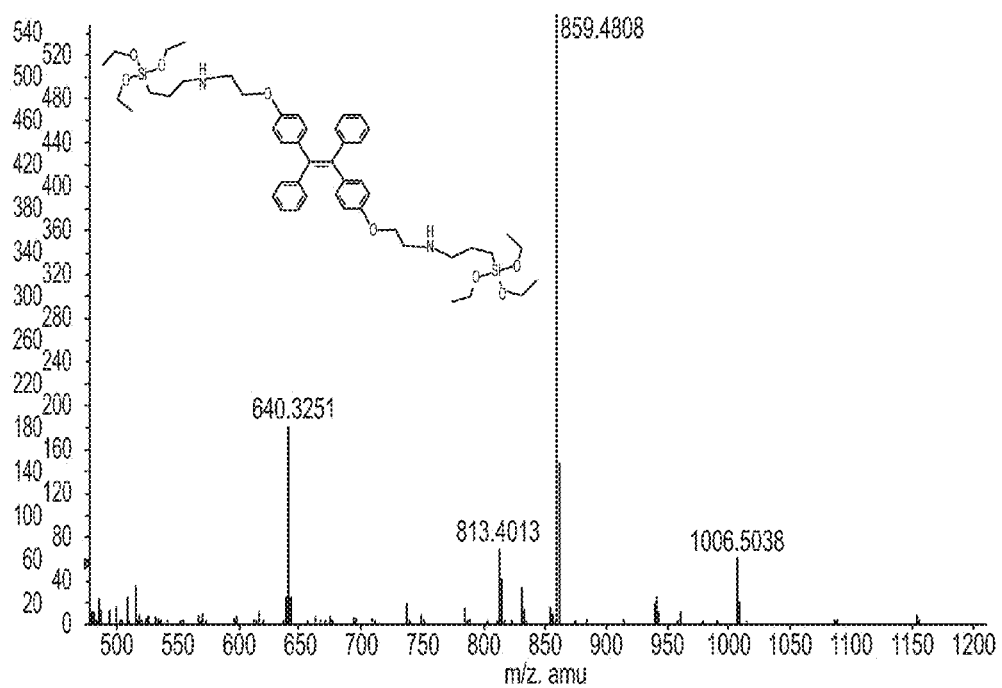

FIG. 52 shows the MS spectrum of TPE-containing siloxane (41).

Figure 53:
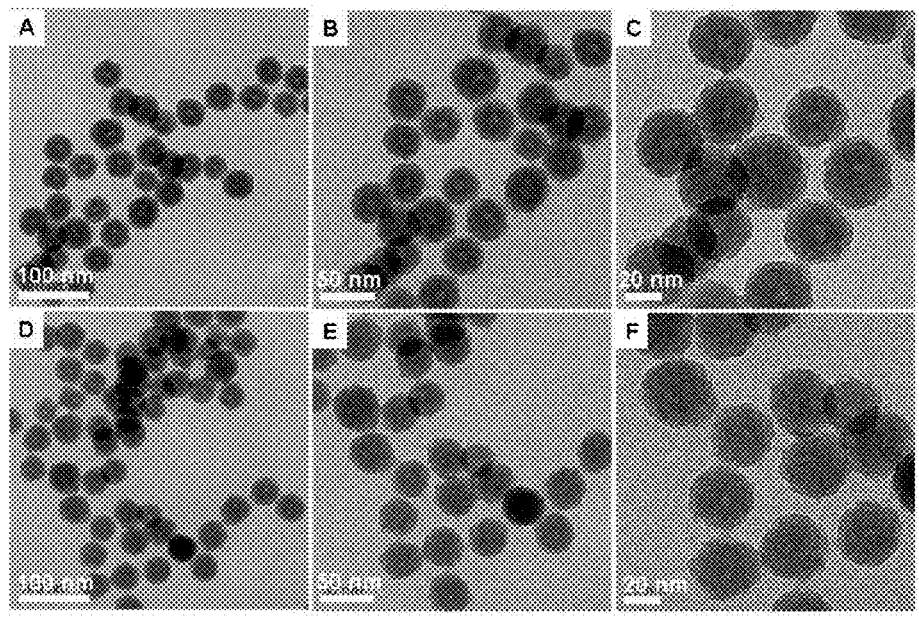

FIG. 53 shows the TEM images of FSNP-41-Gal with particle size of 46.27±3.73 nm and FSNP-7-Gal with particle size of 46.66±4.04 nm at different magnifications.

Figure 54:
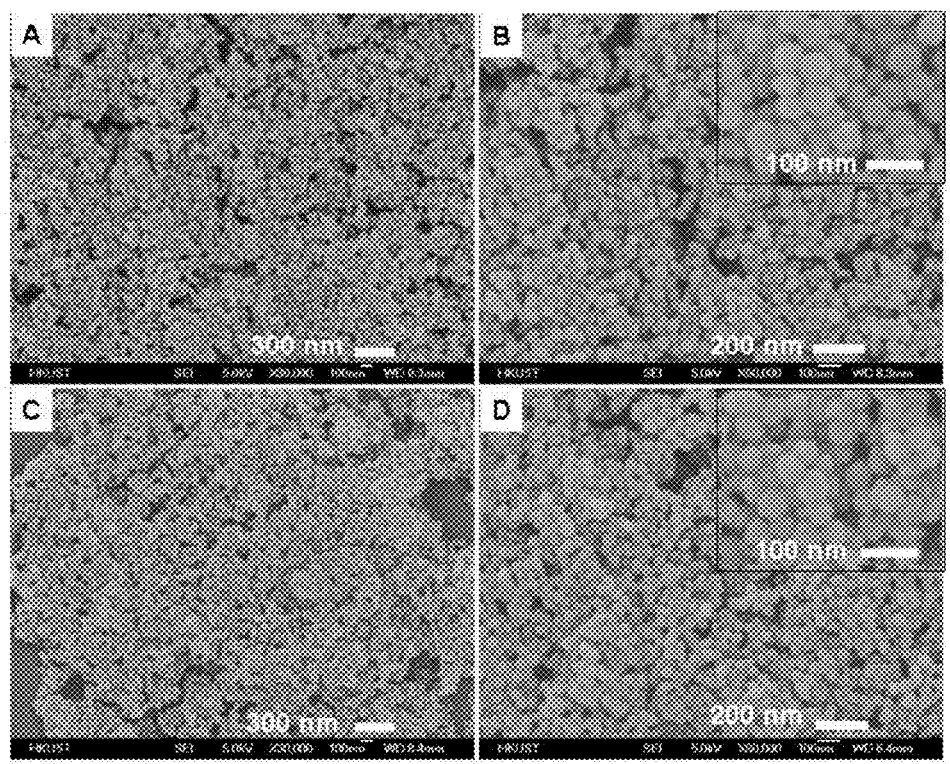

FIG. 54 shows the SEM images of FSNP-41-Gal and FSNP-7-Gal at different magnifications.

Figure 55:
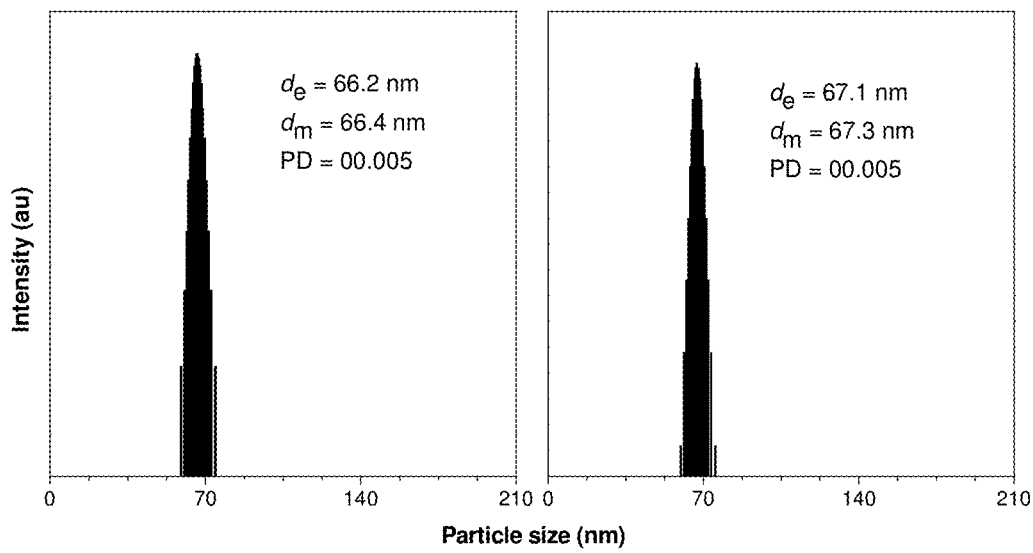

FIG. 55 shows the particle size distributions of FSNP-41-Gal and FSNP-7-Gal. Abbreviation: $d_e$=effective diameter, $d_m$=mean diameter, PD=polydispersity.

Figure 56:
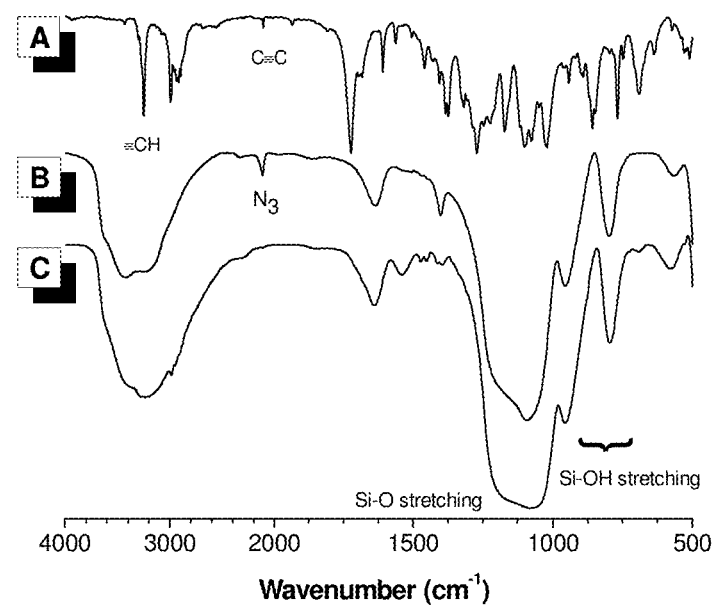

FIG. 56 shows the IR spectra of sugar-bearing phenylacetylene (42), FSNP-41-$N_3$ and FSNP-41-Gal.

Figure 57:
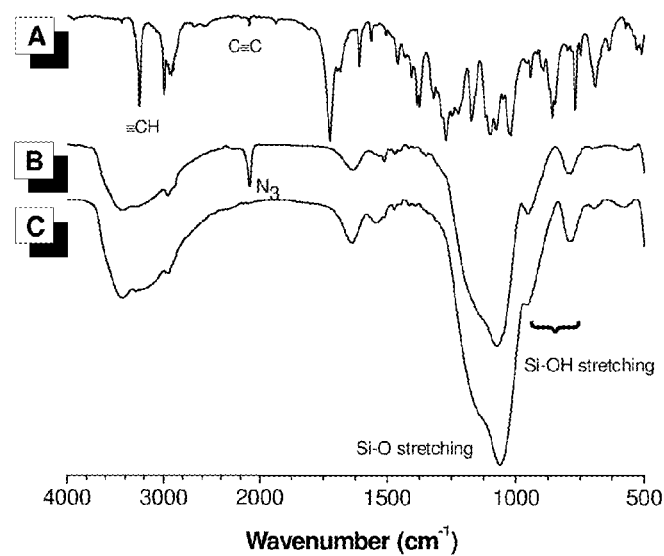

FIG. 57 shows the IR spectra of sugar-bearing phenylacetylene (42), FSNP-7-$N_3$ and FSNP-7-Gal.

Figure 58:
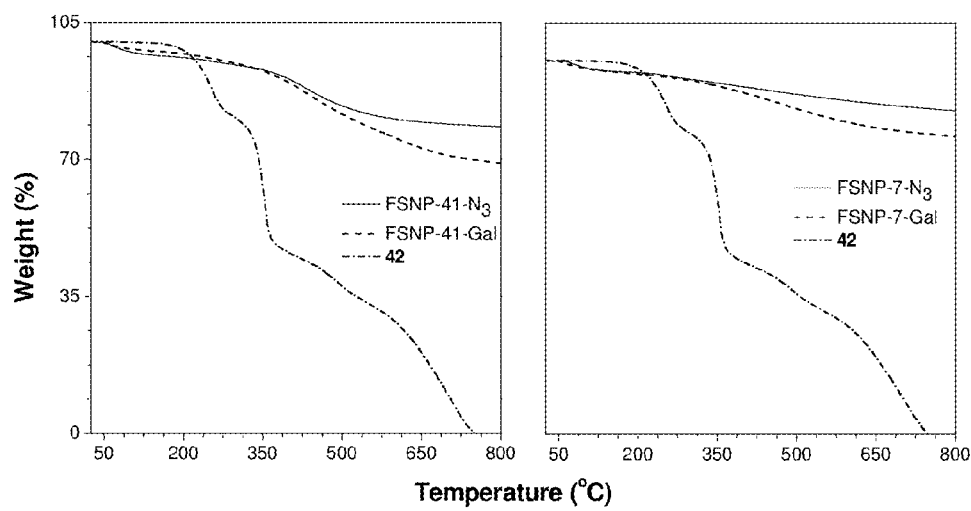

FIG. 58 shows the TGA thermograms of 4-hydroxybenzophenone (42), FSNP-41-$N_3$, FSNP-41-Gal, 42, FSNP-7-$N_3$ and FSNP-7-Gal recorded under nitrogen at a heating rate of 10° C./min.

Figure 59:
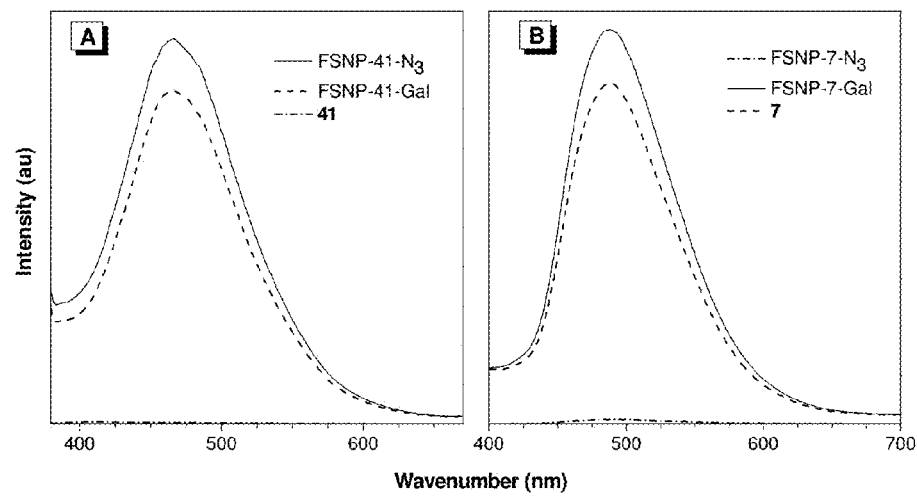

FIG. 59 shows the PL spectra of FSNP-41-$N_3$, FSNP-41-Gal, TPE-containing siloxane (41), FSNP-7-$N_3$, FSNP-7-Gal and silole-functionalized siloxane (7) in ethanol solutions. Concentration: 200 µg/mL; excitation wavelength (nm): 353 (FSNP-41-$N_3$, FSNP-41-Gal and TPE-containing siloxane (41)) and 370 (FSNP-7-$N_3$, FSNP-7-Gal and silole-functionalized siloxane (7)).

Figure 60:
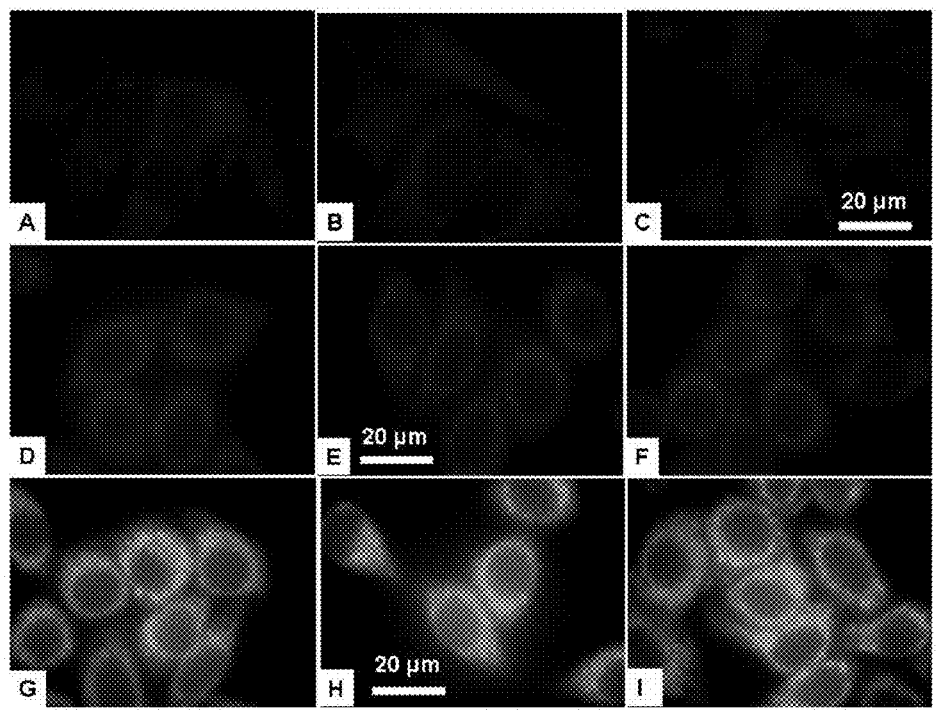

FIG. 60 shows the fluorescent images of HeLa cells and hepatocytes incubated with FSNP-41-Gal and FSNP-7-Gal for 2, 4 and 8 h.

Figure 61:
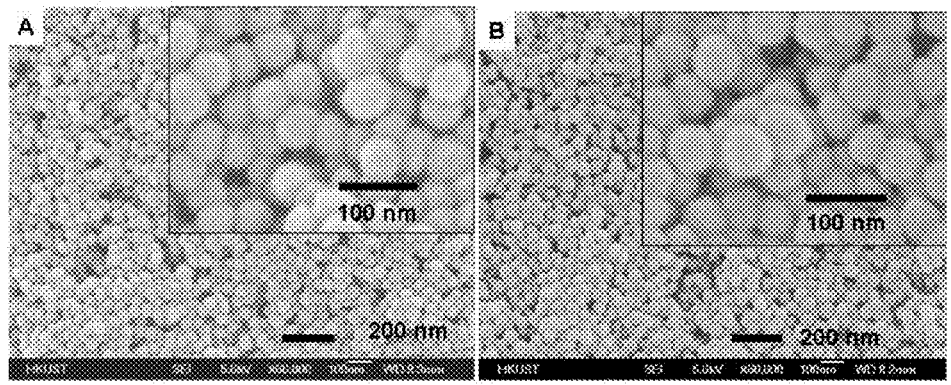

FIG. 61 shows the SEM images of FSNP-39-COOH and FSNP-39-FA.

Figure 62:
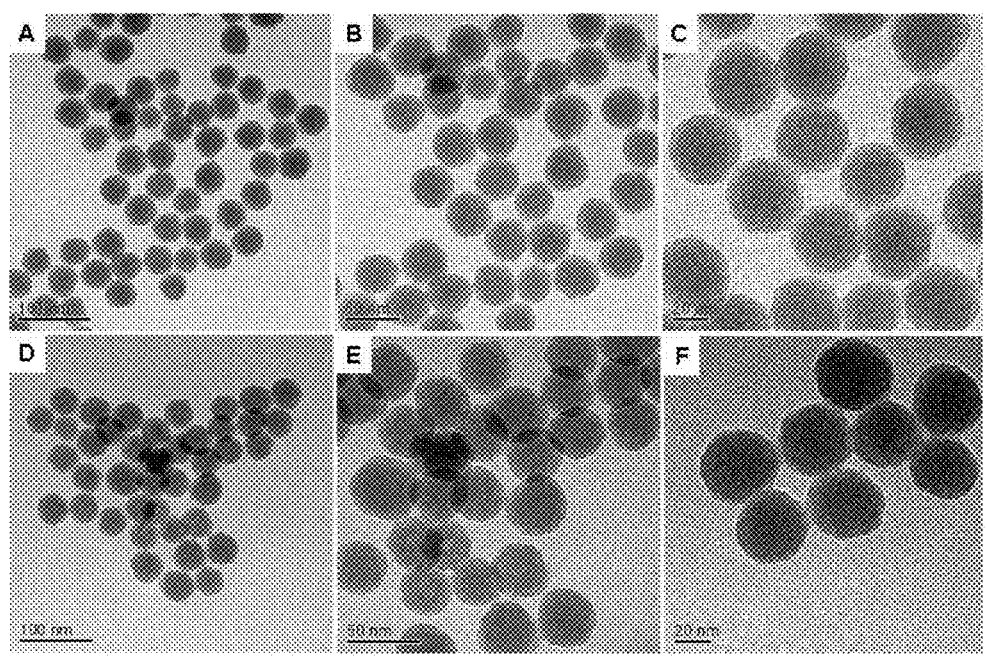

FIG. 62 shows the TEM images of FSNP-39-COOH with particle size of 42.06±3.49 nm and FSNP-39-FA with particle size of 43.33±2.45 nm at different magnifications.

Figure 63:
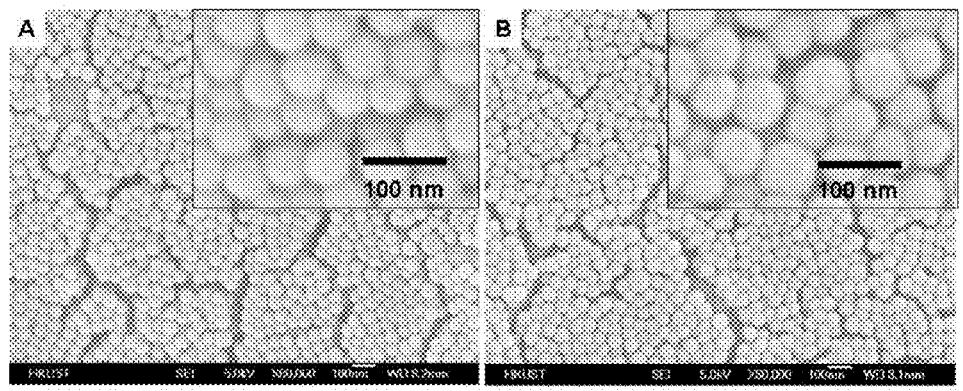

FIG. 63 shows the SEM images of FSNP-7-COOH and FSNP-7-FA.

Figure 64:
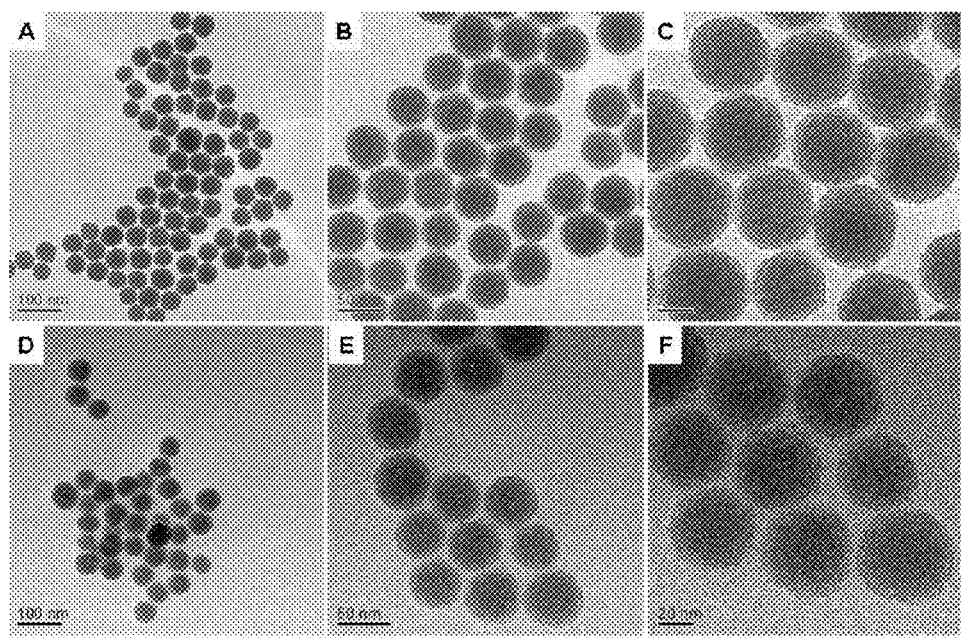

FIG. 64 shows the TEM images of FSNP-7-COOH with particle size of 50.02±3.62 nm and FSNP-7-FA with particle size of 51.79±2.37 nm at different magnifications.

Figure 65:
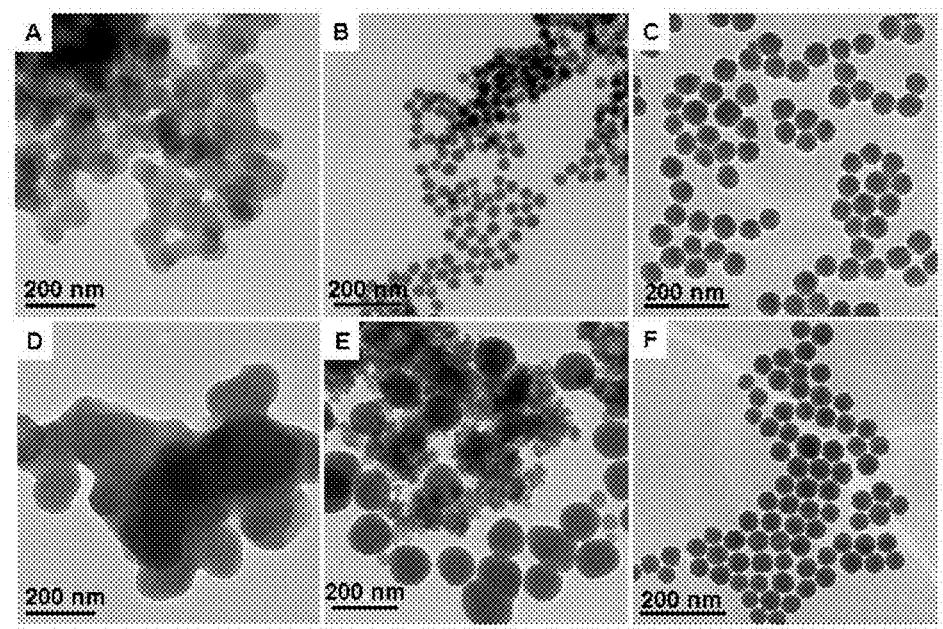

FIG. 65 shows the TEM images of FSNP-39-COOH and FSNP-7-COOH with different morphologies. Scale bar: 200 nm.

Figure 66:
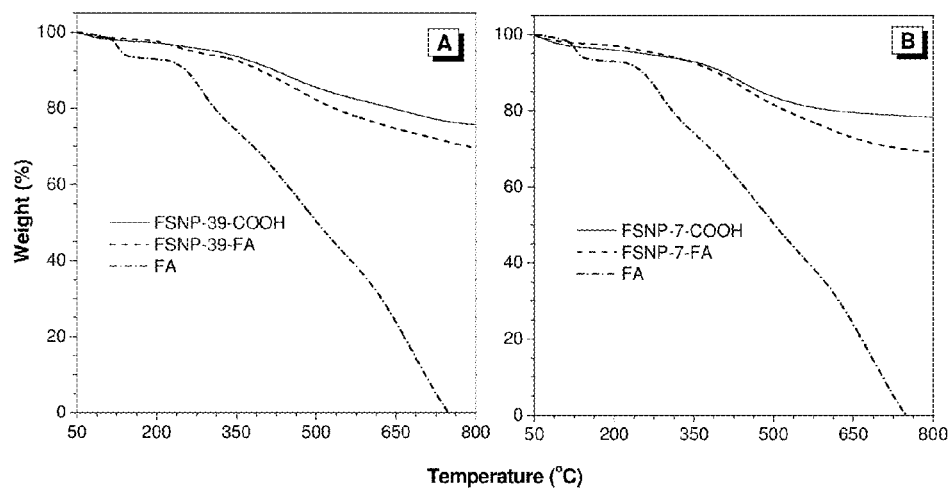

FIG. 66 shows the TGA thermograms of FA, FSNP-39-COOH, FSNP-39-FA, FSNP-7-COOH and FSNP-7-FA.

Figure 67:
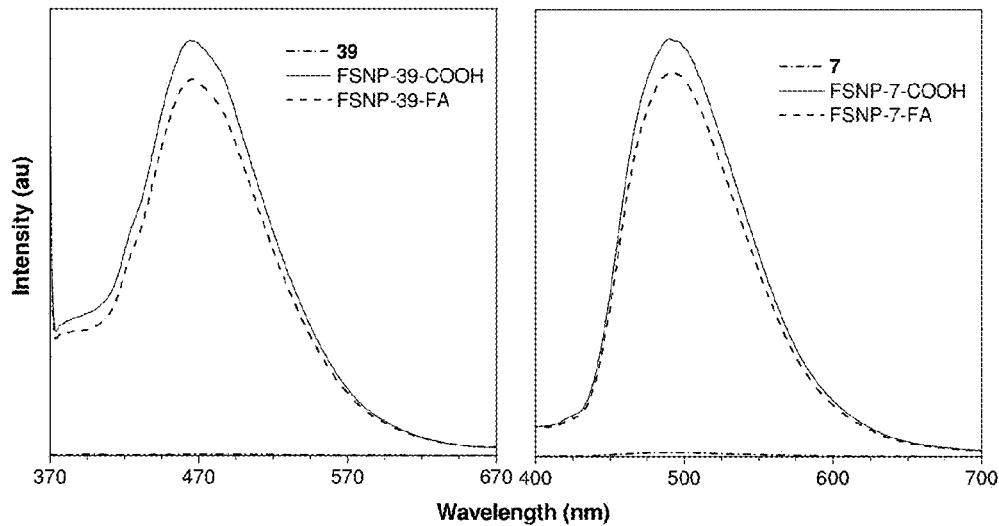

FIG. 67 shows the PL spectra of FSNP-39-COOH, FSNP-39-FA, tetraphenylethene-functionalized siloxane (39), FSNP-7-COOH, FSNP-7-FA and silole-functionalized siloxane (7) in ethanol solutions. Concentration: 200 µg/mL; excitation wavelength (nm): (A) 353 and (B) 370.

Figure 68:
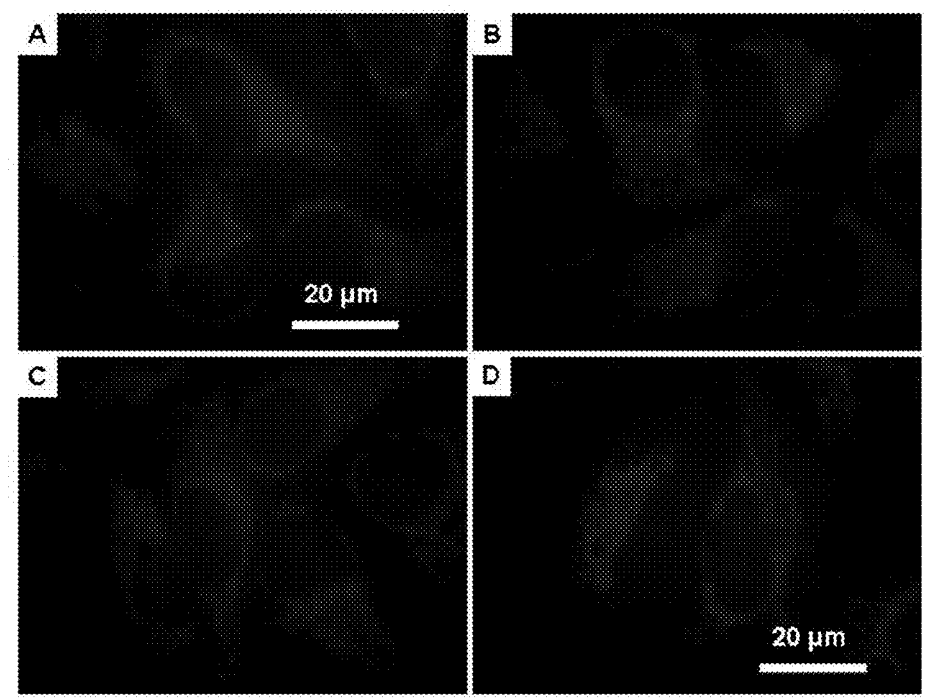

FIG. 68 shows the fluorescent images of HeLa cells incubated with FSNP-39-FA for 1, 2, 3 and 8 h.

Figure 69:
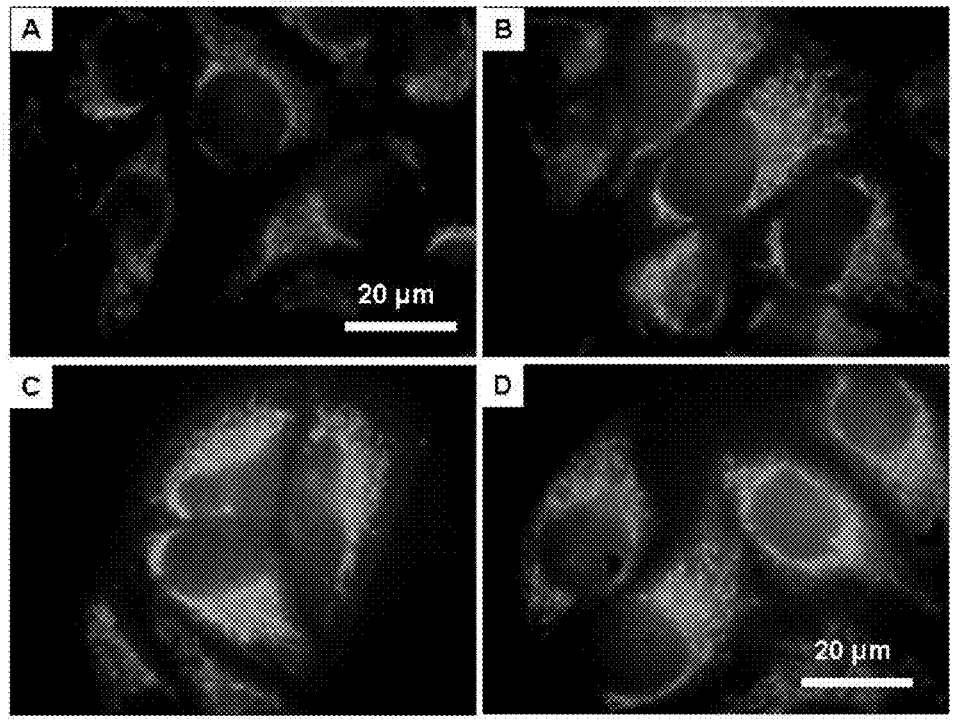

FIG. 69 shows the fluorescent images of HeLa cells incubated with FSNP-7-FA for 1, 2, 3, and 8 h.

Figure 70:
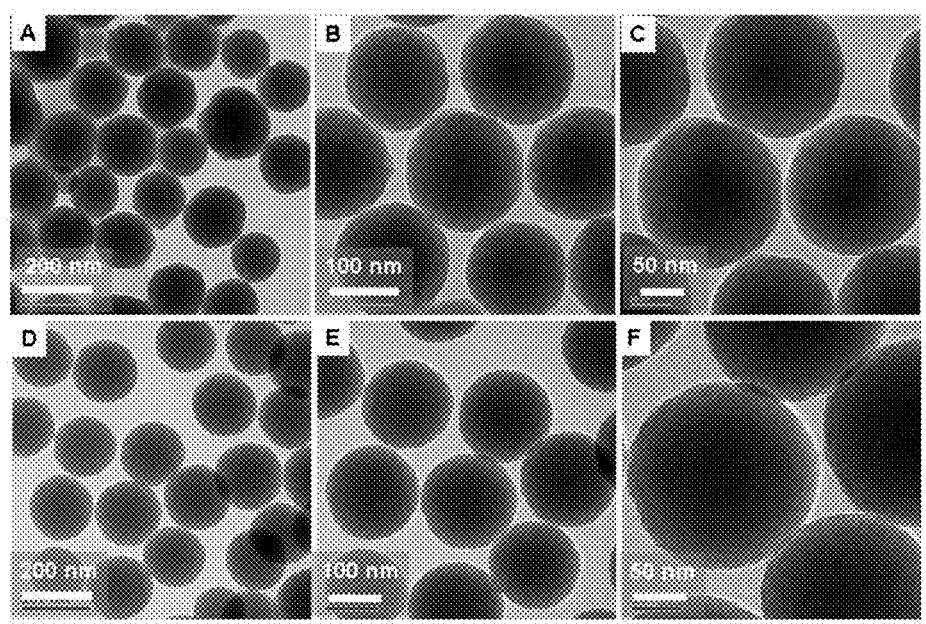

FIG. 70 shows the TEM micrographs of FSNP-39-COOH and FSNP-7-SH at different magnifications with particle sizes of ~163.43±10.29 and 188.02±8.67 nm, respectively.

Figure 71:
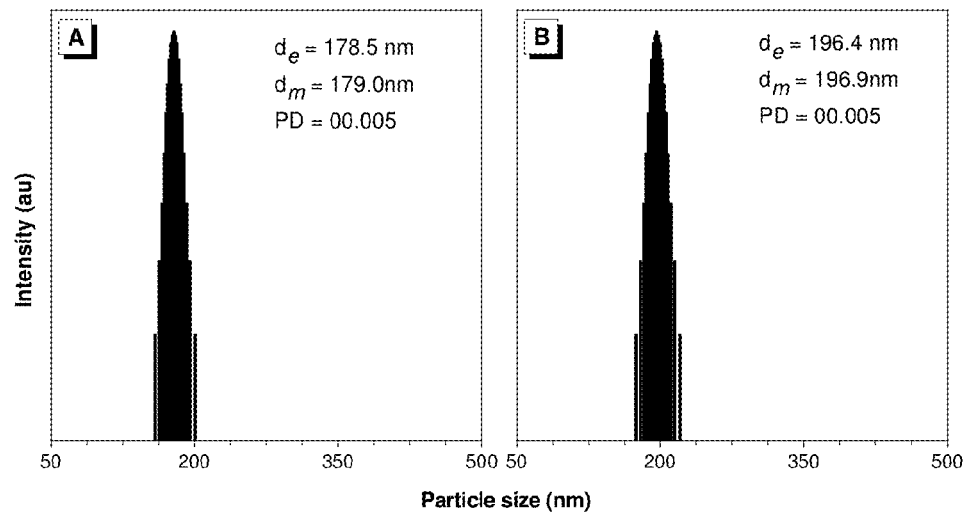

FIG. 71 shows the particle size distributions of FSNP-39-COOH and FSNP-7-SH. Abbreviation: $d_e$=effective diameter, $d_m$=mean diameter, PD=polydispersity.

Figure 72:
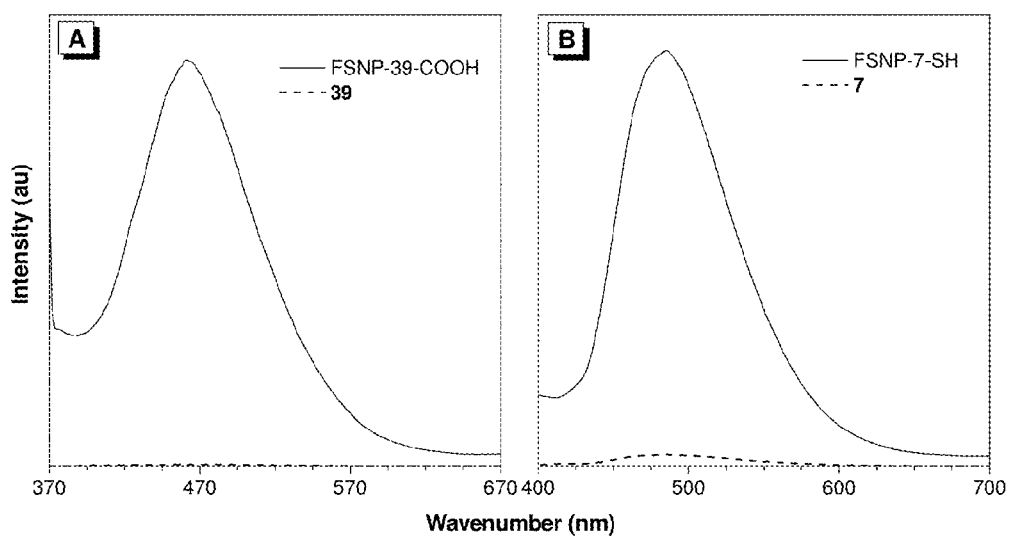

FIG. 72 shows the photoluminescence spectra of FSNP-39-COOH, tetraphenylethene-functionalized siloxane (39), FSNP-7-SH and silole-functionalized siloxane (7) in ethanol solutions. Concentration: 200 µg/mL; excitation wavelength (nm): 353 (FSNP-39-COOH and tetraphenylethene-functionalized siloxane (39)) and 370 (FSNP-7-SH and silole-functionalized siloxane (7)).

Figure 73:
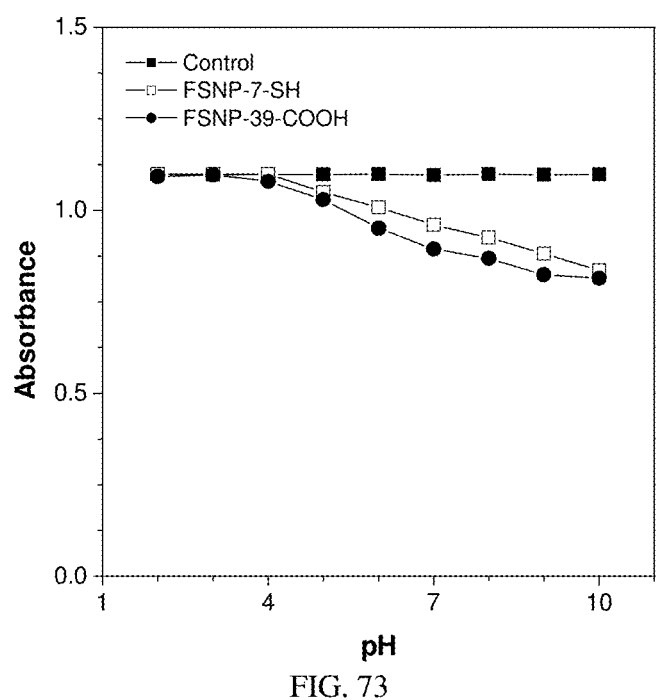

FIG. 73 shows the change in the absorption of buffer solutions of lysozyme at different pH before and after adsorption on the surfaces of FSNP-7-SH and FSNP-39-COOH at room temperature. Concentration: 400 g/mL (lysozyme) and 1 mg/mL (FSNP-7-SH and FSNP-39-COOH).

Figure 74:
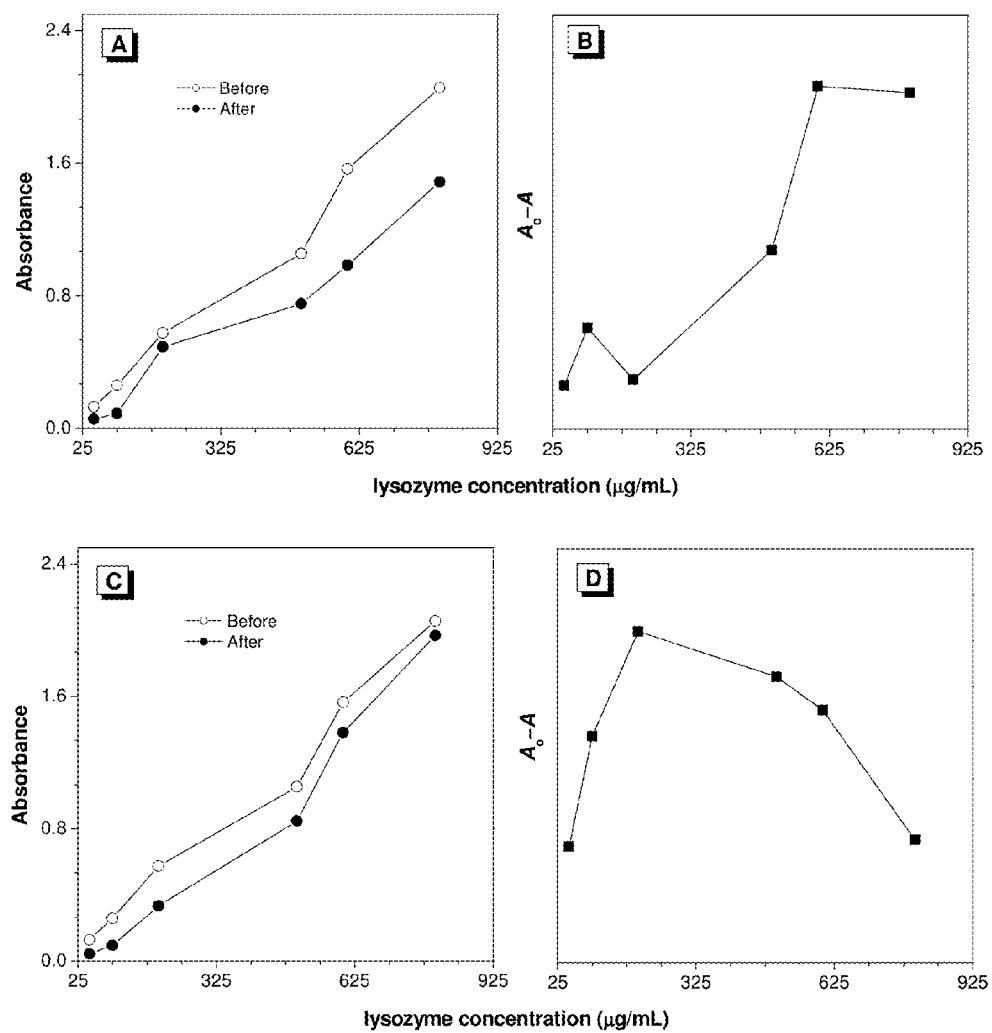

FIG. 74 shows the absorption and absorbance difference ($A_o$–A) of buffer solutions (pH=10) of lysozyme at different concentrations before and after incubated with FSNP-39-COOH and FSNP-2-SH at room temperature for 12 h. Concentration of nanoparticles: 1 mg/mL.

Figure 75:
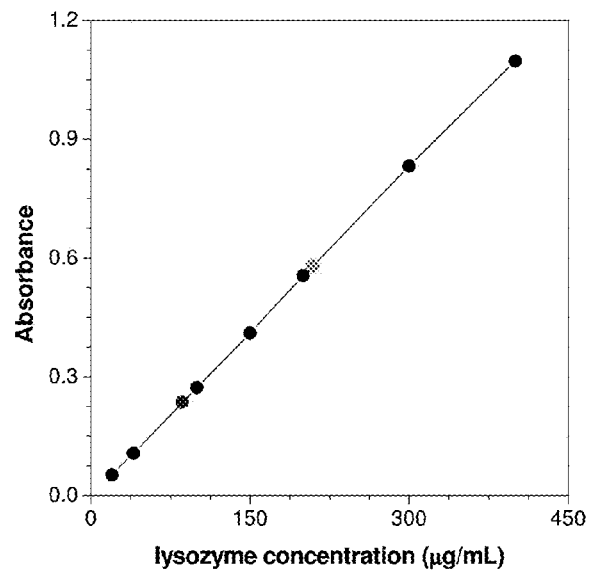

FIG. 75 shows the calibration curve (absorbance versus lysozyme concentration) for the determination of concentrations of lysozyme adsorbed on FSNP-39-COOH (green) and FSNP-7-SH (blue) at room temperature.

Figure 76:
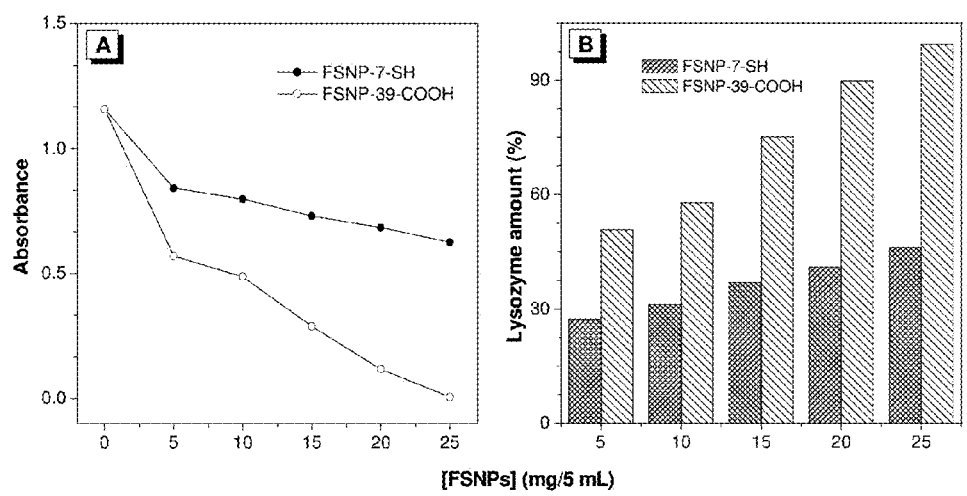

FIG. 76 demonstrates the absorption of buffer solutions (pH=10) of lysozyme after incubation with different concentrations of FSNP-7-SH and FSNP-39-COOH for 12 h at room temperature and the amount of lysozyme adsorbed by FSNP-7-SH and FSNP-39-COOH at different concentrations.

Figure 77:
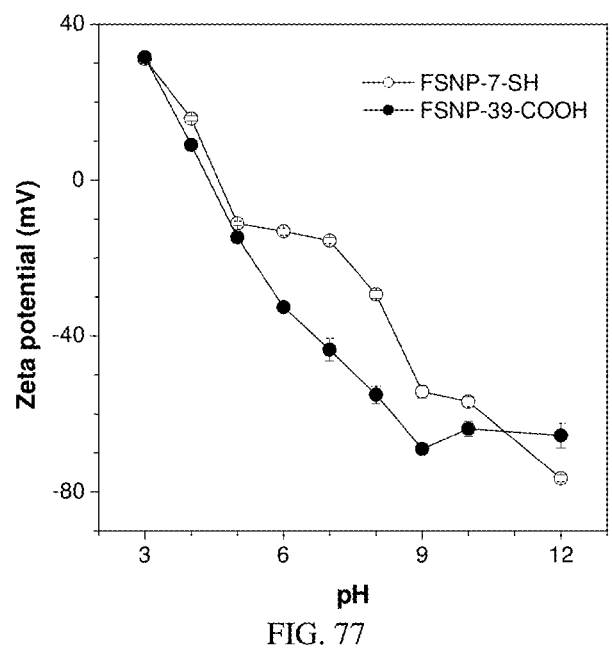

FIG. 77 depicts the zeta potentials of FSNP-7-SH and FSNP-39-COOH in aqueous media with different pH.

DETAILED DESCRIPTION

Definitions

Unless, defined otherwise, all technical and scientific terms used herein have the same meanings as commonly understood by someone ordinarily skilled in the art to which the present subject matter pertains. The following definitions are provided for the purpose of understanding the present subject matter and for constructing the appended patent claims.

The term "acetyl" as used herein refers to the presence of a pendant acetyl group ($COCH_3$) in the structure of the molecules or the material described herein.

The phrase "aggregation caused quenching" or "ACQ" as used herein refers to the phenomenon wherein the aggregation of π-conjugated luminogens significantly decreases the fluorescence intensity of the luminogens. The aggregate formation is said to "quench" light emission of the luminogens.

The phrase "aggregation induced emission" or "AIE" as used herein refers to the phenomenon manifested by compounds exhibiting enhancement of light-emission upon aggregation in the amorphous or crystalline (solid) states whereas they exhibit weak or almost no emission in dilute solutions.

The term "alkyl" as used herein refers to an aliphatic hydrocarbon group which may be a straight or branched chain. The alkyl may comprise about 1 to 15 carbon atoms in the chain, optionally substituted by one or more groups.

The term "aryl" as used herein refers to an optionally substituted monocyclic or multicyclic aromatic carbocyclic moiety, such as phenyl, naphthyl, anthracene, tetracene, pyrene, etc. The aryl may comprise about 6 to 18 carbon atoms.

The term "biomolecule" as used herein refers to a biological substance comprising or consisting of one or more of nucleic acids, proteins and/or complex carbohydrates.

The term "coercivity" as used herein refers to the intensity of the applied magnetic field required to reduce the magnetization of a ferromagnetic material to zero after the magnetization of the sample has been driven to saturation.

The term "cycloalkyl" as used herein refers to an optionally substituted non-aromatic monocyclic or multicyclic ring system. The cycloalkyl may comprise about 3 to 10 carbon atoms.

The phrase "emission intensity" as used herein refers to the magnitude of fluorescence/phosphorescence normally obtained from a fluorescence spectrometer or a fluorescence microscopy measurement.

The term "heteroalkyl" as used herein refers to an alkyl in which at least one carbon atom is replaced by a heteroatom.

The term "heteroaryl" as used herein refers to an optionally substituted aromatic monocyclic or multicyclic organic moiety. The heteroaryl may comprise about 5 to 10 ring members in which at least one ring member is a heteroatom. The heteroatom refers to an atom selected from the group consisting of nitrogen, oxygen, sulfur, phosphorus, boron and silicon.

The term "heterocycloalkyl" as used herein refers to a cycloalkyl group in which at least one ring member is a heteroatom. The heterocycloalkyl may comprise about 3 to 7 ring members.

The term "luminogen" as used herein refers to a chemical compound that manifests luminescence.

The term "nanoparticle" as used herein refers to any microscopic particle or particle population having a mean diameter of about 100 or less nanometers (nm), less than about 90 nm, less than about 80 nm, less than about 70 nm, less than about 60 nm, less than about 50 nm; or having a mean diameter of from 1 nm to less than 100 nm, from 10 nm to less than 100 nm, from 20 nm to less than 100 nm, from 30 nm to less than 100 nm, from 40 nm to less than 100 nm, from 50 nm to less than 100 nm, from 10 nm to 90 nm, or from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The phrase "quantum dots" as used herein refers to a type of matter, i.e., a semiconductor, whose excitons are confined in all three spatial dimensions. Quantum dots can be semiconductors whose electronic characteristics are closely related to the size and shape of the individual crystal. Generally, the smaller the size of the crystal, the larger the band gap, i.e., the difference in energy between the highest valence band and the lowest conduction band becomes greater. Therefore more energy is needed to excite the dot, and concurrently, more energy is released when the crystal returns to its resting state.

The term "remanence" as used herein refers to the magnetization left behind in a ferromagnetic material (such as iron) after an external magnetic field is removed.

The term "vinyl" as used herein refers to the presence of a pendant vinyl group ($CH_2=CH-$) in the structure of the molecules or the material described herein.

Throughout the application, descriptions of various embodiments use "comprising" language; however, it will be understood by one of skill in the art, that in some specific instances, an embodiment can alternatively be described using the language "consisting essentially of" or "consisting of."

The term "a" or "an" as used herein includes the singular and the plural, unless specifically stated otherwise. Therefore, the term "a," "an," or "at least one" can be used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

ABBREVIATIONS

APS: 3-aminopropyltriethoxysilane
BSA: Bovine serum albumin
$d_e$: effective diameter
$d_m$: mean diameter
DCC: 1,3-Dicyclohexylcarbodiimide
DCE: Dichloroethane
DCM: Dichloromethane
DMAP: 4-Dimethylaminopyridine
DMF: Dimethylformamide
DMSO: Dimethylsulfoxide
EDX: Energy-dispersive X-ray
FSNP=Fluorescent Silica Nanoparticle
HRMS: High-resolution mass spectroscopy
IR: Infra-red
MFSNP: Magnetic fluorescent silica nanoparticle
MFSNP-BSA: Bovine serum albumin-decorated magnetic fluorescent silica nanoparticles
MFSNP-$NH_2$: Amino-functionalized magnetic fluorescent silica nanoparticles
MNP: Magnetic nanoparticle
MNP-C: Citrate-modified magnetic nanoparticle
MSNP: Magnetic silica nanoparticle
NHS: 4-Hydroxysuccinamide
PBS: Phosphate-buffered Saline
PD: polydispersity
PL: Photoluminescence
SEM: Scanning electron microscope
SNPs: Silica nanoparticles
TEM: Transmission electron microscope
TEOS: Tetraethoxysilane
TGA: Thermogravimetric analysis
THF: Tetrahydrofuran
TsOH: p-Toluenesulfonic acid
XPS: X-ray photoelectron spectroscopy The present subject matter relates to the phenomenon, known as aggregation-induced emission (AIE), wherein nonemissive luminogens such as tetraphenylethene (TPE) and hexaphenylsilole are induced to emit efficiently in aggregate formation. The AIE effect dramatically boosts the fluorescence quantum yields of the luminogens, changing them from faint fluorophores to strong emitters.

Furthermore, encapsulation of luminogens, by physical methods or covalent bonds to the host materials, protects them against chemically reactive species, such as oxygen. Among various host materials, silica nanoparticles exhibit high chemical, thermal, and colloidal stabilities in aqueous media and are environmentally friendly due to their inertness. In addition, silica nanoparticles are optically transparent and show no or very limited reactivity to microbes. Furthermore, since their surfaces contain numerous silanol groups, a wide variety of surface reactions and binding of biomolecules can occur.

Therefore, the present subject matter is related to magnetic and/or fluorescent silica nanoparticles (MFSNPs and FSNPs) with aggregation induced emission properties and practical applications as fluorescent probes for bioimaging and protein carriers. Magnetic nanoparticles and AIE luminogens are prepared and integrated into the silica network through new synthetic approaches. Accordingly, the present subject matter is directed to magnetic fluorescent silica nanoparticles and fluorescent silica nanoparticles with core-shell structures, substantially uniform sizes, high surface charges, and excellent colloidal stability. The magnetic fluorescent silica nanoparticles are superparamagnets with high magnetization. Both magnetic fluorescent silica nanoparticles and fluorescent silica nanoparticles emit strong light upon photoexcitation. In addition, their emission efficiencies can be further enhanced by increasing the luminogen loading. The magnetic fluorescent silica nanoparticles and fluorescent silica nanoparticles are nontoxic to living cells and function as fluorescent visualizers for intracellular imaging. Magnetic fluorescent silica nanoparticles also have high-technological applications in ultrasensitive assays, living cell labeling, biological separation, site-specific drug delivery, magnetic resonance imaging, and magnetocytosis. Furthermore, modification of the surfaces of magnetic fluorescent silica nanoparticles and fluorescent silica nanoparticles with specific functional groups enables them to function as protein carriers and conjugate with biomolecules for targeting specific cancer cells.

In the present subject matter, magnetic nanoparticles and AIE luminogens are prepared and utilized as magnetic cores and fluorophores for the construction of MFSNPs and FSNPs. The AIE luminogens are linked to triethoxysilane through chemical reactions using thiol-click chemistry and Cu-catalyzed alkyne-azide cycloaddition. Surfactant-free sol-gel reactions of the organic-inorganic adducts followed by reactions with tetraethoxysilane in the presence or absence of citrate-coated magnetite generate MFSNPs and FSNPs with core-shell structures, substantially uniform sizes, high surface charges, and excellent colloidal stabilities. The AIE dyes can also be immobilized on the surfaces of silica nanoparticles using a click reaction. The MFSNPs are magnetically susceptible with zero remanence and coercivity, indicating they are good superparamagnets with high magnetization. Both MFSNPs and FSNPs emit strong lights when photoexcited, and their emission efficiencies increase with increasing luminogen loading. In addition, neither MFSNPs nor FSNPs are toxic to living cells. Rather, MFSNPs and FSNPs can function as fluorescent visualizers for intracellular imaging. Furthermore, modification of the surfaces of MFSNPs and FSNPs with specific functional groups allows them to function as protein carriers and conjugate with biomolecules, which enhances their binding specificities.

Specifically, one embodiment of the present subject matter is directed to a fluorescent bioprobe for intracellular imaging comprising an aggregation induced emission luminogen and magnetite nanoparticles; wherein the luminogen has a backbone structure selected from the group consisting of:

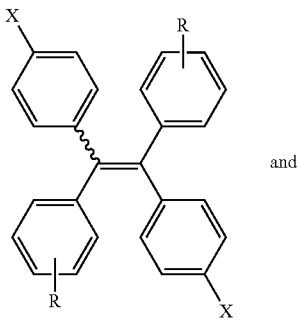

and

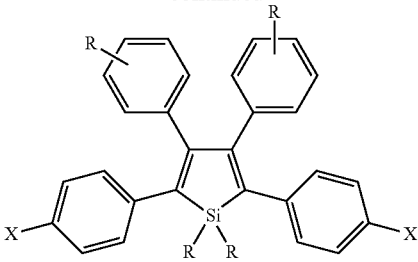

wherein R is selected from the group consisting of H, alkyl, unsaturated alkyl, aryl, vinyl, acetyl, heteteroalkyl, cycloalkyl, heterocycloalkyl, and heteroaryl; X is selected from the group consisting of $(CH_2)_n$, $C_6H_5$, $(Ph)_n$, $O(CH_2)_n$, $NH(CH_2)_n$, $N[(CH_2)_n]_2$, and $(OCH_2CH_2)_n$; and n=0 to 20; wherein X is capable of conjugating with a siloxane; and wherein the fluorescent bioprobe is selected from the group consisting of magnetic fluorescent silica nanoparticles and fluorescent silica nanoparticles.

In another embodiment, the present subject matter is directed to the fluorescent bioprobe, described above, wherein the luminogen has a chemical structure selected from the group consisting of:

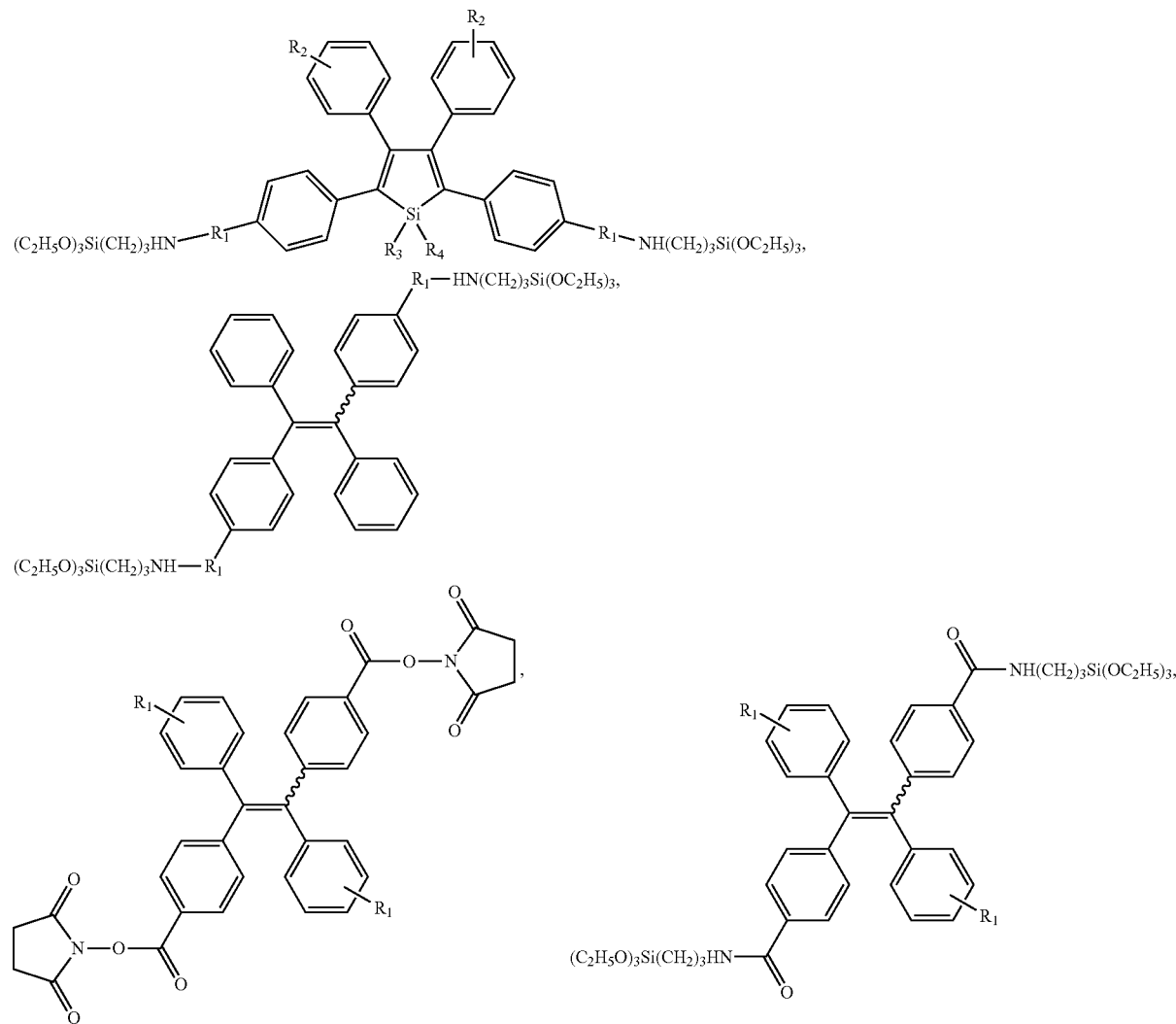

-continued
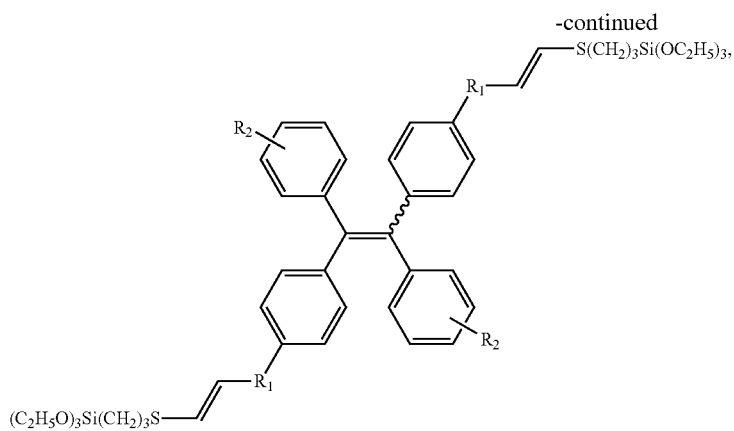
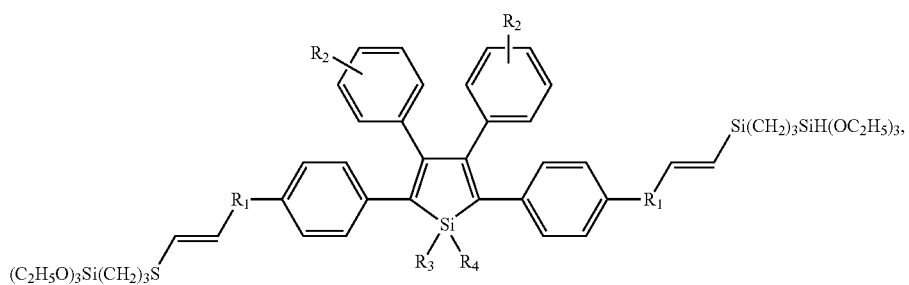
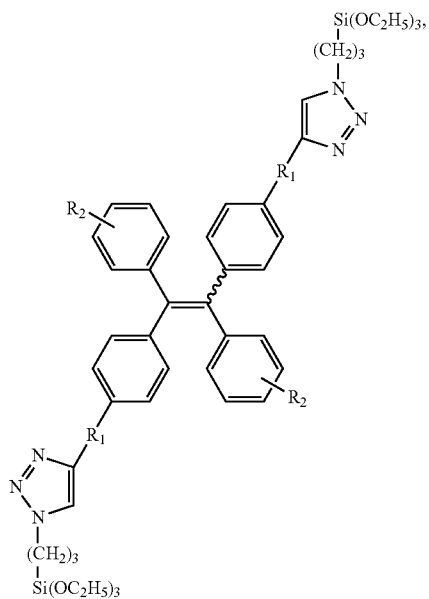
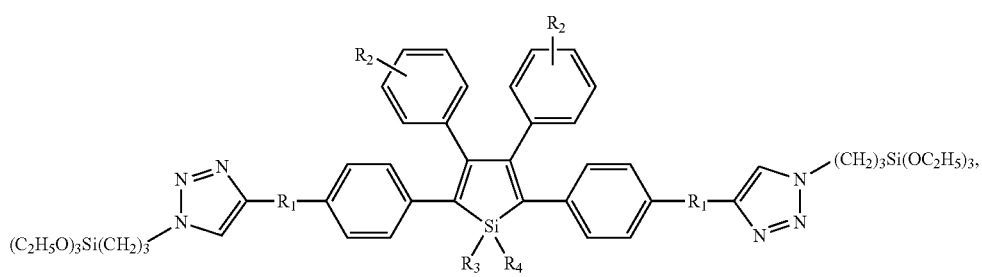

-continued

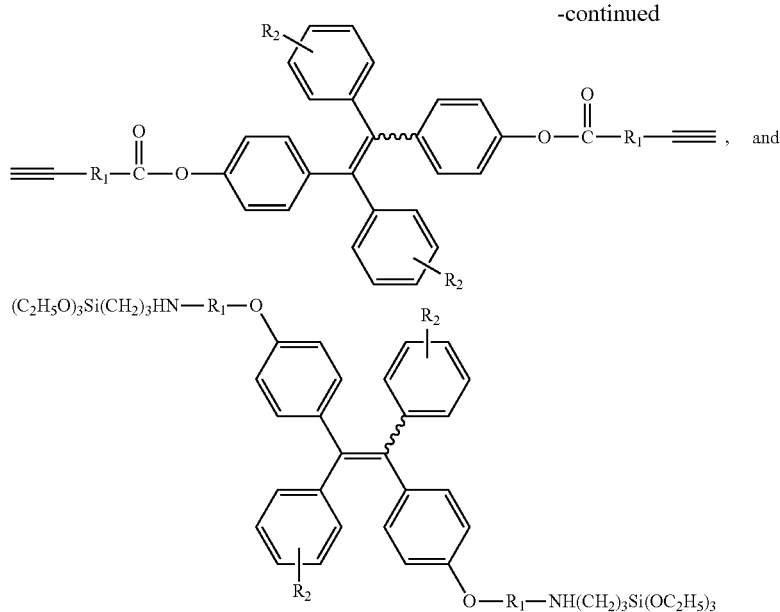

wherein $R_1$, $R_2$, $R_3$, and $R_4$ are substituents independently selected from the group consisting of H, alkyl, unsaturated alkyl, aryl, vinyl, acetyl, heteroalkyl, cycloalkyl, heterocycloalkyl, aryl, and heteroaryl.

The fluorescent bioprobes are nontoxic to living cells and can be effectively taken up by cancer cells. Therefore, the fluorescent bioprobes can be used to image the cytoplasm of cancer cells. Furthermore, the fluorescent bioprobes can target specific cancer cells. In addition to being used for intracellular imaging, the fluorescent bioprobes can also be used as protein carriers. In that regard, the magnetic fluorescent silica nanoparticles and the fluorescent silica nanoparticles can adsorb protein molecules such as BSA and lysozyme.

The magnetic fluorescent silica nanoparticles and the fluorescent nanoparticles exhibit aggregation-induced emission. In addition, the light emission of the magnetic fluorescent silica nanoparticles and the fluorescent silica nanoparticles increases with increased luminogen loading. In one embodiment, the AIE luminogen is in a solid form. Furthermore, the magnetic fluorescent silica nanoparticles and the fluorescent silica nanoparticles are spherical with substantially uniform sizes and narrow particle distributions, in addition to having high surface charges and good colloidal stabilities.

In one embodiment, the fluorescent bioprobe comprises magnetic fluorescent silica nanoparticles which comprise magnetic cores covered by a silica shell. The magnetic fluorescent silica nanoparticles exhibit superparamagnetism. Furthermore, the magnetic fluorescent silica nanoparticles exhibit high magnetization with negligible remanence and coercivity. In another embodiment, the fluorescent bioprobe comprises fluorescent silica nanoparticles which comprise fluorescent cores covered by a silica shell.

In one embodiment, the AIE luminogen is covalently bonded to a silica network through amine and amide functional groups. In another embodiment, the AIE luminogen is covalently bonded to silica nanoparticles via thiol-click chemistry and alkyne-azide cylcoaddition. In a further embodiment, the AIE luminogen is grafted onto the surface of silica nanoparticles by click chemistry.

In another embodiment, the magnetic fluorescent silica nanoparticles and the fluorescent nanoparticles are surface functionalized with one or more functional groups selected from the group consisting of amino, azido, carboxylic acid, and thiol functional groups. Alternatively, the magnetic and fluorescent silica nanoparticles can be surface functionalized with one or more biomolecules selected from the group consisting of glucose, galactose, and folic acid. In one embodiment, the magnetic and fluorescent silica nanoparticles are conjugated with one or more biomolecules via click chemistry and an esterification reaction.

In another embodiment, the present subject matter is directed to a process for preparing the magnetic fluorescent silica nanoparticles comprising a sol-gel reaction of silole-APS conjugate and teraethoxysilane in a magnetic fluid of magnetite. Similarly, the present subject matter is also related to a process for preparing the fluorescent silica nanoparticles comprising a first sol-gel reaction of tetraphenylethene-containing siloxane, followed by a second sol-gel reaction with tetraethoxysilane.

In another embodiment, the process for preparing the fluorescent silica nanoparticles comprises: (a) preparation of tetraphenylethene-containing siloxane and silole-containing siloxane by thiol-click chemistry; (b) sol-gel reactions of the tetraphenylethene-containing siloxane and the silole-containing siloxane; and (c) reactions of the tetraphenylethene-containing siloxane and silole-containing siloxane with tetraethoxysilane.

In a further embodiment, the process for preparing the fluorescent silica nanoparticles of claim 1 comprises: (a) preparation of 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33) by click chemistry; (b) sol-gel reactions of 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33); and (c) reactions of 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33) with tetraethoxysilane.

The present subject matter also relates to a process for the fabrication of the fluorescent silica nanoparticles comprising surface grafting of the aggregation induced emission luminogen onto the magnetite nanoparticles by click chemistry.

In another embodiment, the present subject matter relates to a process for surface functionalization of the fluorescent silica nanoparticles comprising bioconjugation with glucose molecules using alkyne-azide cylcoaddition. In a further embodiment, the present subject matter relates to a process for the fabrication of galactose-functionalized fluorescent silica nanoparticles comprising a click reaction of sugar-bearing phenylacetylene with FSNP-41-$N_3$ and FSNP-7-$N_3$, respectively. In a further embodiment, the process of preparing folic acid-functionalized fluorescent silica nanoparticles comprises a reaction of folic acid with FSNP-39-COOH and FSNP-7-COOH, respectively. Finally, the present subject matter also relates to a process for preparing lysozyme-decorated fluorescent silica nanoparticles comprising adsorption of lysozyme by FSNP-30-COOH and FSNP-7-COOH.

The present subject matter can be illustrated in further detail by the following examples. However, it should be noted that the scope of the present subject matter is not limited to the examples. They should be considered as merely being illustrative and representative for the present subject matter.

EXAMPLES

The examples below demonstrate various embodiments of the present subject matter.

Example 1

Synthesis of Citrate-Modified Magnetite Nanoparticles

Tetraethoxysilane (TEOS), dimethylsulfoxide (DMSO), (3-aminopropyl)triethoxysilane (APS), ferric chloride ($FeCl_3.6H_2O$), ferrous chloride ($FeCl_2.4H_2O$), and other reagents were all purchased from Aldrich and used as received. Silole-APS adduct (7) was prepared according to previous published procedures (Chem. Eur. J. 2010, 16, 4266). High resolution mass spectrum was recorded on a Finnigan TSQ 7000 triple quadrupole spectrometer operating in a MALDI-TOF mode. The morphologies and electron diffraction patterns of the magnetite and magnetic fluorescent silica nanoparticles were investigated using a JOEL 2010 transmission electron microscope (TEM) at an accelerating voltage of 200 kV. Samples were prepared by drop-casting dilute dispersions onto copper 400-mesh carrier grids covered with carbon-coated formvar films. The solvent was evaporated in open air at room temperature. The size and thickness of the metal core and the silica shell were measured using TEM software (Digital Micrograph 365 Demo). The diameter of the magnetic core at different directions was measured and the mean value was reported. Photoluminescence spectra were recorded on a Perkin-Elmer LS 50B spectrofluorometer with a Xenon discharge lamp excitation. The zeta potentials of the nanoparticles (0.05 mg/mL) were determined in aqueous media at room temperature using a ZetaPlus Potential Analyzer (Brookhaven Instruments Corporation, USA). The pH of the suspensions was adjusted by adding hydrochloric acid and ammonium hydroxide solutions. Magnetization of the nanoparticles was measured using a superconducting quantum interference device magnetometer (Quantum Design MPMS-JS).

The synthesis of citrate-modified magnetite nanoparticles is shown in the chemical reaction scheme, below.

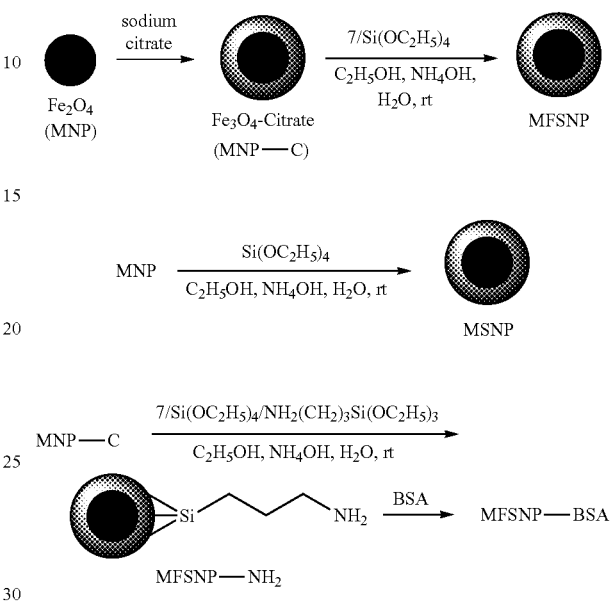

Citrate-modified magnetite nanoparticles (MNP-C) were prepared by chemical coprecipitation of iron salts in basic medium followed by surface coating of the resultant magnetite nanoparticles by citrate ions. The precipitation was carried out in aqueous solutions containing an equal molar ratio of $Fe^{2+}$ to $Fe^{3+}$ at pH~10 to 11. 0.20 g of $FeCl_2.4H_2O$ and 0.27 g of $FeCl_3.6H_2O$ were dissolved in 75 mL of water in a 250 mL round-bottom flask. After the solution was stirred under nitrogen bubbling for 15 min at 40° C., 6 mL of 1.5 M aqueous ammonium hydroxide solution was added. The pH of the solution was kept at ~10 by further addition of 3-4 mL of ammonium hydroxide solution. The color of the solution immediately changed from yellow to black due to the formation of magnetite nanoparticles. The temperature was then raised to 60° C. and the solution was stirred for another 30 min. 20 mL of 0.3 M aqueous sodium citrate solution was added and the solution was stirred and heated to 90° C. for 30 min to complete the surface coating. The resultant citrate-modified magnetite nanoparticles were repeatedly precipitated in acetone and washed with deionized water three times, and dried under vacuum to a constant weight.

Example 2

Fabrication of Magnetic Fluorescent Silica Nanoparticles

Silole-APS conjugate (7) was prepared by stirring a solution of 6 μmol of 1,1-dimethyl-2,5-bis[4-(2-bromoethoxy)phenyl]-3,4-diphenylsilole and 16 μmol of APS in 50 μL of DMSO overnight. The chemical structure of the silole-APS conjugate (7) is shown below.

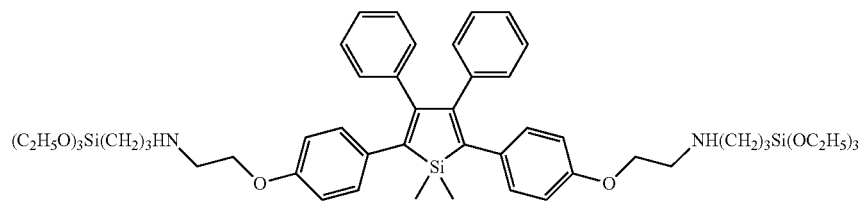

7

Water was excluded to avoid the possible hydrolysis of the APS to form nanoparticles. The reaction mixture was concentrated under high vacuum and the product was characterized by mass spectroscopy. The magnetic fluorescent silica nanoparticles (MFSNPs) were fabricated following the Stöber method with some modifications. An ethanol solution (1 mL) of adduct silole-APS conjugate (7) (6 µmol) and 0.2 mL tetraethoxysilane was first prepared. 10.0 mg of MNP-C in 32 mL of ethanol with 1.0 mL of ammonium hydroxide and 8.0 mL of distilled water was dispersed into another flask. The mixture was sonicated for 5 min in order to obtain a stable and homogenous magnetic dispersion. The solution containing silole-APS conjugate (7) and tetraethoxysilane was then added into the magnetic fluid and the mixture was stirred at room temperature for 24 h. Afterwards, the mixture was centrifuged and redispersed in ethanol. Such process was repeated three to four times and the resultant MFSNPs were finally dispersed in water for further applications. MFSNP-NH$_2$ was synthesized by sol-gel reaction of APS, silole-APS conjugate (7), and tetraethoxysilane in the presence of MNP-C in basic ethanol/water mixture. The procedures were the same for the fabrication of MFSNPs. The MFSNP-NH$_2$ was dispersed in water for the BSA adsorption.

Figure 1:
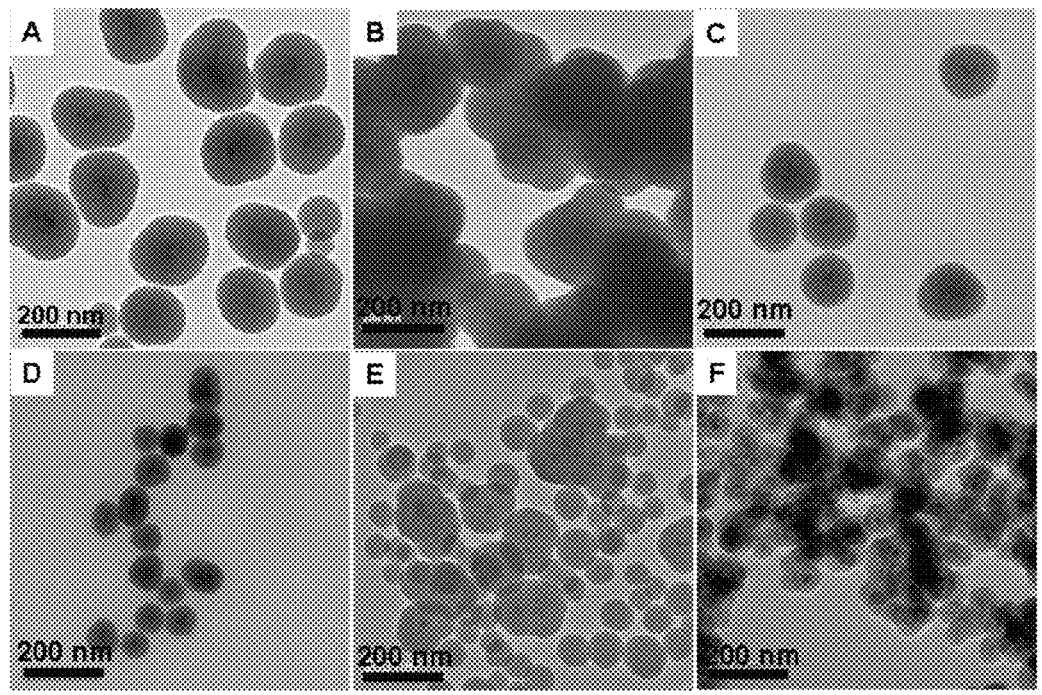
FIG. 1 shows TEM images of MFSNP-1, MFSNP-2, MFSNP-3, MFSNP-4, MFSNP-5, and MFSNP-6.

Table 1, below, and FIG. 1 show the effects of MNP-C, TEOS, and NH$_4$OH concentrations on the morphology of the resultant MFSNPs. Under the conditions shown in Table 1, row 1, discrete, uniform nanoparticles are formed in MFSNP-1. However, lowering the TEOS concentration has decreased the thickness of the silica shell and hence the size of the resultant MFSNP-2. The particles of MFSNP-2 are aggregated because not all the triethoxysilyl groups of Silole-APS conjugate (7) are hydrolyzed and remain on the particle surface. The particles of MFSNP-3 are smaller than MFSNP-1 but larger than those of MFSNP-4 as the amount of MNP-C used for the sol-gel reaction is in between those for the fabrication of MFSNP-1 and MFSNP-4. Ammonium hydroxide plays an important role in the sol-gel process. The hydrolysis of TEOS and Silole-APS conjugate (7) becomes slower in the presence of small amounts of NH$_4$OH, which leads to the particle aggregation and promotes the formation of fluorescent silica nanoparticles (FIG. 1E). The particles of MFSNP-6 are also clustered together due to the insufficient amount of TEOS in the reaction mixture, which cannot coat and encapsulate all the particles of MNP-C and Silole-APS conjugate (7).

TABLE 1

Preparation of MFSNPs[a]

| no. | nanoparticle | MNP-C (mg) | Si(OC$_2$H$_5$)$_4$ (mL) | NH$_4$OH (mL) | H$_2$O (mL) | C$_2$H$_5$OH (mL) | Conjugate (7) (µmol) |
|---|---|---|---|---|---|---|---|
| 1 | MFSNP-1 | 2.5 | 0.2 | 1 | 8 | 33 | 6 |
| 2 | MFSNP-2 | 2.5 | 0.1 | 0.5 | 4 | 33 | 6 |
| 3 | MFSNP-3 | 5.0 | 0.2 | 1 | 8 | 33 | 6 |
| 4 | MFSNP-4 | 10 | 0.2 | 1 | 8 | 33 | 6 |
| 5 | MFSNP-5 | 10 | 0.2 | 0.5 | 4 | 33 | 6 |
| 6 | MFSNP-6 | 20 | 0.2 | 1 | 8 | 33 | 6 |

[a] Carried out at room temperature for 24 h.

Figure 2:
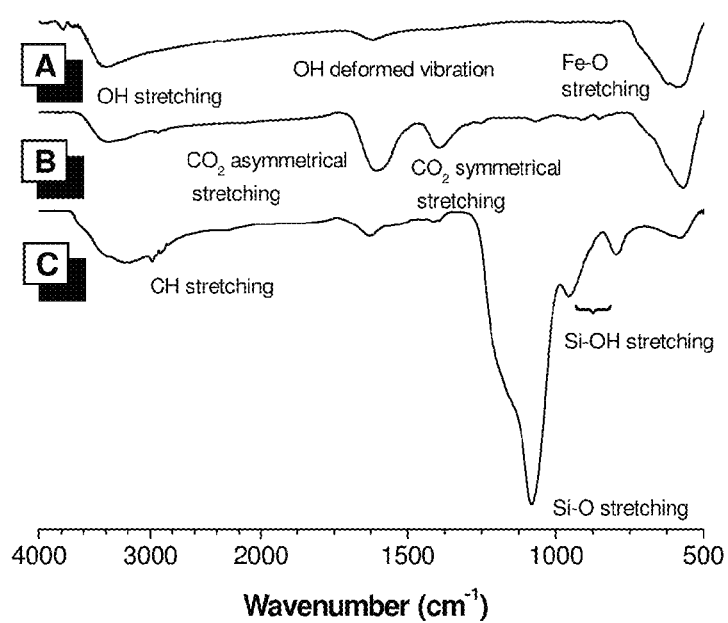
FIG. 2 illustrates the IR spectra of MNPs, MNP-C, and MFSNP-4.
Figure 3:
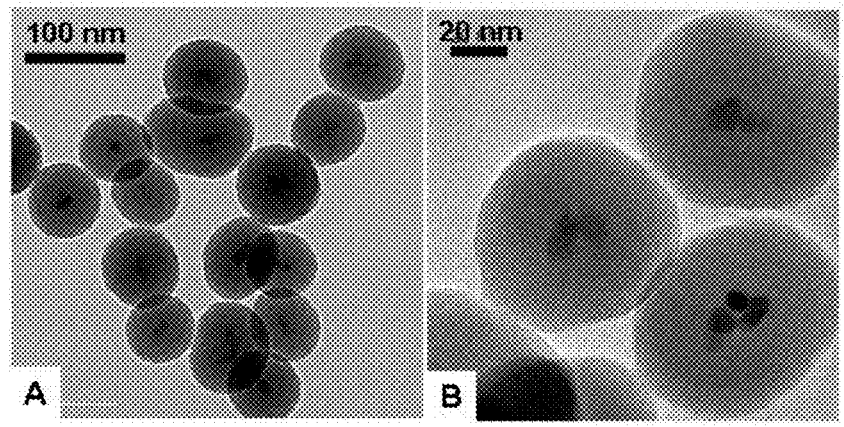
FIG. 3 shows TEM images of MFSNP-4 at different magnifications.

As show in FIG. 2, the structure of MFSNPs was characterized by infra-red (IR) spectroscopy. The MNPs show O—H stretching, O—H deformed, and Fe—O stretching vibrations at 3408, 1633, and 584 cm$^{-1}$, respectively. After surface coating, the first two peaks are intensified due to their overlapping with the O—H and CO$_2$ asymmetrical stretchings of the citrate ions. A new peak associated with CO$_2$ symmetrical stretching is also observed at 1381 cm$^{-1}$. All these suggest the success of the formation of MNP-C. After sol-gel reaction with silole-APS conjugate (7) and TEOS, the peak intensity at ~3300 cm$^{-1}$ is further enhanced. Weak absorptions assigned to C—H stretching vibration of silole-APS conjugate (7) are observed at 2980 and 2870 cm$^{-1}$ in MFSNPs. Absorption peaks associated with Si—O and Si—OH stretching vibrations are also emerged at 1081, 951, and 751 cm$^-$, revealing that silole-APS conjugate (7) and TEOS are covalently bonded on the MNP-C surface through silanization with the OH groups. FIG. 3 shows the transmission electron microscope (TEM) image of MFSNP-4. The nanoparticles are monodispersed with magnetic cores (mean diameter=19.15±6.35 nm) surrounded by a silica shell with thickness of 27.98±2.06 nm.

Figure 4:
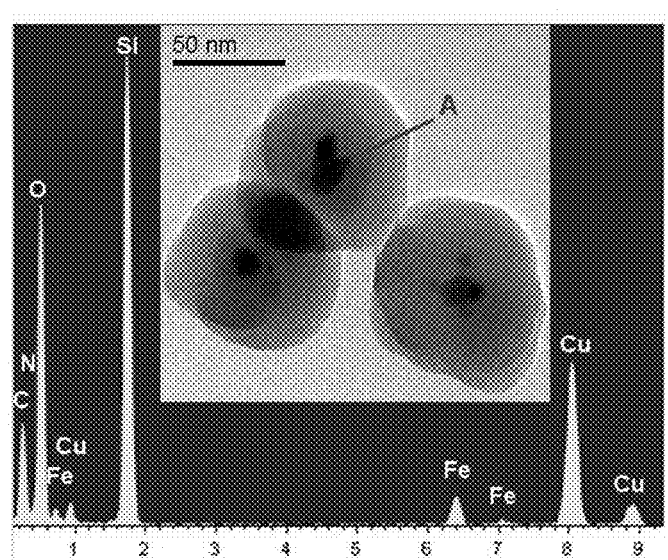
FIG. 4 illustrates the EDX spectrum of MFSNP-4 and the TEM image of the analysis site.
Figure 5:
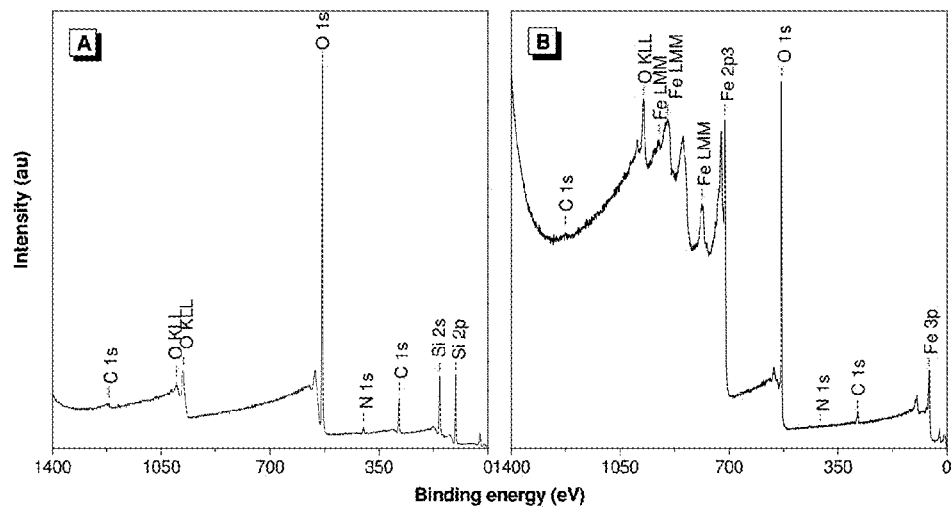
FIG. 5 illustrates the XPS spectra of (A) MFSNP-4 and (B) MNP-C.
Figure 6:
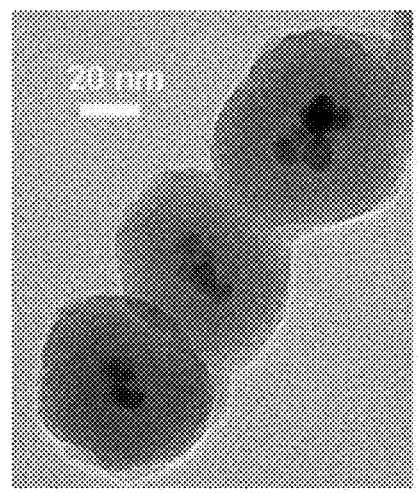
FIG. 6 shows a TEM image of MFSNP-NH$_2$.
Figure 7:
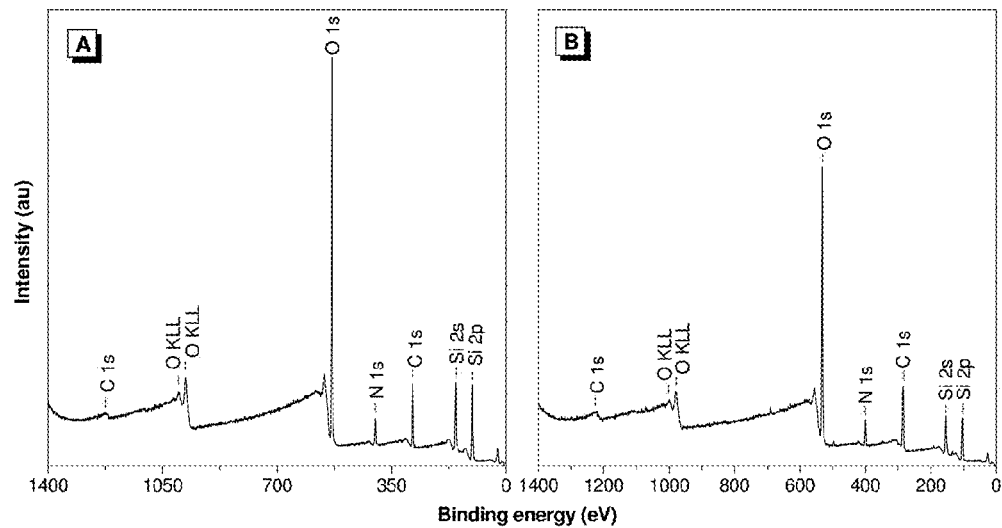
FIG. 7 illustrates the XPS spectra of MFSNP-NH$_2$ and MFSNP-BSA.

The compositions of the MFSNPs were determined by energy dispersive X-ray (EDX) and X-ray photoelectron (XPS) spectroscopies. The EDX spectrum of MFSNP-4 depicts Fe, Si, O, N, and C elements (FIG. 4). In contrast, as shown in Table 2, below, no nitrogen and silicon atoms are detected in MNP-C. XPS analysis reveals that MFSNP-4 contains the expected silicon and nitrogen atoms (FIG. 5). The surface of MFSNP-4 is mainly comprised of oxygen (57%) with small amounts of carbon (14.41%) and nitrogen (1.16%). A considerable amount of silicon (26.98%) is detected on the surface. No iron species are found, revealing that MNP-C are mainly confined in the interior of the MFSNP-4. Similarly, the XPS spectrum of MNP-C gives no peaks corresponding to Si2s and Si2p species at 154 and 101 eV, respectively, but displays Fe2p3/2 peaks at 712 and 725 eV, which are in agreement with the oxidation state of Fe in Fe3O4 (FIG. 5B). Like MFSNP-4, the particles of MFSNP-NH$_2$ are uniform with expected compositions on the surface (FIGS. 6 and 7 and Table 2).

TABLE 2

Chemical compositions of the nanoparticles determined by EDX and XPS analyses

| nanoparticle | carbon | nitrogen | oxygen | silicon | iron |
|---|---|---|---|---|---|
| EDX | | | | | |
| MNP-C | 50.99 | | 7.75 | | 41.26 |
| MFSNP-4 | 10.56 | 0.49 | 31.84 | 45.77 | 11.34 |
| XPS | | | | | |
| MNP-C | 4.95 | 0.44 | 52.39 | | 41.95 |
| MFSNP-4 | 14.41 | 1.96 | 56.65 | 26.98 | |
| MFSNP-NH$_2$ | 11.90 | 5.58 | 50.11 | 24.40 | |
| MFSNP-BSA | 21.58 | 6.68 | 45.74 | 17.18 | |

Figure 8:
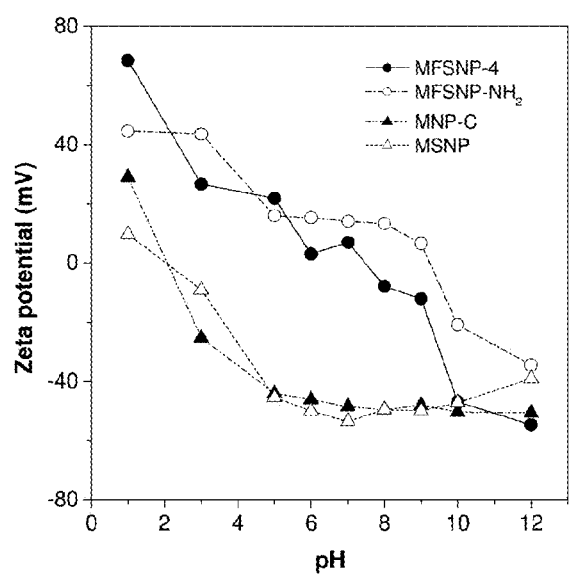
FIG. 8 illustrates the zeta potentials of MNP-C, MSNPs, MFSNP-4 and MFS-NH$_2$ in aqueous media with different pH at room temperature.

The zeta potentials of the nanoparticles in aqueous media with different pH at room temperature are shown in FIG. 8. Similar to MNP-C and MSNPs, MFSNP-4 possess appreciable surface charges and hence good colloidal stability. The zeta potentials of MNP-C and MSNPs are negatively signed in almost the whole pH range, whose absolute magnitudes increase with increasing pH value. At high pH or in the basic medium with high basicity, the acidic hydroxyl groups on the surfaces of MNP-C and MSNPs are converted into basic form, thus imparting them high negative charges. MFSNP-4 and MFSNP-NH$_2$, however, exhibit positively signed zeta potentials at low pH due to the protonation of the amino groups contributed from the silole-APS conjugate (7) and APS. This event is less likely to occur at high pH but the dissociation of the hydroxyl groups is favored. This explains why the zeta potentials of MFSNP-4 and MFSNP-NH$_2$ are changed to negative and become higher with an increase in pH or the basicity of the aqueous medium. The zeta potential of MFSNP-NH$_2$ changes from positive to negative at pH=7 when it reacts with BSA, thus providing further evidence for the formation of MFSNP-BSA.

Figure 9:
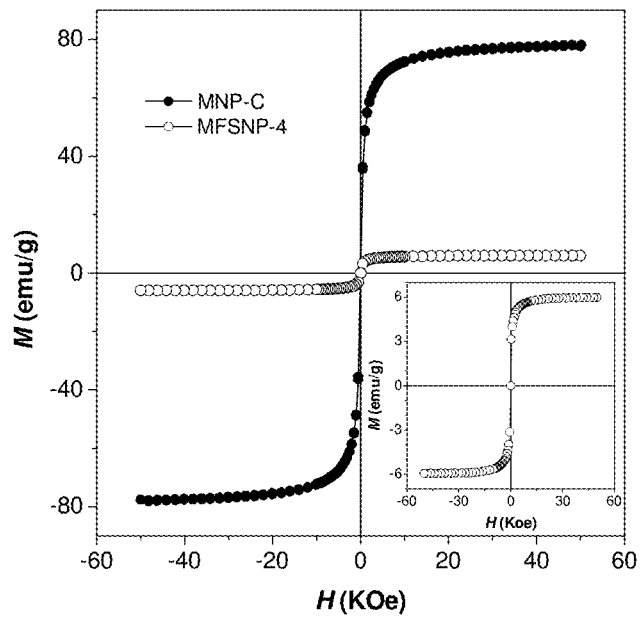
FIG. 9 illustrates the plots of magnetization versus applied magnetic field at 300 K for MNP-C and MFSNP-4 and the enlarged spectrum of MFSNPs.

FIG. 9 depicts the magnetization curves of the nanoparticles. With an increase in the magnetic field strength, the magnetization of MNP-C swiftly increases and ultimately reaches a saturation magnetization ($M_s$) of 78 emu g$^{-1}$. There is no hysteresis and both remanence and coercivity are zero, consistent with the superparamagnetic behaviors of the particles with nanoscale dimension. The magnetization curve of MFSNP-4 is similar to MNP-C. Although the $M_s$ value (6 emu g$^{-1}$) is much lower than MNP-C, it is already superior to those particles prepared previously with $M_s$ values in the range from 10$^{-6}$ to 1 emu g$^{-1}$. The low magnetization of MFSNPs is, in some sense, understandable because the magnetite nanoparticles are covered by a thick silica shell, which has significantly diminished the inductive effect of the magnetic field.

Figure 10:
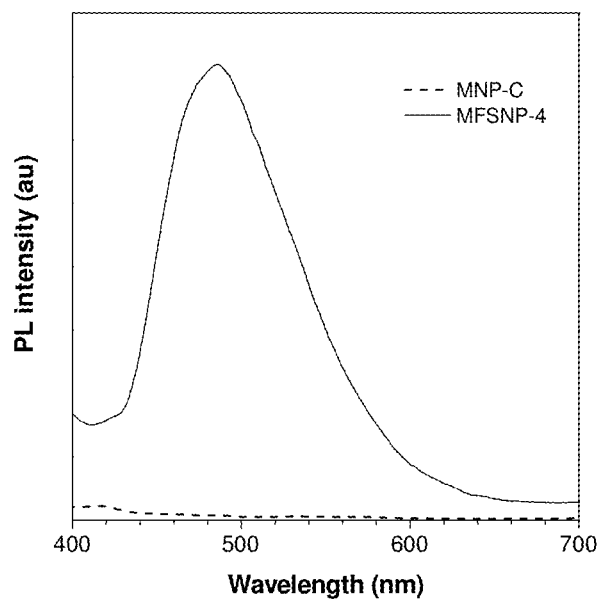
FIG. 10 illustrates the PL spectra of MNP-C and MFSNP-4 in ethanol solutions with concentrations of 100 μg/mL at an excitation wavelength of 370 nm.
Figure 11:
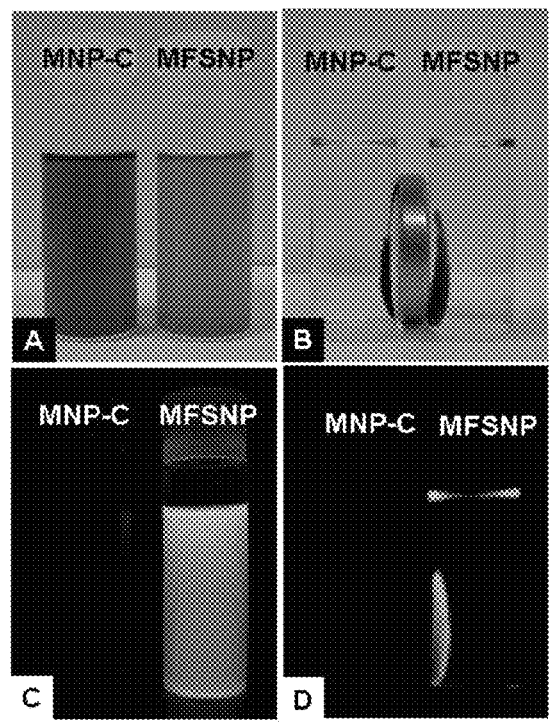
FIG. 11 shows photographs of ethanol solutions of MNP-C and MFSNP-4 taken under normal room lighting and UV illumination in the absence and presence of an external magnetic field from a bar magnet.

The light-emitting properties of the nanoparticles are investigated on a photoluminescence (PL) spectrometer. FIG. 10 shows the photoluminescence (PL) spectra of suspensions of MNP-C and MFSNP-4 in ethanol solutions. Nearly no fluorescence signals are recorded when MNP-C is photoexcited. Strong PL is, however, recorded at 486 nm in MFSNP-4 under the same measurement conditions. It is noteworthy that the silole-APS conjugate (7) is nonemissive in ethanol because the active intramolecular rotations of its phenyl blades have effectively annihilated the excited states, thus rendering the molecule nonluminescent. When the silole-APS conjugate (7) is covalently incorporated into and aggregated in the rigid silica network, its intramolecular rotations are restricted, which blocks the nonradiative relaxation channels and promotes the radiative decay of the excitons, thus making the MFSNP-4 emissive. The fluorescence quantum yield of MFSNP-4 measured by integrating sphere is reasonably high (7.11%), taking into the account that a low luminogen loading is used for the particle fabrication and the presence of iron species in MFSNP-4. The light emission is very stable, with no change in the spectrum detectable after the MFSNP-4 have been put on shelves for several months without protection from light and air. The photographs in FIG. 11 show that both MNP-C and MFSNP-4 exhibit good dispersion in solutions and can be attracted by a bar magnet. Although the solution of MNP-C emits no light upon UV irradiation, strong green PL is observed in MFSNP-4.

Example 3

Cell Imaging

HeLa cells were cultured in minimum essential medium containing 10% fetal bovine serum and antibiotics (100 units/mL penicillin and 100 μg/mL streptomycin) in a 5% CO$_2$ humidity incubator at 37° C. HeLa cells were grown overnight on a plasma-treated 25 mm round cover slip mounted onto a 35 mm petri dish with an observation window. The living cells were stained with 250 μL of MFSNPs and incubated for 24 h. The cells were imaged under an inverted fluorescence microscope (Nikon Eclipse TE2000-U); ex=330-380 nm, diachronic mirror=400 nm. The images of the cells were captured using a digital CCD camera.

Figure 12:
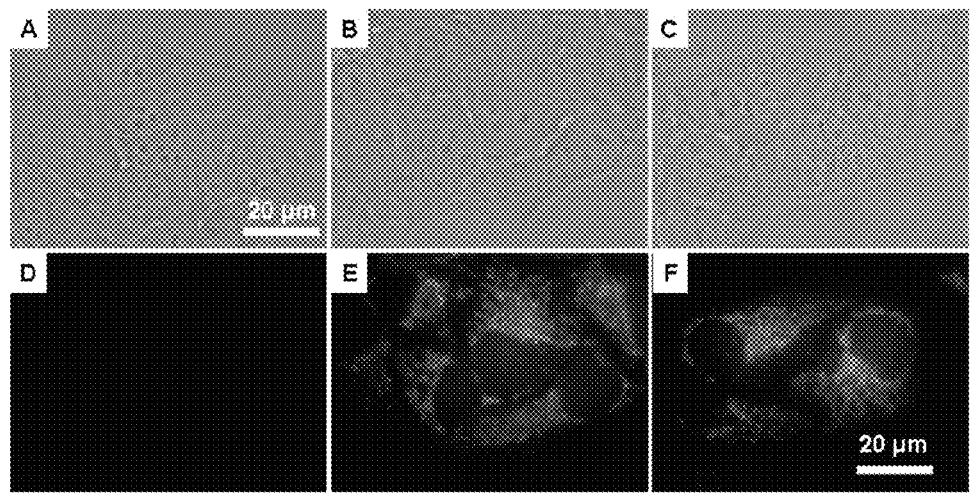
FIG. 12 illustrates the bright-field and fluorescent images of HeLa cells before and after labelled with MFSNP-4 and MFSNP-NH$_2$.
Figure 13:
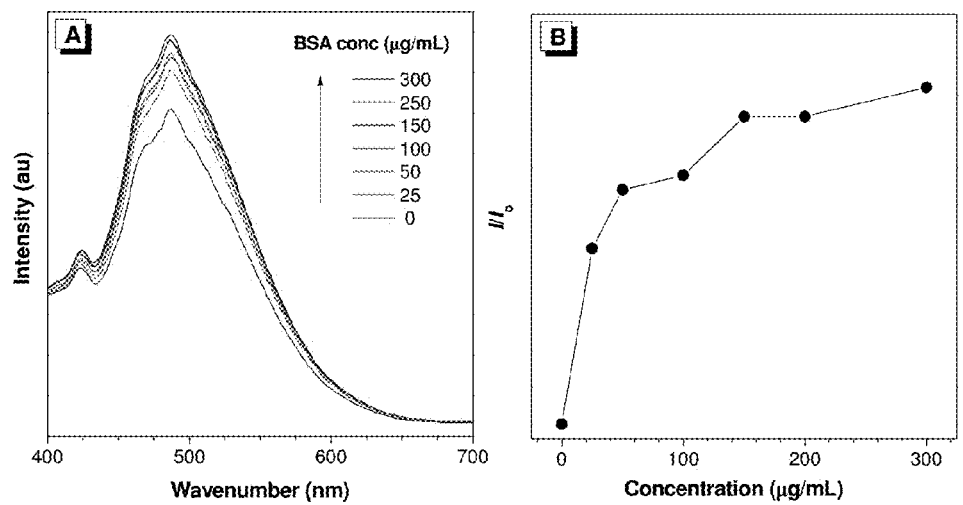
FIG. 13 illustrates the fluorescence spectra of PBS solutions of MFSNP-4 with different concentrations of BSA at room temperature and plot of ($I/I_o$) values versus the BSA concentrations in the solutions. Concentration of MFSNP-4: 500 μg/mL; excitation wavelength: 370 nm.

As illustrated by the photographs in FIG. 12, MFSNP-4 and MFSNP-NH$_2$ can work as fluorescent visualizers for intracellular imaging. Since the untreated HeLa cells emit no fluorescence upon UV irradiation, the bright green emissions observed in FIGS. 12E and 12F clearly originate from MFSNP-4 and MFSNP-NH$_2$. The major route for the nanoparticles to enter the HeLa cells is through endocytosis and such a process is facilitated by high positive surface charges due to the electrostatic attraction with the anionic cell membrane (the zeta potential of HeLa cell membrane is reported to be −50 mV). This is experimentally proved by flow cytometry, which can determine the nanoparticle uptake by the cells. Due to the contribution from the amino groups on the surface, MFSNP-4 and MFSNP-NH$_2$ exhibit reasonably high positive charges at pH=7, which may assist their uptake by the HeLa cells. The nanoparticles are then enclosed by the cell membrane to form small vesicles, which are then internalized by the cells. The nanoparticles are further processed in endosomes and lysosomes and are eventually released into the cytoplasm. When bound to the biomolecules, the nanoparticles may emit more intensely because the intramolecular rotations of the luminogens on the particle surface are further restricted. To confirm this, BSA solutions in PBS were prepared with various concentrations. After incubation with 500 μg mL$^{-1}$ MFSNP-4 for 4 h at room temperature, the emissions of the solutions were investigated. As depicted in FIG. 13, the fluorescence intensity increases with an increase in the BSA concentration and is saturated at high protein concentrations. Although the silica shell is hydrophilic, no MFSNP-4 are found in the nucleus, probably due to their sizes, which are still too big to pass through the nuclear membrane.

Figure 14:
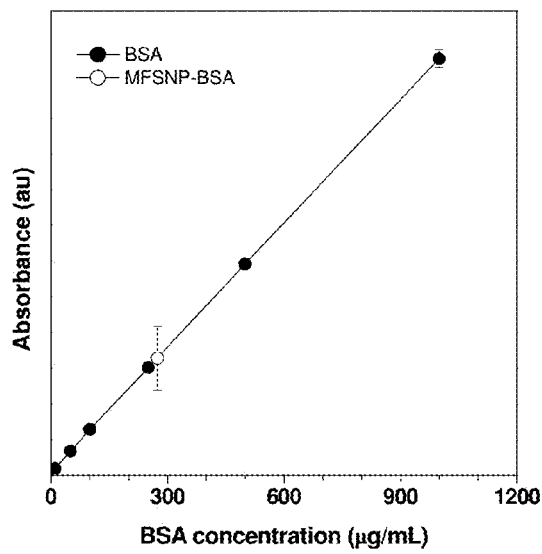
FIG. 14 illustrates the calibration curve for the determination of BSA concentration in MFSNP-BSA.

Since MFSNP-NH$_2$ is magnetic and shows a high surface charge, MFSNP-NH$_2$ possesses the capability to hold BSA molecules. A series of BSA solutions in phosphate-buffered saline (PBS) with known concentrations were prepared. The same amount of MFSNP-NH$_2$ was added to each solution. After incubation at room temperature for 1 h, particles of MFSNP-BSA formed and were separated by a bar magnet. MFSNP-BSA was washed with PBS and water and dispersed in PBS. FIG. 14 shows a calibration curve of absorbance versus BSA concentration. The amount of BSA in MFSNP-BSA was determined from the absorbance. For 5 mg of MFSNP-NH$_2$, it can adsorb 274 μg of BSA. Thus, MFSNPNH$_2$ can be used as a protein carrier or reactant for separating pure proteins from lysates.

Example 4

Synthesis of Tetraphenylethene-Containing Siloxane (18)

Tetrahydrofuran (THF) was purchased from Labscan and purified by simple distillation from sodium benzophenone under nitrogen immediately prior to use. 4-bromobenzophenone (13), 1,3-dicyclohexylcarbodiimide (DCC), 4-dimethylaminopyridine (DMAP), dimethylsulfoxide (DMSO), 1-hydroxypyrrolidine-2,5-dione (16), APS, TEOS and the other reagents were purchased from Aldrich and used as received. IR spectra were collected by a Perkin-Elmer 16 PC FTIR spectrophotometer (using the KBr method) operating at 4 cm$^{-1}$ resolution and 4 scans. $^1$H and $^{13}$C NMR spectra were recorded on a Bruker ARX 400 spectrometer with tetramethylsilane (TMS; δ=0) as the internal standard. The sizes and morphologies of the fluorescent silica nanoparticles (FSNPs) were investigated using JOEL 2010 TEM and JOEL 6700F SEM at an accelerating voltage of 200 and 5 kV.

The synthesis of tetraphenylethene (TPE)-containing siloxane (18) and its utilization for the fabrication of fluorescent silica nanoparticles (FSNPs) is shown in the chemical reaction scheme, below.

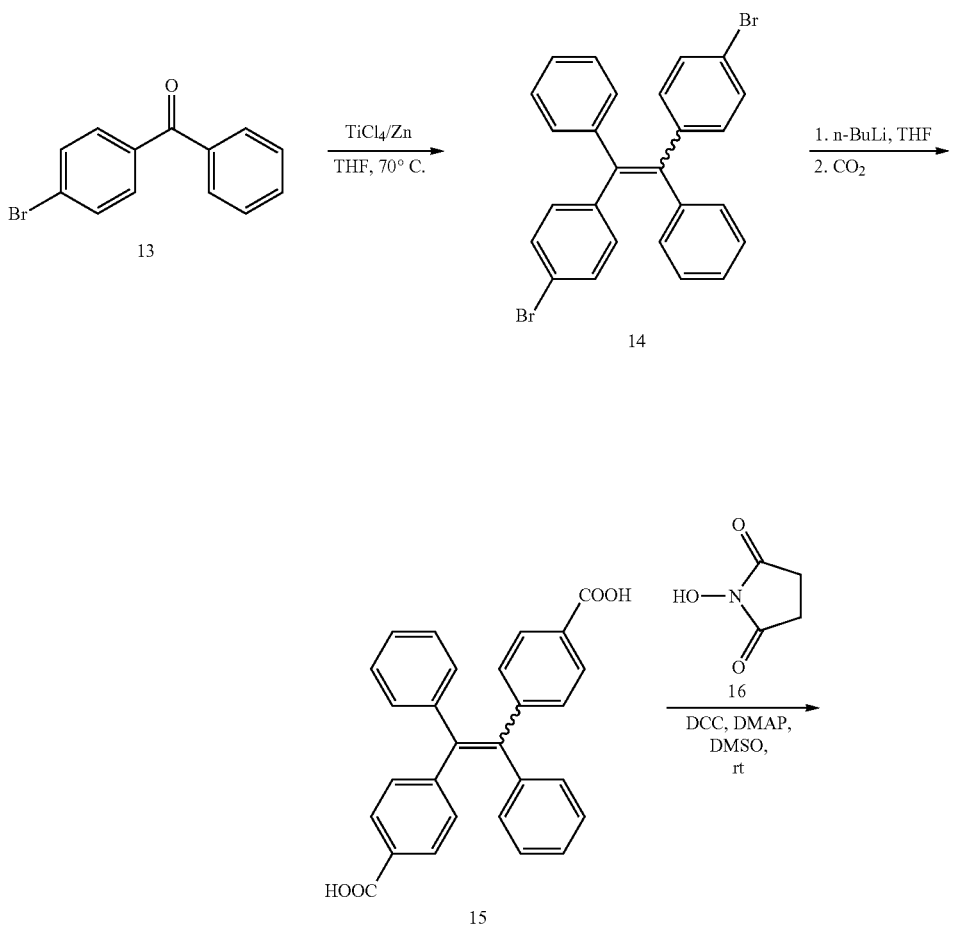

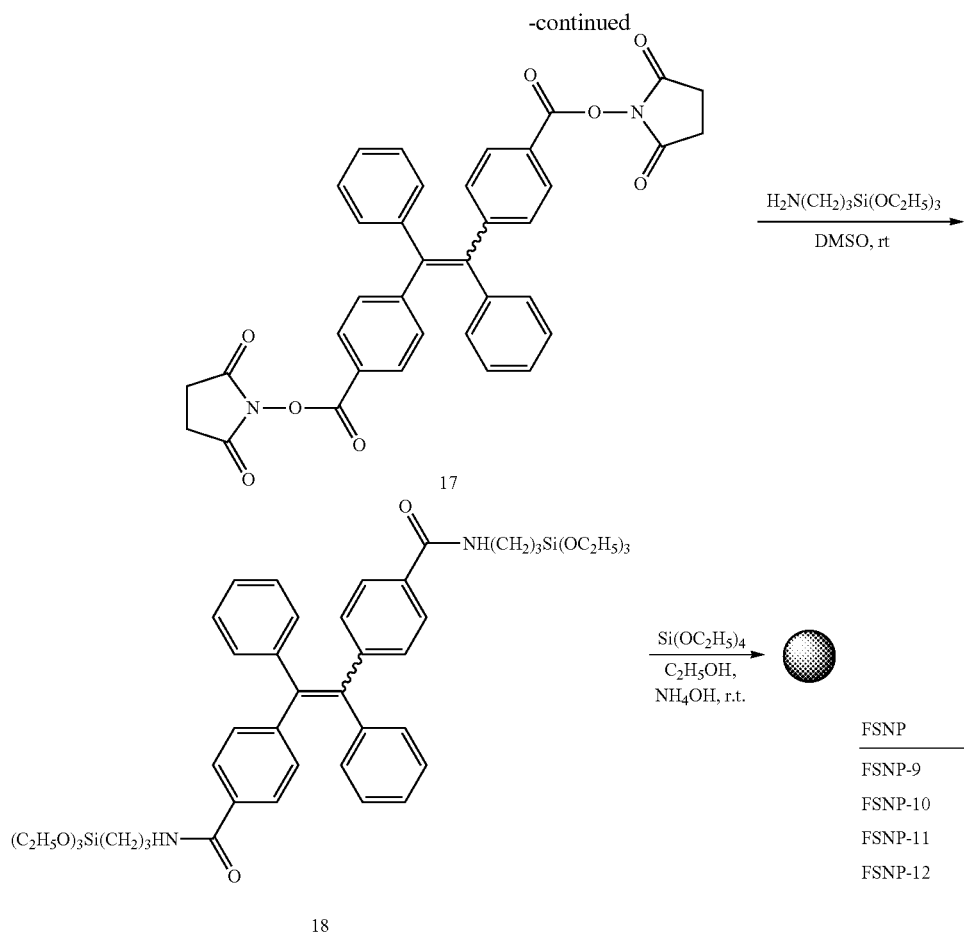

| FSNP | [18] (μmol) | stirring speed (rpm) |
|---|---|---|
| FSNP-9 | 12 | 700 |
| FSNP-10 | 12 | 1000 |
| FSNP-11 | 12 | 1700 |
| FSNP-12 | 24 | 1000 |

Synthesis of
1,2-Bis(4-bromophenyl)-1,2-diphenylethene (14)

1.97 g (30 mmol) of zinc dust and 3.92 g (15 mmol) of 4-bromobenzophenone (13) were placed into a 250 mL two-necked round-bottom flask with a reflux condenser. The flask was evacuated under vacuum and flushed with dry nitrogen three times. Then 100 mL of THF was added. The mixture was cooled to 0-5° C. and 1 mL (9 mmol) of $TiCl_4$ was slowly added. The mixture was slowly warmed to room temperature, stirred for 0.5 h, and refluxed overnight. The reaction was quenched with a 10% aqueous potassium carbonate solution and a large amount of water was added until the solid turned grey or white. The mixture was extracted with dichloromethane three times and the collected organic layer was washed with brine twice. The mixture was dried over 5 g of anhydrous sodium sulfate for 4 h. The crude product was condensed and purified on a silica-gel column using chloroform/hexane (1:5 by volume) as eluent. White solid; yield 94.61%. $^1$H NMR (400 MHz, $CDCl_3$), δ(TMS, ppm): 7.19-7.24 (m, 2H), 7.08-7.13 (m, 8H), 6.98-7.0 (m, 4H), 6.85-6.89 (m, 4H). $^{13}$C NMR (100 MHz, $CDCl_3$), δ (TMS, ppm): 142.87 (aromatic carbons connected to Br), 142.34, 140.23, 132.85, 131.17, 127.98, 127.78, 126.90, 120.74.

Synthesis of 4,4'-(1,2-Diphenylvinylene) dibenzoic acid (15)

1 g (2.04 mmol) of 4-bromobenzophenone (13) was dissolved in 20 mL of distilled THF in a 100 mL flask and the flask was placed in an acetone-dry ice bath at −78° C. A solution of 0.56 mL (6.12 mmol) of n-butyllithium (2.5 M in hexane) was added slowly to the mixture under stirring. The solution was transferred to a 500 mL flask containing dry ice. The resultant mixture was stirred overnight under nitrogen at room temperature. After solvent evaporation, potassium hydroxide solution was added and the aqueous solution was extracted with diethyl ether several times. The aqueous solution was acidified by adding 3 M hydrochloric acid and extracted with ethyl acetate. The organic layer was dried over magnesium sulphate and gave the desirable product in a yield of 35.96%. $^1$H NMR (300 MHz, acetone-$d_6$), δ(ppm): 7.99-7.93 (m, 3H), 7.50-7.46 (m, 1H), 7.35-7.28 (m, 9H), 7.25-7.16 (m, 4H), 7.15-7.10 (m, 1H). $^{13}$C NMR (75 MHz, acetone-$d_6$), δ (TMS, ppm): 166.1, 147.8, 142.4, 142.3, 141.1, 132.6, 130.7, 130.5, 128.8, 128.4, 127.6, 127.3, 126.7, 126.3, 120.0. HRMS (MALDF-TOF): m/e 403.14 [(M−OH)$^+$ calcd 403.14).

Synthesis of Tetraphenylethene-Containing Siloxane (18)

About 5.05 mg (12 μmol) of 4,4'-(1,2-Diphenylvinylene) dibenzoic acid (15), 2.9 mg (25 μmol) of 1-hydroxypyrrolidine-2,5-dione (16), 25 mg (96 μmol) of DCC, 0.67 mg (6 μmol) of DMAP were dissolved in 0.50 mL of DMSO in a 25 mL round-bottom flask. After stirring at room temperature overnight, the solution was diluted with 1 mL of THF and centrifuged to remove the urea salt formed from the reaction. The solution was concentrated under reduced pressure and compound Bis(2,5-dioxopyrrolidin-1-yl) 4,4'-(1,2-diphenylvinylene)dibenzoate (17) was then reacted with 9.6 µL (40 µmol) of APS, generating tetraphenylethene-containing siloxane (18) as a fluorophore for the fabrication of FSNP-9 by a two-step sol-gel reaction.

Example 5

Fabrication of Fluorescent Silica Nanoparticles

Tetraphenylethene-containing siloxane (18) (12 µmol) was added into a mixture of 64 mL of ethanol, 1.28 mL of ammonium hydroxide and 7.8 mL of distilled water. The solution was stirred at room temperature for 15 min to generate TPE-silica nanocores. A mixture of 2 mL of TEOS in 8 mL of ethanol was then added dropwise into the mixture. The reaction was stirred at 700 rpm at room temperature for 24 h to coat the luminogenic nanocores with silica shells. After incubation, the mixture was centrifuged and FSNP-9 was redispersed in ethanol under sonication for 5 min. The process was repeated three times and then the FSNP-9 were dispersed in water for further experiments. Similarly, FSNP-10 and FSNP-11 were also prepared from tetraphenylethene-containing siloxane (18) under similar conditions but at higher stirring speed (1000 and 1700 rpm). Likewise, FSNP-12 was prepared under similar conditions at a higher luminogen concentration (24 µmol).

Figure 15:
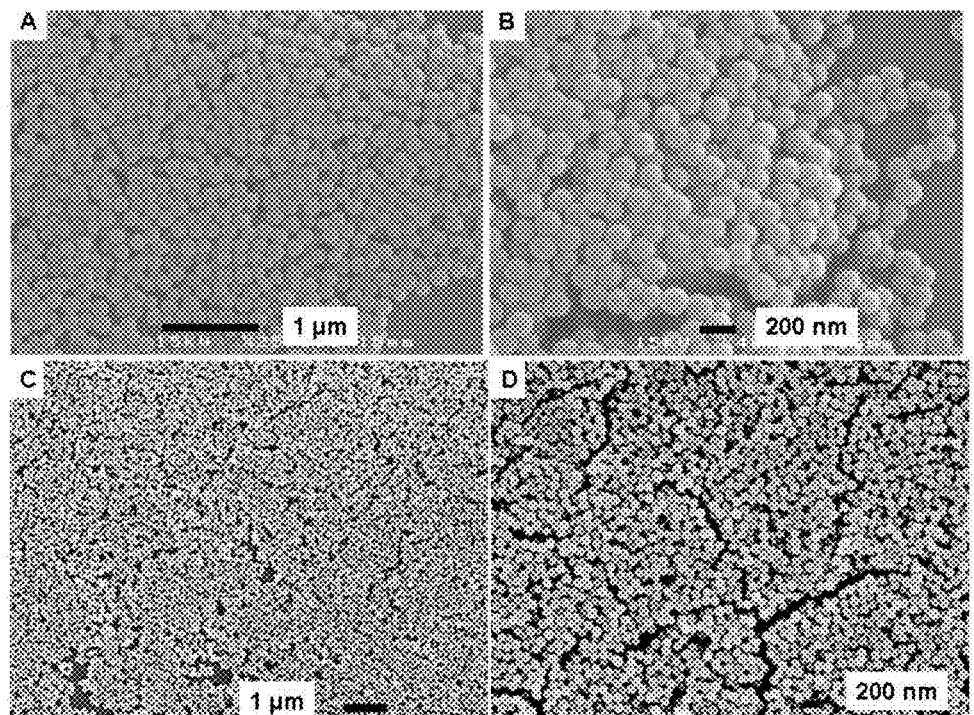
FIG. 15 shows the SEM micrographs of FSNP-10 and FSNP-11 at different magnifications.
Figure 16:
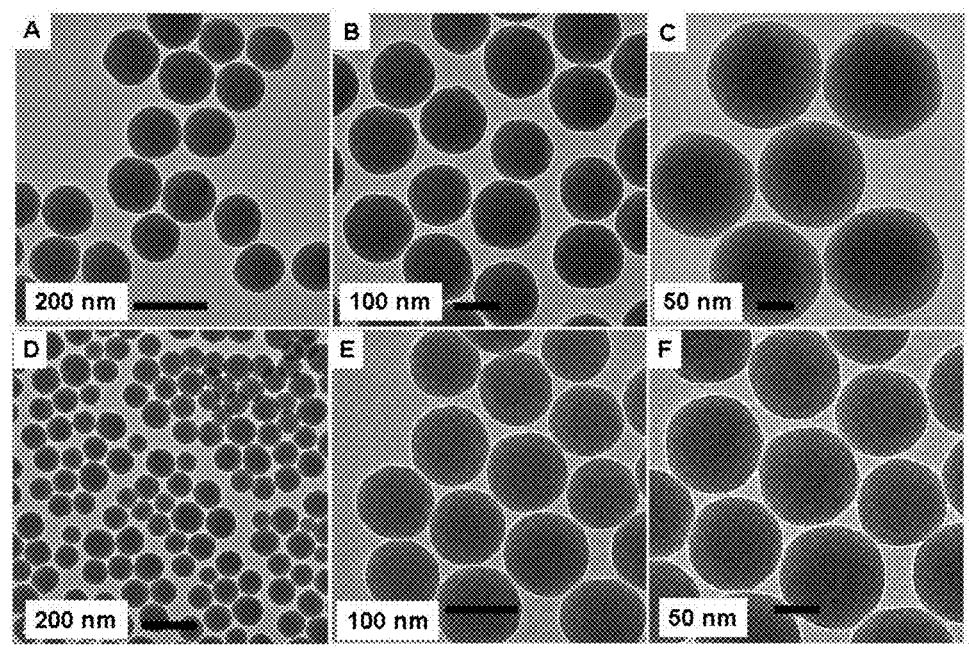
FIG. 16 shows the TEM micrographs of FSNP-10 and FSNP-11 at different magnifications with particle sizes of ~152.68±8.54 and 109.71±7.50 nm, respectively.
Figure 17:
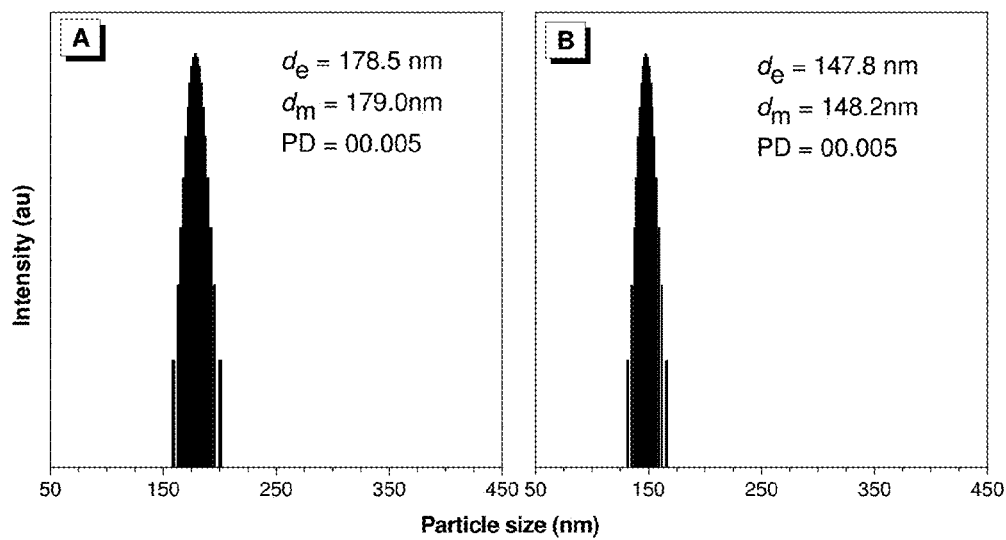
FIG. 17 shows the particle size distributions of FSNP-10 and FSNP-11. Abbreviation: $d_e$=effective diameter, $d_m$=mean diameter, PD=polydispersity.

The stirring speed during the sol-gel reaction greatly affects the size and distribution of the resultant FSNPs. FSNPs with uniform sizes can be achieved by either i) centrifuging the FSNPs at higher speed to separate the big particles from smaller ones or ii) adjusting a suitable stirring speed during the nanoparticle formation. For example, FSNP-9, obtained at a stirring speed of 700 rpm, displays bimodal particle growth and can be easily separated to monodispersed nanoparticles by centrifugation at 3000 rpm. When the stirring speed increases from 700 to 1000, and then to 1700 rpm, uniform, homogenous, and spherical-shaped FSNP-10 and FSNP-11 are obtained, as revealed by the scanning electron microscope (SEM) images shown in FIG. 15. Although their particle sizes are smaller than FSNP-9, the density remains the same because the same amount of TEOS is used for all the sol-gel reactions. At a higher stirring speed, more cores (primary nanoparticles) with uniform sizes are produced, whose further growth gives monodispersed FSNPs. The TEM images of FSNP-10 and FSNP-11 provide similar information as those of the SEM micrographs and show particles with smooth surfaces and sizes of 152.68±8.54 and 109.71±7.50 nm, respectively (FIG. 16). Similar values were also obtained from the zeta potential analyzer (179.0 nm for FSNP-10 and 148.2 nm for FSNP-11) with a polydispersity of 0.005 (FIG. 17).

Figure 18:
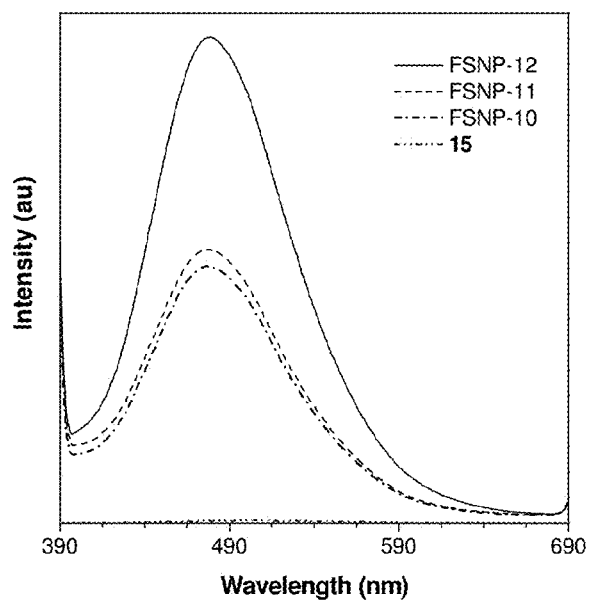
FIG. 18 shows the fluorescence spectra of 4,4'-(1,2-Diphenylvinylene)dibenzoic acid (15), FSNP-10, FSNP-11 and FSNP-12 in ethanol solutions. Concentration: 200 μg/mL; excitation wavelength: 353 nm.

FIG. 18 shows the fluorescence spectra of solutions of 4,4'-(1,2-Diphenylvinylene)dibenzoic acid (15) and suspensions of their core-shell nanoparticles FSNP-10, FSNP-11, and FSNP-12 in ethanol. The fluorescence spectrum of 4,4'-(1,2-Diphenylvinylene)dibenzoic acid (15) is almost a flat line parallel to the abscissa. In the dilute ethanol solution, the multiple peripheral phenyl rings in the isolated molecules of 4,4'-(1,2-Diphenylvinylene)dibenzoic acid (15) undergo active intramolecular rotations, which effectively consume the energy of their excited states and hence render them nonemissive. When the molecules of tetraphenylethene-containing siloxane (18) were covalently linked to the silica network, the fluorescence spectra peaked at 476 nm in FSNP-10, FSNP-11, and FSNP-12, confirming that tetraphenylethene-containing siloxane (18) is AIE-active. The rigid silica network largely restricts the intramolecular rotations of the luminogens. This blocks the nonradiative relaxation channel and populates the radiative excitons, thus making the FSNPs highly luminescent.

Figure 19:
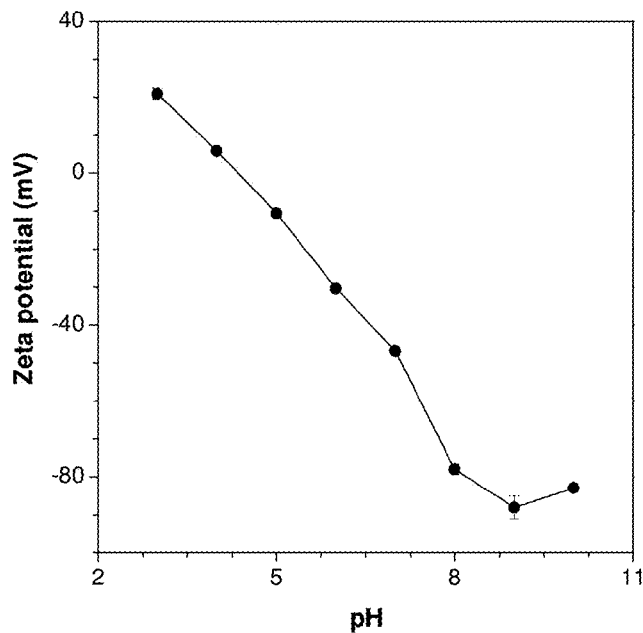
FIG. 19 shows the zeta potentials of FSNP-11 in aqueous media at different pH.

The surface charge of FSNP-11 in aqueous media with different pH was investigated by a zeta potential analyzer. The isoelectric point of FSNP-11 in water is observed at a pH value of ~4.2 (FIG. 19). Its zeta potential increases rapidly in an absolute term with increasing pH value. At pH 7, the zeta potential is as high as −46.86 mV, suggesting that the nanoparticles possess excellent colloidal stability. FSNP-11 exhibits positively-signed zeta potentials at pH below 4.2 due to the protonation of its silanol groups. At high pH, this event is less likely to occur but the dissociation of the silanol groups is favored. This explains why the zeta potential of the nanoparticles becomes negative and becomes higher in aqueous media with high pH or basicity.

Example 6

Fabrication of FSNPS by Thiol-Click Chemistry and Sol-Gel Reaction

3-Mercaptopropyltriethoxysilane (22), tetraethoxysilane (TEOS), and other chemicals and solvents were purchased from Aldrich and used without further purification. TPE and silole-containing diynes (21 and 24) were prepared according to literature methods (*J. Mater. Chem.* 2012, 22, 232 and *Macromolecules* 2010, 43, 4921). TPE and silole-functionalized siloxanes were synthesized by thiol-click chemistry according to the chemical reaction scheme, shown below.

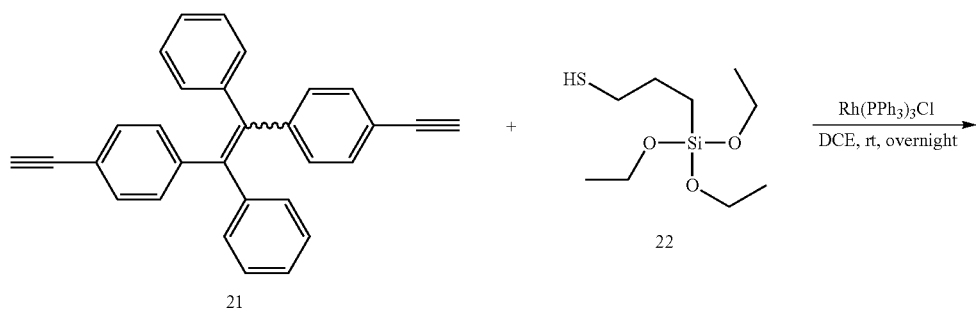

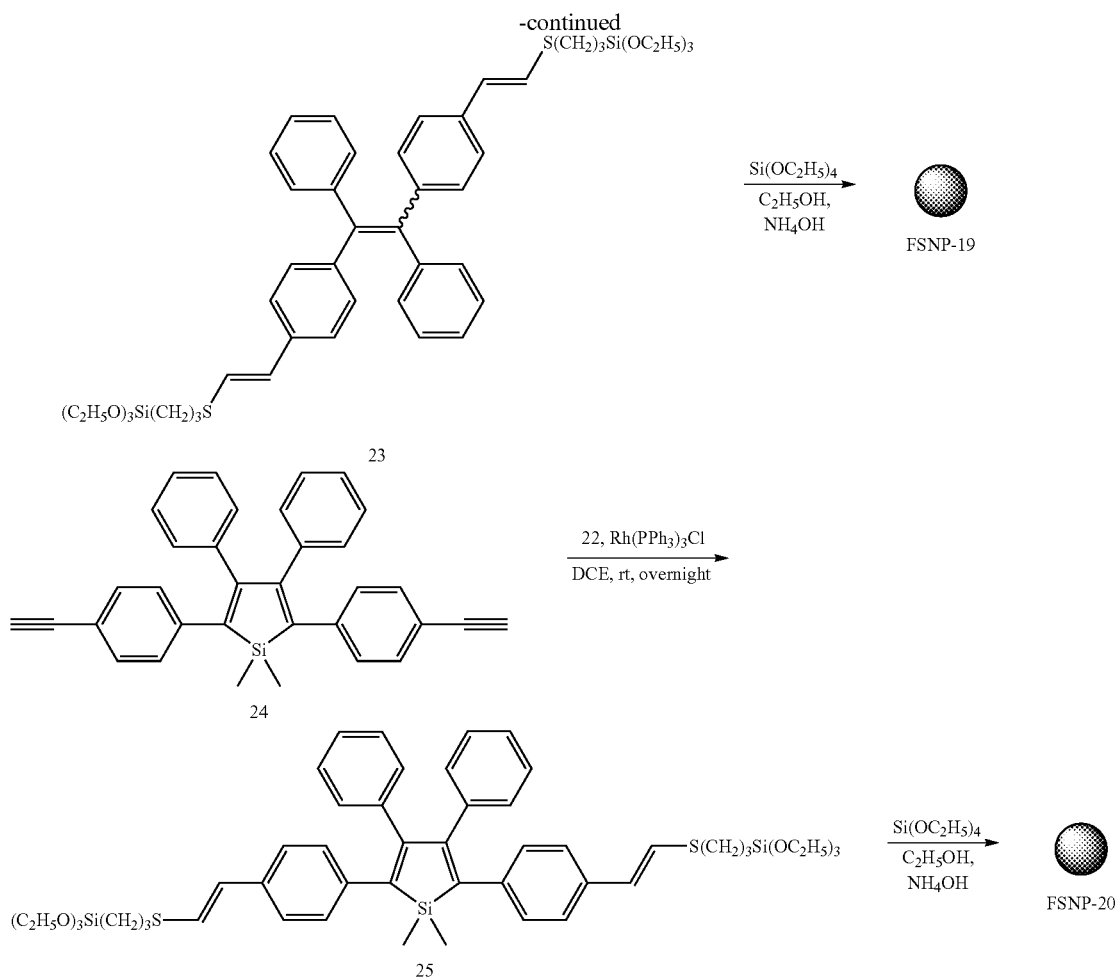

Synthesis of TPE-Containing Siloxanes (23)

5.7 mg (15 μmol) of TPE-containing diynes (21), 0.42 mg (0.45 μmol) of Rh(PPh$_3$)$_3$Cl, and 11.3 μL (37.5 μmol) of 3-Mercaptopropyltriethoxysilane (22) were added to 100 μL of dichloroethane (DCE) in a 5 mL round-bottom flask. Water was carefully excluded to avoid possible hydrolysis of 3-Mercaptopropyltriethoxysilane (22) and TPE-containing siloxanes (23). After stirring at room temperature for 24 h, the reaction mixture was concentrated under vacuum and the TPE-containing siloxanes (23) were characterized by mass spectroscopy.

Synthesis of Silole-Containing Siloxanes (25)

Similarly, silole-containing siloxanes (25) were prepared by alkyne hydrothiolation of silole-containing diynes (24) with 3-Mercaptopropyltriethoxysilane (22) and characterized by high-resolution mass spectroscopy. Adduct 23 was then used as a fluorophore to prepare FSNP-19 by a two step sol-gel reaction. Thus, the TPE-containing siloxanes (23) were first dissolved in DMSO and added into a mixture of ethanol (32 mL), ammonium hydroxide (0.64 mL), and distilled water (3.9 mL). The solution was stirred at room temperature for 1 h to prepare the fluorescent silica nanocores. A solution of TEOS (1 mL) in ethanol (4 mL) was then added drop-wise and the mixture was stirred at room temperature for 24 h to encapsulate the luminogenic nanocores with a silica shell. After incubation, the mixture was centrifuged and the FSNP-19 was redispersed in ethanol under sonication for 5 min. The process was repeated three times and then the FSNP-19 was dispersed in water. FSNP-20 was fabricated by sol-gel reaction of silole-containing siloxanes (25), catalyzed by ammonium hydroxide, followed by coating the resultant luminogenic nanocores with a silica shell.

Figure 20:
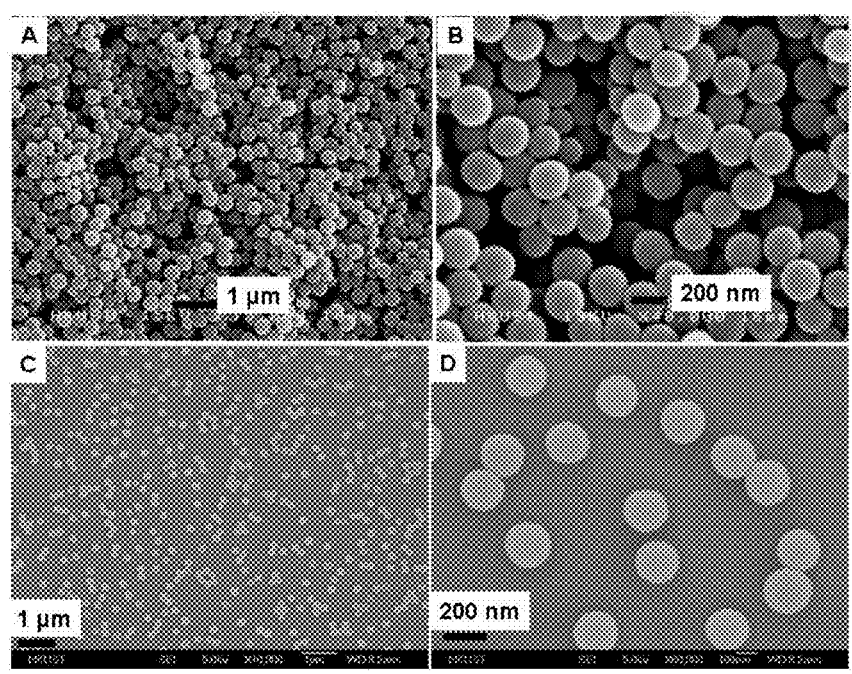
FIG. 20 shows the SEM micrographs of FSNP-19 and FSNP-20 at different magnifications.
Figure 21:
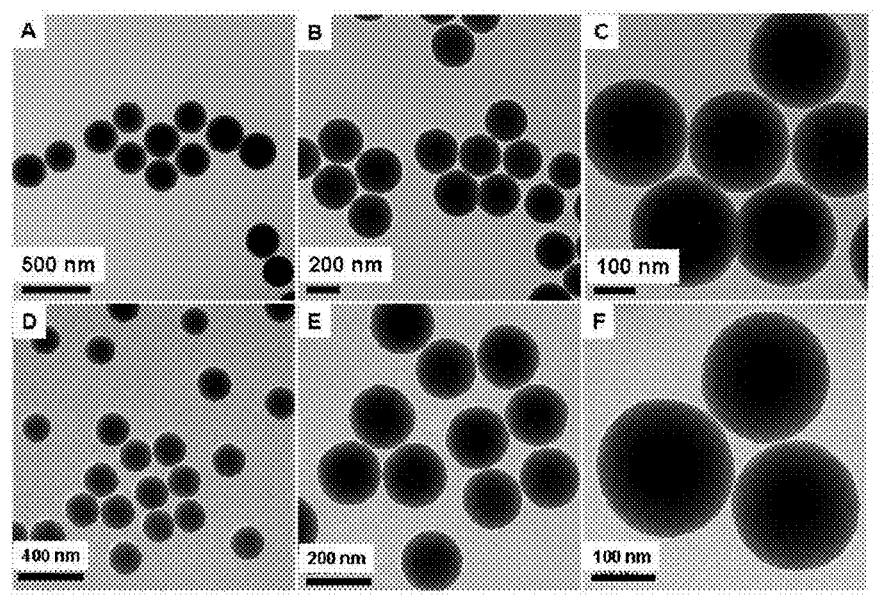
FIG. 21 shows the TEM micrographs of FSNP-19 and FSNP-20 at different magnifications with particle sizes of ~261.64±14.95 and 198.03±6.20 nm, respectively.
Figure 22:
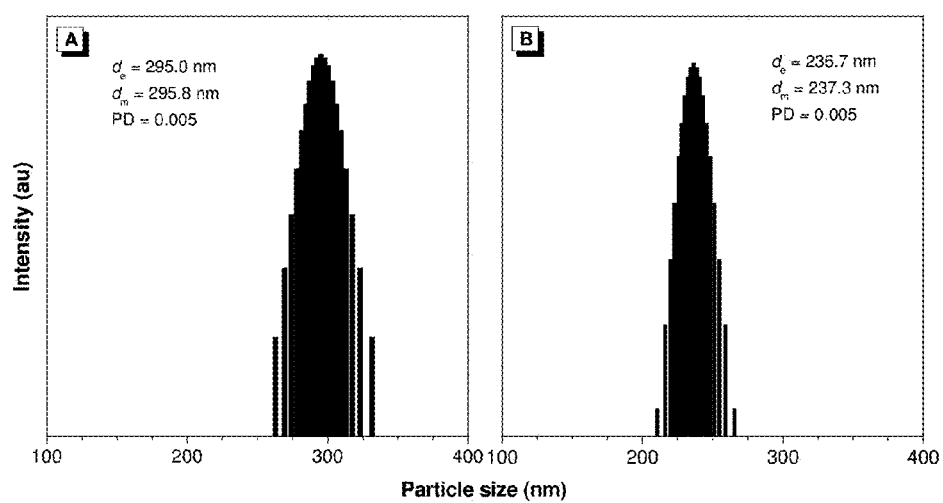
FIG. 22 shows the particle size distributions of FSNP-19 and FSNP-20.
Figure 23:
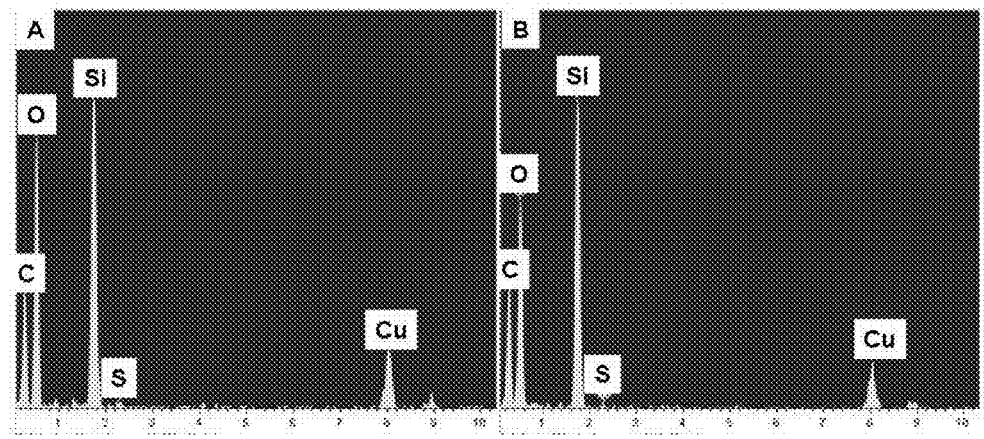
FIG. 23 shows the EDX spectra of FSNP-19 and FSNP-20.

The morphology of the FSNPs was investigated by SEM analysis. Both FSNP-19 and FSNP-20 showed discrete, spherical nanoparticles with uniform sizes and smooth surfaces (FIG. 20). Similarly, TEM measurements showed particle sizes of ~261.64±14.95 and 198.03±6.20 nm for FSNP-19 and FSNP-20, respectively (FIG. 21). Analysis by a zeta potential analyzer showed that both FSNPs are monodispersed with polydispersity down to 0.005 (FIG. 22). The average diameters of FSNP-19 and FSNP-20, estimated by the analyzer, were 295.8 and 237.3 nm, respectively. EDX measurement determined that both FSNP-19 and FSNP-20 contain the expected elements of carbon, oxygen, silicon, and sulfur (FIG. 23) and the breakdown of their chemical compositions are shown in Table 3, below. The silicon content of FSNP-20 is higher than FSNP-19. This is understandable due to the fine contribution from the silole unit.

TABLE 3

Chemical compositions of FSNP-19 and FSNP-20 determined by EDX analysis

| sample | carbon | oxygen | sulfur | silicon |
|---|---|---|---|---|
| FSNP-19 | 17.41 | 37.38 | 0.72 | 44.09 |
| FSNP-20 | 18.70 | 32.53 | 0.52 | 48.25 |

Figure 24:
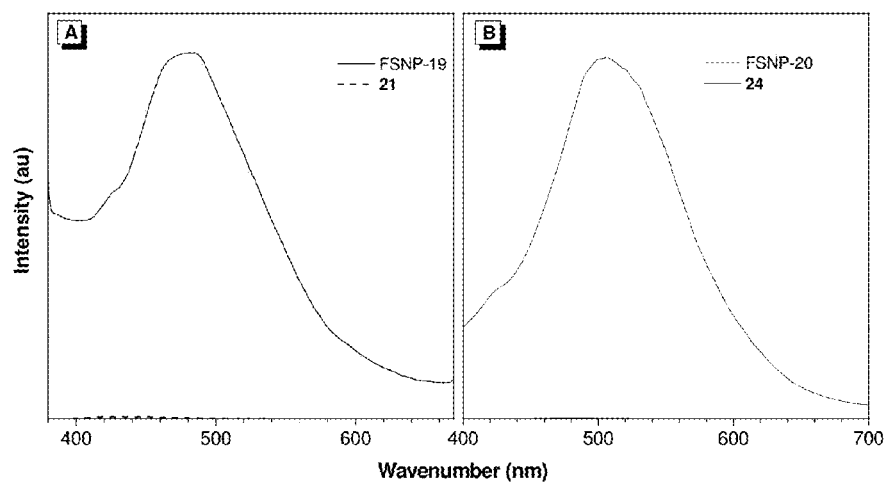
FIG. 24 shows the fluorescence spectra of FSNP-19, TPE-containing diynes (21), FSNP-20, and silole-containing diynes (24) in ethanol solutions. Concentration: 200 μg/mL.

FIG. 24 shows the fluorescence spectra of TPE-containing diynes (21), silole-containing diynes (24), FSNP-19, and FSNP-20 in ethanol solutions. The fluorescence spectra of TPE-containing diynes (21) and silole-containing diynes (24) are almost flat lines parallel to the abscissa. When they are incorporated into and aggregated in the silica network, the fluorescence spectra peaked at 480 and 506 nm in FSNP-19 and FSNP20, respectively. By dissolving TPE-containing diynes (21) and silole-containing diynes (24), and dispersing FSNP-19 and FSNP-20 with the same molar quantities of luminogens in ethanol, their emission intensities are compared. The light emissions from FSNP-19 and FSNP-20 are 225 and 401-fold stronger than those from TPE-containing diynes (21) and silole-containing diynes (24), respectively. The absolute fluorescence quantum yields of FSNP-19 and FSNP-20, determined by an integrating sphere, are 21.3 and 25.5%, respectively. These yields are reasonably high because only a low dye loading is used for their fabrication. The light emission is very stable, with no change in the fluorescence spectra detectable after the FSNPs have been put on shelves for several months without protection from light and air.

Finally, zeta potential analyses of the FSNPs were carried out to realize their surface charge and hence their colloidal stability in the suspension state. As shown in FIG. 25, the zeta potentials of FSNP-19 and FSNP-20 are low at low pH and increasing in absolute term with increasing pH. This trend shows that their surface charge is low in acidic media, but high in alkaline media. The zeta potentials of FSNP-19 and FSNP-20 at pH 7 are −37 and −32 mV, respectively, revealing that they have good colloidal stability.

Example 7

Synthesis of TPE and Silole-Containing Siloxanes by Click Chemistry

Tetraethoxysilane (TEOS), dimethylsulfoxide (DMSO), (3-chloropropyl)triethoxysilane, dimethylformamide (DMF), and tetrahydrofuran (THF) and other reagents were all purchased from Aldrich and used as received. IR spectra were collected by a Perkin-Elmer 16 PC FTIR spectrophotometer (using the KBr method) operating at 4 cm$^{-1}$ resolution and 4 scans. $^1$H and $^{13}$C NMR spectra were recorded on a Bruker ARX 400 spectrometer with tetramethylsilane (TMS; δ=0) as an internal standard.

5.0 mL or 5.0 g (20.85 mmol) of 3-chloropropyltriethoxysilane (30), 5 g (77 mmol) of sodium azide, and 50 mL of dry DMF were injected into a 100 mL two-neck round bottom flask. The solution was heated to 90° C. under nitrogen atmosphere for 5 h.

The low boiling materials were removed by distillation under reduced pressure (ca. 10 mm Hg), after which 100 mL of diethyl ether was added. The precipitated salts were removed by filtration and the solvent was removed under vacuum. Distillation of the residual oil under reduced pressure (2 mm Hg, 96° C.) produced 3-Azidopropyltriethoxysilane (31), a colorless liquid (3.3 g, 68%). $^1$H NMR (400 MHz, CDCl$_3$), δ(ppm): 3.81 (q, 6H), 3.24 (t, 2H), 1.66-1.70 (m, 2H), 1.21 (t, 9H), 0.66 (t, 2H). $^{13}$C NMR (100 MHz, CDCl$_3$), δ (ppm): 58.4, 53.8, 22.6, 18.2, 7.5. IR, ν (cm$^{-1}$): 2977, 2927, 2883, 2734, 2098, 1284, 1165, 1084, 960, 779. Click reactions of TPE-containing diynes (21) and silole-containing diynes (24) with 3-chloropropyltriethoxysilane (30) were carried under nitrogen using Schlenk tubes.

TPE and silole-containing siloxanes were synthesized by click chemistry as shown in the chemical reaction scheme, below.

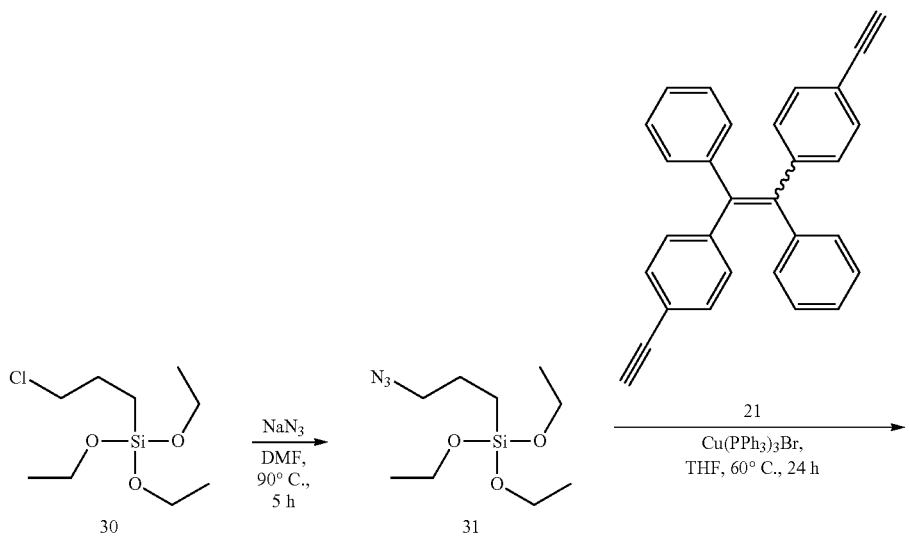

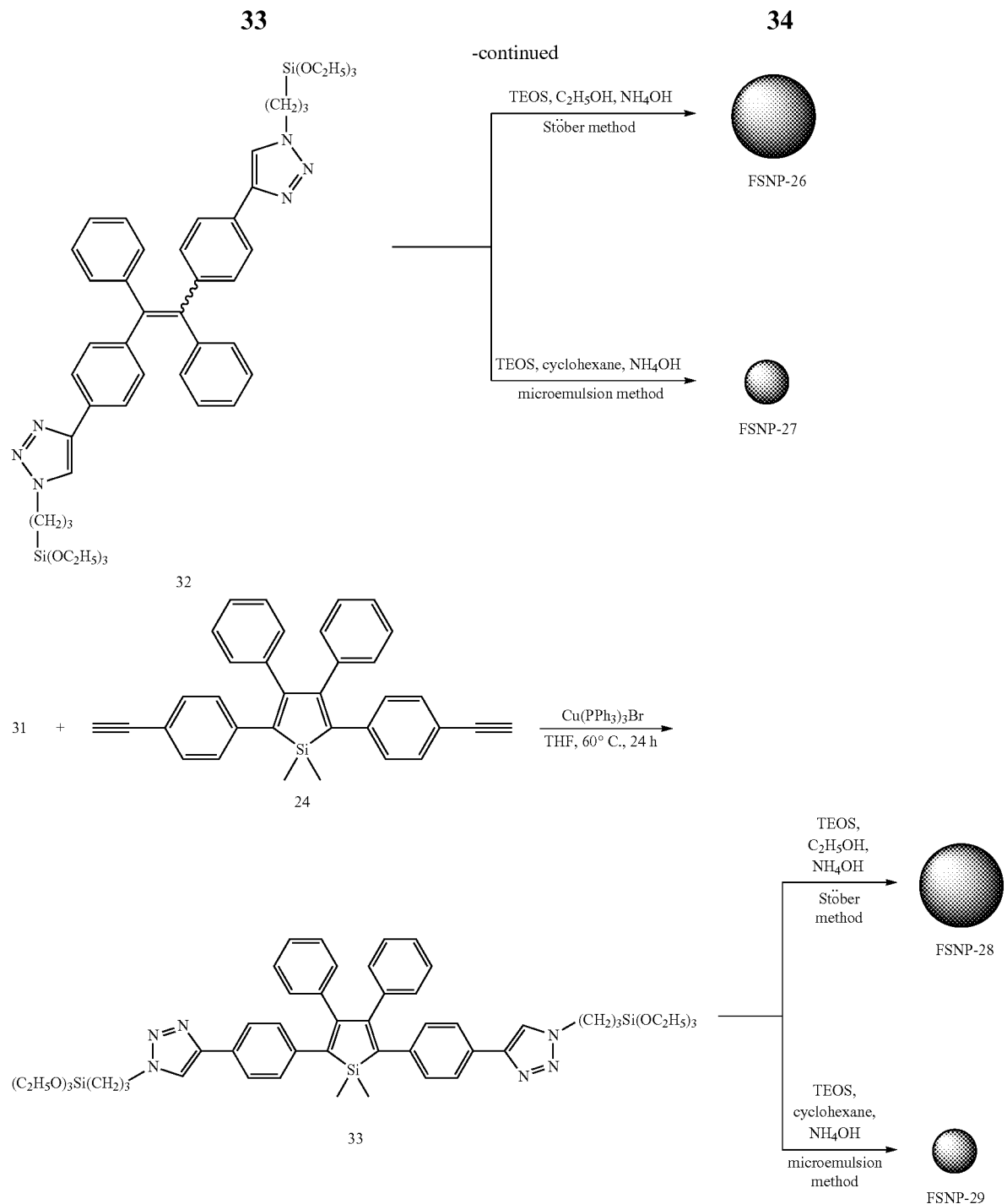

20.0 mg (0.081 mmol) of 3-Azidopropyltriethoxysilane (31), 15.4 mg (0.0405 mmol) of TPE-containing diynes (21), and 4.5 mg of Cu(PPh$_3$)$_3$Br were placed in a 15 mL Schlenk tube. Then, 2 mL of THF was injected into the solution. After stirring at 60° C. for 24 h, the reaction mixture was diluted with 3 mL of THF and centrifuged at 3000 rpm for 15 min. During the reaction, water was carefully excluded to avoid the possible hydrolysis of 3-Azidopropyltriethoxysilane (31) and 1,2-Bis(4-{1-[2-(triethoxysilyl)ethyl]-4-triazolyl}phenyl)-1,2-diphenylethene (32). The supernatant was decanted and concentrated and product 1,2-Bis(4-{1-[2-(triethoxysilyl)ethyl]-4-triazolyl}phenyl)-1,2-diphenylethene (32) was characterized by high resolution mass spectroscopy.

FIG. 26 shows that the reaction product gives an (M+1)+ peak at 875.4327 in its high-resolution mass spectrum (HRMS), thereby confirming the occurrence of the cycloaddition reaction and the formation of expected 1,2-Bis(4-{1-[2-(triethoxysilyl)ethyl]-4-triazolyl}phenyl)-1,2-diphenylethene (32) (M$^+$=874.4269).

2,5-Bis(4-{1-[2-(triethoxysilyl)ethyl]-4-triazolyl}phenyl)-3,4-diphenyl-1,1-dimethylsilole (33) was synthesized using similar procedures as described above. 20.0 mg (0.081 mmol) of 3-Azidopropyltriethoxysilane (31), 18.74 mg (0.0405 mmol) of silole-containing diynes (24), and 4.5 mg (6 mol %) of Cu(PPh$_3$)$_3$Br were dissolved in 2 mL of THF. After stirring at 60° C. for 24 h, the reaction mixture was diluted with 3 mL of THF and centrifuged at 3000 rpm for 15 min. The supernatant was decanted and concentrated and 2,5-Bis(4-{1-[2-(triethoxysilyl)ethyl]-4-triazolyl}phenyl)-3,4-diphenyl-1,1-dimethylsilole (33) was characterized by high resolution mass spectroscopy, as shown in FIG. 27.

Example 8

Preparation of FSNPs by Stöber Method

FSNP-26 was prepared from 1,2-Bis(4-{1-[2-(triethoxysilyl)ethyl]-4-triazolyl}phenyl)-1,2-diphenylethene (32) and TEOS by a two-step sol-gel reaction. About 15 μmol of 1,2-Bis(4-{1-[2-(triethoxysilyl)ethyl]-4-triazolyl}phenyl)-1,2-diphenylethene (32) were added into a mixture of ethanol (32 mL), ammonium hydroxide (0.64 mL), and distilled water (3.9 mL). The solution was stirred at room temperature for min, after which an ethanol solution (5 mL) of TEOS (1 mL) was added dropwise. The solution was stirred at room temperature for an additional 24 h to coat the luminogenic nanocores with silica shells. After incubation, the mixture was centrifuged and the nanoparticles of FSNP-26 were redispersed in ethanol under sonication for 5 min. The process was repeated three times and FSNP-26 was dispersed in water or ethanol for further experiments. Similarly, sol-gel reaction of 2,5-Bis(4-{1-[2-(triethoxysilyl)ethyl]-4-triazolyl}phenyl)-3,4-diphenyl-1,1-dimethylsilole (33) followed by reaction with TEOS furnished FSNP-28.

Example 9

Preparation of FSNPs by Microemulsion

Fluorescent silica nanoparticles (FSNP-27 and FSNP-29) were prepared according to the method in R. P. Bagwe, C. Yang, L. R. Hilliard, W. Tan, Langmuir 2004, 20, 8336. The micelles were prepared at room temperature by sonication of a homogenous mixture of cyclohexane (30 mL), Triton X-100 (7.2 mL), n-heptanol (5.6 mL), and water (600 μL) for 30 min. 800 μL of ammonia solution (28%) was then added. After magnetically stirring for 15 min, 100 μL of 1,2-Bis(4-{1-[2-(triethoxysilyl)ethyl]-4-triazolyl}phenyl)-1,2-diphenylethene (32) or 7.5 μmol of TPE-containing diynes (21) was injected. The solution was stirred for another 15 min. After drop-wise addition of 400 μL of TEOS, the reaction mixture was allowed to stir for 24 h at room temperature. The microemulsion reaction was terminated by adding ethanol and the nanoparticles were centrifuged and washed with ethanol and water to remove the surfactant. The nanoparticles were then dried in vacuum at room temperature. The nanoparticles of FSNP-27 were dispersed in deionized water or ethanol for further experiments.

Analysis by zeta potential analyzer at room temperature showed that all the FSNPs were monodispersed with low polydispersities down to 0.005 (FIGS. 28 and 29). The mean diameters of FSNP-26 and FSNP-28 are 185.7 and 255.6 nm, respectively. These figures are somewhat larger than those measured by TEM (143.37±10.5 and 217.26±20.4 nm for FSNP-26 and FSNP-28, respectively) due to the larger hydrodynamic diameters of the FSNPs in aqueous mixtures and shrinkage of the same under the high electron-beam intensity in the TEM chamber. EDX measurement shows that the FSNPs contain the expected elements of carbon, nitrogen, oxygen, and silicon. Examples of the EDX spectra of FSNP-26 and FSNP-28 are provided in FIG. 30 and Table 4, below, summarizes the make-up of the compositions.

TABLE 4

| Chemical compositions of FSNP-26 and FSNP-28 determined by EDX analysis | | | | |
|---|---|---|---|---|
| Sample | Carbon | Nitrogen | Oxygen | Silicon |
| FSNP-26 | 3.23 | 1.07 | 39.18 | 56.52 |
| FSNP-28 | 4.28 | 0.68 | 41.17 | 53.86 |

It is important to tune the sizes of nanoparticles to meet the requirements of different technological applications. The Stöber and reverse microemulsion methods give large- and small-sized FSNPs, respectively. Actually, the sizes of the nanoparticles can also be tuned by varying the reaction parameters. Larger nanoparticles are obtained by using higher concentrations of TEOS and ammonium hydroxide and vice versa. TEM images show that the large-sized FSNPs possess smooth surfaces, while the surfaces of the small nanoparticles (i.e., FSNP-27 and FSNP-29) are somewhat rough (FIG. 31 and FIG. 32). Analyses by SEM also gave similar results (FIG. 33 and FIG. 34). The mean diameters of FSNP-27 and FSNP-29, determined by TEM, are ~37.68±2.7 and 59.82±4.1 nm, respectively, thus proving that the reverse microemulsion method does indeed generate FSNPs with much smaller sizes than those prepared by the Stöber technique in a controlled fashion.

The fluorescence spectra of TPE-containing diynes (21), silole-containing diynes (24), and the suspensions of their core-shell nanoparticles FSNP-26 and FSNP-28 in ethanol are shown in FIG. 35. There are barely fluorescence signals when the solutions of TPE-containing diynes (21) and silole-containing diynes (24) are photoexcited. However, the fluorescence spectra peaked at 474 and 489 nm in FSNP-26 and FSNP-28, respectively. By dissolving TPE-containing diynes (21) and silole-containing diynes (24), and dispersing FSNP-26 and FSNP-28, fabricated by using the same molar quantities of luminogens (i.e., 32 and 33) in ethanol, their emission intensities are compared. The light emission from FSNP-26 and FSNP-28 is 1010 and 916-fold higher than those of FSNP-9 and FSNP-10, respectively. The absolute fluorescence quantum yields ($\Phi_{F,abs}$) of FSNP-26 and FSNP-28, determined by integrating spheres, are 33.4 and 38.2%, respectively.

Colloidal stability is an important parameter for FSNPs and can be reflected by their surface charges or zeta potentials. FSNPs are said to be colloidally stable if their surface charges are high at the workable pH because strong electrostatic repulsion will exist between the nanoparticles. The functional groups play an important role in determining the surface charges of the FSNPs. In our previous work, we reacted brominated TPE and silole with APS and used the adducts as fluorescent cores for the fabrication of highly emissive and monodispersed FSNPs (*Chem. Eur. J.* 2010, 16, 4266). Their charges at neutral pH are, however, not high enough to impart high colloidal stability. This is due to the presence of free amine groups on the surface, which partially counteract the negative charge contributed by the silanol groups. Similarly, FSNPs with thiourea linkages obtained by reaction of isothiocyanated dye molecules with APS possess even lower colloidal stability and precipitate in ethanol and water at pH≥7. 1,2-Bis(4-{1-[2-(triethoxysilyl)ethyl]-4-triazolyl}phenyl)-1,2-diphenylethene (32) and 2,5-Bis(4-{1-

[2-(triethoxysilyl)ethyl]-4-triazolyl}phenyl)-3,4-diphenyl-1,1-dimethylsilole (33) are synthesized from 3-Azidopropyltriethoxysilane (31) instead of APS. Accordingly, FSNPs fabricated from these compounds show high surface charges. As shown in FIG. 36, FSNP-26 and FSNP-28 exhibit reasonably high zeta potentials even at pH 3. With an increase in the pH value or the solution basicity, their potentials become higher or more negative because the dissociation of the surface silanol groups is favorable in such media.

One of the important areas in which FSNPs have demonstrated great potential is in cancer cell imaging. Luminogens with aggregation-induced emission (AIE) characteristics are benign to the growth of living cells (Chem. Eur. J. 2010, 16, 4266). They are also nontoxic to HeLa cells and interfere little with the cytoplasmic activities of the cells. To examine the cell staining ability of the FSNPs, HeLa cells were cultured in the presence of these nanoparticles. After 6 h of incubation, the FSNPs were endocytosed through the cell membrane and efficiently anchored on the cytoplasmic organelles. To compare the uptake efficiency of FSNPs with different sizes, the cells were stained with FSNP-26 and FSNP-27. As depicted in FIG. 37, both FSNPs work as good fluorescent visualizers for intracellular imaging. On the contrary, the images of HeLa cells stained by FSNP-28 and FSNP-29 show different brightness, albeit to a small extent (FIG. 38). During the endocytosis, the FSNPs are enclosed by the cell membrane to form small vesicles, which are then internalized in the cytoplasmic compartment of the cell. The FSNPs are further processed in the endosomes and lysosomes containing numerous digestive enzymes and are eventually released to the cytoplasm. When bound to the biomacromolecules, the FSNPs may emit even more intensely because their intramolecular rotations are further restricted if some of them are located on the surface. Although the silica shells are hydrophilic, no fluorescence is observed in the cell nucleus, probably due to the "large" particle sizes of the FSNPs.

Example 10

Synthesis of TPE-Containing Diyne

Tetraethoxysilane (TEOS), 4-hydroxybenzophenone (35), 5-hexynoic acid (37), 1,3-dicyclohexylcarbodiimide (DCC), 4-(dimethylamino)pyridine (DMAP), p-toluenesulfonic acid (TsOH), 3-bromopropyltrichlorosilane, and other reagents were all purchased from Aldrich and used without further purification. IR spectra were obtained on a Perkin-Elmer 16 PC FTIR spectrophotometer. $^1$H and $^{13}$C NMR spectra were recorded on a Bruker ARX 400 spectrometer with tetramethylsilane (TMS; δ=0) as an internal standard. High resolution mass spectra (HRMS) were recorded on a Finnigan TSQ 7000 triple quadrupole spectrometer operating in a MALDI-TOF mode.

TPE-containing diyne (38) was synthesized according to the chemical reaction scheme, shown below.

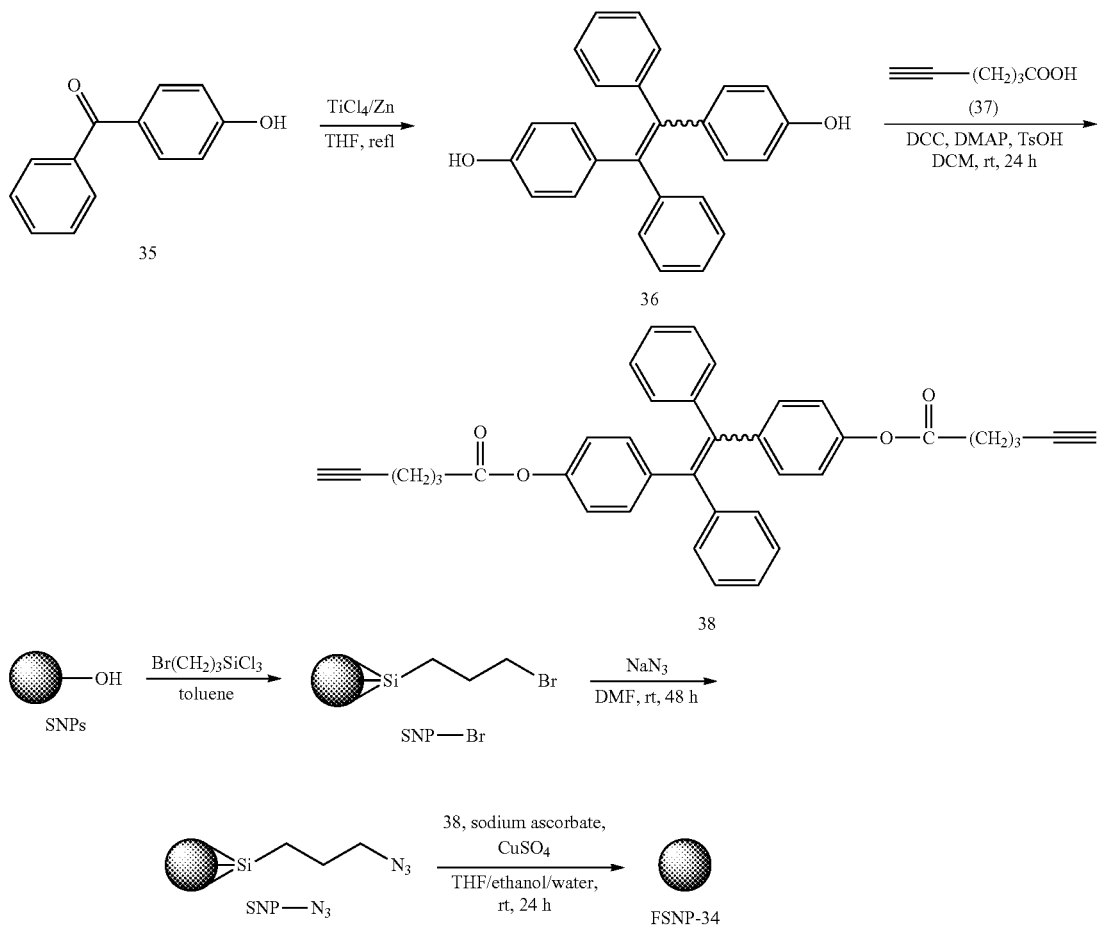

Synthesis of 1,2-Bis(4-hydroxyphenyl)-1,2-diphenylethene (36)

1.18 g (18 mmol) of zinc dust, and 2.97 g (15 mmol) of 4-hydroxybenzophenone (35) were placed into a 250 mL two-necked round-bottom flask equipped with a reflux condenser. The flask was evacuated under vacuum and flushed with dry nitrogen three times. 100 mL of THF was then added. The mixture was cooled to 0-5° C. and 1 mL (9 mmol) of $TiCl_4$ was slowly added. The mixture was slowly warmed to room temperature, stirred for 0.5 h, and then refluxed overnight. The reaction was quenched with 10% aqueous potassium carbonate solution and a large amount of water was added until the solid turned grey or white. The mixture was extracted with dichloromethane three times and the collected organic layer was washed twice with brine solution. The mixture was dried over 5 g of anhydrous sodium sulfate for 4 h. The crude product was condensed and purified on a silica-gel column using chloroform/hexane (1:5 by volume) as eluent. White solid; yield 90.2%. $^1H$ NMR (400 MHz, $CDCl_3$), δ (TMS, ppm): 7.03-7.12 (m, 10H), 6.90 (t, 4H), 6.57 (d, 4H). $^{13}C$ NMR (100 MHz, $CDCl_3$), δ (TMS, ppm): 154.13 (aromatic carbons connected to OH), 144.21, 139.67, 135.53, 132.79, 131.50, 127.76, 126.36, 114.72.

Synthesis of 4,4-(1,2-diphenylvinylene)diphenyl bis(5-hexynoate) (38)

1.82 g (5 mmol) of 1,2-Bis(4-hydroxyphenyl)-1,2-diphenylethene (36), 1.23 g (11 mmol) of 5-hexynoic acid (37), 2.48 g (12 mmol) of DCC, 244.3 mg (2 mmol) of DMAP, and 380.4 mg (2 mmol) of TsOH were placed in 100 mL of dichloromethane in a 250 mL one-necked round-bottom flask. The resultant mixture was stirred for 24 h at room temperature. After filtration of the urea salt formed during the reaction, the solid was washed with dichloromethane and the filtrate was concentrated by a rotary evaporator. The product was purified by a silica gel column using a mixture of chloroform/hexane (1:1 v/v) as eluent. A white solid of 4,4-(1,2-diphenylvinylene)diphenyl bis(5-hexynoate) (38) was obtained in 85.9% yield. IR (KBr), ν($cm^{-1}$): 3296 (HC≡C), 2118 (C≡C), 1756 (C═O). $^1H$ NMR (400 MHz, $CDCl_3$), δ (TMS, ppm): 7.13, 7.12, 7.11, 7.10, 7.09, 7.03, 7.02, 7.01, 7.0, 6.87, 6.85, 6.84, 6.82, (18H, aromatic protons), 2.66 (m, 2H, HC≡), 2.32 (m, 4H, $OCCH_2$), 2.0 (m, 4H, ≡$CCH_2$), 1.93 (m, 4H, $OCCH_2CH_2$). $^{13}C$ NMR (100 MHz, $CDCl_3$), δ (TMS, ppm): 171.35 (C═O), 149.12, 143.31, 140.98, 140.30, 132.27, 131.32, 127.71, 126.60, 120.79, 83.06 ($CH_2C$≡), 69.39 (HC≡), 32.94 ($OCCH_2$), 23.47 ($OCCH_2CH_2$), 17.79 (≡$CCH_2$). HRMS (MALDI-TOF): 552.2868 [$M^+$, calcd 552.2301].

Example 11

Synthesis of Silica Nanoparticles

Silica nanoparticles (SNPs) were prepared using the Stöber method. Thus, a mixture of 32 mL of ethanol, 0.64 mL of ammonium hydroxide, and 3.9 mL of distilled water was stirred at room temperature for 5 min, after which a solution of TEOS (1 mL) in 4 mL of ethanol was then added drop-wise into the mixture. The solution was stirred at room temperature for 24 h. After incubation, the mixture was centrifuged and the SNPs were redispersed in ethanol under sonication for 5 min. The process was repeated three times and dried in vacuum at room temperature for further experiments.

Example 12

Fabrication of Azide-Functionalized Silica Nanoparticles 200.0 mg of dried SNPs and 30 mL toluene were placed into a 100 mL one-necked round-bottom flask. The nanoparticle solution was redispersed by sonication for min and magnetically stirred at room temperature for 5 min. 45.5 µL (300 µmol) of 3-bromopropyltrichlorosilane was then added. The mixture was stirred for 6 h at room temperature and was subsequently transferred to a centrifuge tube. After centrifuging and removing the supernatant solution, the brominated silica nanoparticles (SNP-Br) were washed three times with toluene and ethanol to remove excess 3-bromopropyltrichlorosilane. The nanoparticles were dried under reduced pressure. Substitution reaction of SNP-Br with sodium azide was carried out by stirring 150.0 mg of the SNP-Br in 5 mL of a saturated solution of sodium azide in DMF for 48 h at room temperature. The suspension was centrifuged and the resultant nanoparticles (SNP-$N_3$) were washed three times with distilled water, acetone, and ethanol and dried under reduced pressure.

Example 13

Surface Functionalization of the SNP-$N_3$ 100 mg of SNP-$N_3$ and 2 mL of ethanol/water mixture (1:1 v/v) were added into a Schlenk tube. 1 mL of THF solution of TPE-containing diyne (38) [82.9 mg (150 µmol)] was then added subsequently. After stirring for 10 min, $CuSO_4$ (1.44 mg, 9 µmol) and sodium ascorbate (2.4 mg, 12 µmol) were added. The reaction was stirred at room temperature for 24 h. The resultant particles were isolated by centrifugation at 3000 rpm for 15 min. The particles were washed with THF, ammonium hydroxide and water one to two times and then dried under vacuum overnight at 45° C. The obtained nanoparticles FSNP-34 were redispersed in ethanol by sonication for the photoluminescence measurement.

The morphology of FSNP-34 was investigated by TEM and SEM analyses and the images are shown in FIG. 39. The particles of FSNP-34 are spherical with uniform sizes. They are well-separated, suggesting that no particle agglomeration occurs after the surface functionalization. Analysis by zeta potential analyzer shows that FSNP-34 exhibits a unimodal size distribution with an average hydrodynamic diameter of 214.1 nm and polydispersity of 0.005 (FIG. 40).

FIG. 41 shows the IR spectrum of FSNP-34; for comparison, the spectra of SNP-Br, SNP-$N_3$, and TPE-containing diynes (38) are also provided in the same FIG. Treatment of SNP-Br with sodium azide leads to the appearance of a sharp peak associated with the stretching vibration of the azide group at 2104 $cm^{-1}$ (FIG. 41B). The peak, however, becomes much weaker in the spectrum of FSNP-34, revealing that most of them have been consumed by the cycloaddition. Moreover, the spectrum of FSNP-34 displays no ≡CH and C≡C stretching vibration of TPE-containing diynes (38) at 3296 and 2118 $cm^{-1}$, respectively but carbonyl stretching at 1758 $cm^{-1}$. These results show that TPE-containing diynes (38) have been successfully grafted on the nanoparticle surface.

The fluorescence spectra of solutions of TPE-containing diynes (38), SNPs and FSNP-34 in ethanol are shown in FIG. 42. There is a fluorescence signal when the solution of SNPs is photoexcited. The fluorescence spectrum of TPE-containing diynes (38) also show negligibly small emission peaks. When the molecules of TPE-containing diynes (38) are covalently grafted on the surface of SNPs, strong fluorescence spectrum peaked at 464 is recorded in FSNP-34. By dissolving TPE-containing diynes (38) and dispersing FSNP-34 with the same molar quantities of luminogens in ethanol, their emission intensities are compared. The emission from FSNP-34 is 18-fold stronger than that from TPE-containing diynes (38). The $\Phi_{F,abs}$ value of FSNP-34 is measured to be 3.6%, which is much lower than those of previously prepared FSNPs with AIE luminogenic cores. The AIE luminogens are present on the surface of FSNP-34 and their phenyl rings can still rotate freely with little constraint. This effectively consumes the energy of the excitons and thus decreases the $\Phi_{F,abs}$ value of the nanoparticles. FIG. 43 shows the zeta potential of FSNP-34 at various pH. Generally, at low pH or in acidic medium, the silanol groups are protonated, thus rendering positive zeta potential to the nanoparticles. On the other hand, at high pH or in alkaline medium, deprotonation of the Si—OH groups occurs, which imparts negative zeta potentials. Although FSNP-34 is close to neutral at pH 3, its zeta potential increases in absolute terms when the pH value becomes higher. The values at pH≥7 are pretty high, suggesting that FSNP-34 possesses a good colloidal stability.

Example 14

Preparation of Azide-Functionalized Fluorescent Silica Nanoparticles

Tetraethoxysilane (TEOS), tetrahydrofuran (THF), trifluoroacetic acid, and other reagents were all purchased from Aldrich and used as received. 3-Azidopropyltriethoxysilane (31) was prepared by substitution reaction of 3-chloropropyltriethoxysilane with sodium azide. Tetraphenylethene-functionalized siloxane (39) and sugar-containing phenylacetylene (40) were synthesized according to previous published procedures (*Chem. Eur. J.* 2010, 16, 4266 and *Macromolecules* 2007, 40, 2633). X-ray photoelectron spectroscopy (XPS) measurements were conducted on a PHI 5600 spectrometer (Physical Electronics) and the core level spectra were measured using a monochromatic Al Kα X-ray source. The analyzer was operated at 23.5 eV pass energy and the analyzed area was 800 mm in diameter. Thermogravimetric analysis (TGA) was performed under nitrogen on a TA instruments 7 TGA analyzer. The heating rate was 10° C./min.

Fluorescent silica nanoparticles carrying a TPE luminogenic core and an azide functional group on the surface were prepared according to the chemical reaction scheme, shown below.

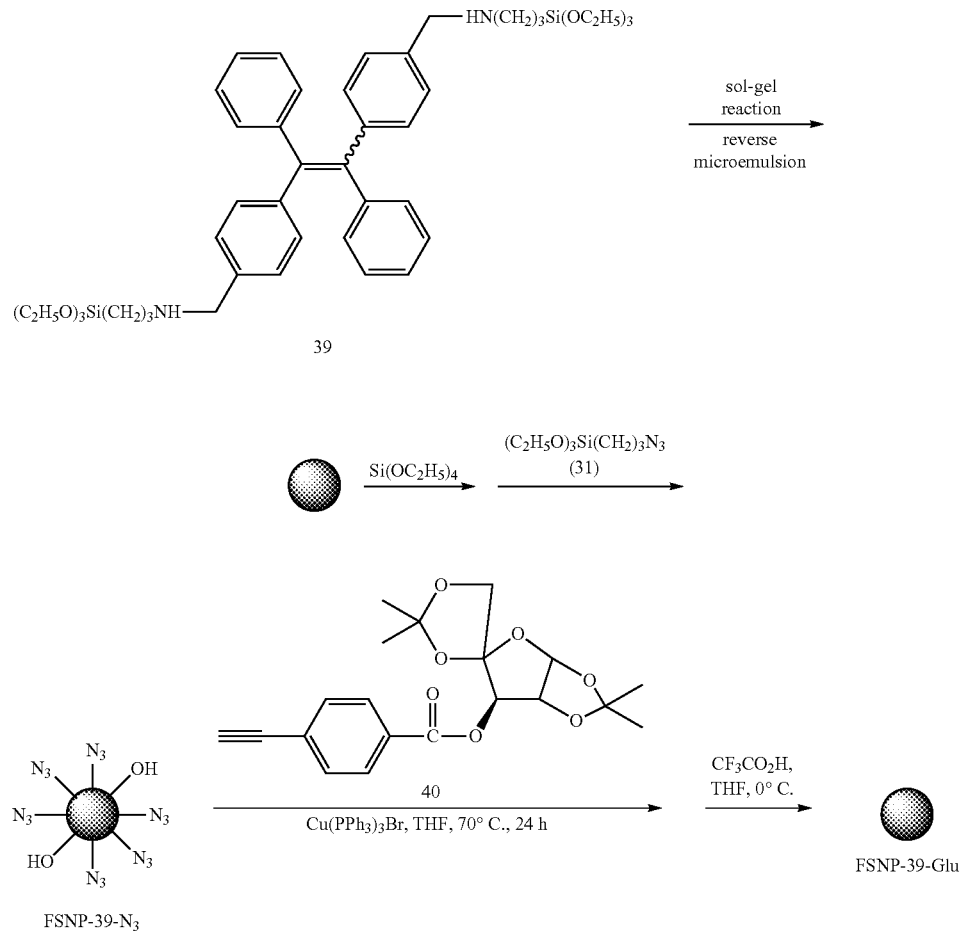

The micelles were prepared at room temperature by sonication of a homogenous solution containing 30 mL of cyclohexane, 7.2 mL of Triton X-100, 5.6 mL of n-heptanol, and 600 µL water for 30 min. 800 µL of 28% ammonia solution was then added. After magnetically stirring for 15 min to obtain a transparent emulsion, 200 µL of adduct Tetraphenylethene-functionalized siloxane (39) was added and the solution was stirred for another 15 min. After dropwise addition of 300 µL TEOS, the mixture was stirred for 30 min. Afterwards, 100 µL of 3-azidopropyltriethoxysilane (31) was slowly added and the solution was stirred for another 24 h at room temperature. Sol-gel reaction of tetraphenylethene-functionalized siloxane (39) with TEOS in the presence of 3-azidopropyltriethoxysilane (31) catalyzed by ammonium hydroxide resulted in the formation of uniform fluorescent silica nanoparticles decorated with azide functional groups on the surface. After completion of the reaction, the microemulsion was terminated by adding ethanol and FSNP-39-$N_3$ was centrifuged and washed with ethanol and water to remove surfactant. The nanoparticles were dried in vacuum at room temperature and then 60° C. for further functionalization.

Example 15

Fabrication of Glucose-Functionalized Fluorescent Silica Nanoparticles

Click reaction of sugar-containing phenylacetylene (40) with FSNP-39-$N_3$ was carried out under nitrogen in a Schlenk tube. 120 mg (0.0202 mmol) of FSNP-39-$N_3$, 73.25 mg (0.0202 mmol) of sugar-containing phenylacetylene (40), and 11.28 mg (6 mol %) of Cu(PPh$_3$)$_3$Br were placed in a 15 mL Schlenk tube. Then, 2 mL of THF was injected into the mixture. After stirring at 60° C. for 24 h, the reaction mixture was diluted with 3 mL of THF and centrifuged at 3000 rpm for 15 min. The nanoparticles were washed with ethanol and water to remove the catalyst. The acetonide protecting groups on the surfaces of the nanoparticles were deprotected under a mild acidic condition. Trifluoroacetic acid/water mixture was an effective agent to cleave the acetal bonds. Briefly, 200 mg of the nanoparticles was first suspended in 2 mL of THF and the mixture was then cooled to ~0° C. using an ice water bath. About 4 mL of a $CF_3CO_2H/H_2O$ (3:1 by volume) mixture was dropped into the nanoparticle suspension under stirring. The ice-water bath was removed and the suspension was allowed to stir at room temperature for 4 h. The reaction was quenched by pouring the suspension into deionized water. The obtained FSNP-39-Glu was repeatedly centrifuged, washed with water, and dried in vacuum at room temperature. Finally, FSNP-39-Glu was dispersed in deionized water or ethanol for further experiments.

The morphologies of FSNP-39-$N_3$ and FSNP-39-Glu were investigated by TEM and SEM analyses. The SEM image of FSNP-39-$N_3$ showed discrete nanoparticles with a smooth surface (FIG. 44). Though well-separated particles were also observed in FSNP-39-Glu, their surfaces were somewhat rough. This suggests the occurrence of a click reaction and demonstrates that the post-functionalization provides little alteration to the morphology of the resultant FSNPs. The TEM images of FSNP-39-Glu shown in FIG. 45 also demonstrate that the particles have a rough surface. The average particle size is measured to be ~50.93±4.41 nm respectively, which is slightly larger than that of FSNP-39-$N_3$ (~42.20±1.55 nm).

The size and distribution of FSNP-39-Glu were measured by a zeta potential analyzer. FSNP-39-Glu exhibits unimodal size distribution and all the particles are uniformly functionalized (FIG. 46). The mean diameter of the nanoparticles is 75.1 nm with a polydispersity of 0.077. The value obtained by a zeta potential analyzer is larger than that determined from the TEM analysis. This is because the zeta potential analyzer gives the mean hydrodynamic diameter of FSNP-39-Glu coated with glucose molecules with numerous hydroxyl groups in aqueous solution, whereas the TEM measurement gives the diameter of FSNP-39-Glu in the dry state coupled with particle shrinkage due to the high power electron beam.

FIG. 47 shows the IR spectra of sugar-containing phenylacetylene (40), FSNP-39-$N_3$, and FSNP-39-Glu. The C≡C and ≡C—H stretching vibrations of sugar-containing phenylacetylene (40) were observed at 2105 and 3247 cm$^{-1}$, respectively, which were not observed in FSNP-39-Glu. The spectrum of FSNP-39-Glu also displayed no azide stretching vibration of FSNP-39-$N_3$ at 2102 cm$^{-1}$, revealing that all the triple bonds of sugar-containing phenylacetylene (40) and azide groups of FSNP-39-$N_3$ have been consumed by the click reaction. No characteristic absorption peaks can be discerned, probably due to their burial by the strong Si—O and Si—OH stretching vibration bands. The XPS spectra of FSNP-39-$N_3$ and FSNP-39-Glu show the expected elements of nitrogen, oxygen, silicon, and carbon (FIG. 48). Though their spectra are almost identical, careful inspection shows that the intensity of C1s peak in FSNP-39-$N_3$ is enhanced after the click reaction due to the fine contribution from sugar-containing phenylacetylene (40). Indeed, the carbon content in FSNP-39-Glu is almost 1.5-fold higher than that in FSNP-39-$N_3$, as shown below in Table 5. Similar results were also obtained from the EDX measurement, further proving that sugar-containing phenylacetylene (40) has been successfully grafted on the surface of FSNP-39-$N_3$.

TABLE 5

Chemical compositions of FSNP-39-$N_3$ and FSNP-39-Glu determined by EDX and XPS analyses

| sample | carbon | nitrogen | oxygen | silicon |
|---|---|---|---|---|
| EDX | | | | |
| FSNP-39-$N_3$ | 7.15 | 0.51 | 35.17 | 57.17 |
| FSNP-39-Glu | 20.08 | 0.41 | 32.66 | 46.85 |
| XPS | | | | |
| FSNP-39-$N_3$ | 23.91 | 5.12 | 46.69 | 24.28 |
| FSNP-39-Glu | 35.06 | 4.67 | 41.51 | 18.75 |

In an embodiment, the thermal stability of the FSNPs is investigated by thermogravimetric analysis (TGA). As shown in FIG. 49, FSNP-39-$N_3$ is thermally quite stable and starts to degrade at ~300° C. Even when heated to 800° C., 85% of its weight is retained. FSNP-39-Glu also enjoys high thermal stability and degrades at a similar high temperature with a high residual yield at 800° C. Since sugar-containing phenylacetylene (40) decomposes completely at 650° C., its amount grafted on the surface of FSNP-39-$N_3$ can be calculated from the thermograms of FSNP-39-$N_3$ and FSNP-39-Glu at this temperature and is equal to 5.55 wt %. FIG. 50 shows the photoluminescence (PL) spectra of suspensions of tetraphenylethene-functionalized siloxane (39), FSNP-39-$N_3$, and FSNP-39-Glu in ethanol solutions. Upon photoexcitation, there is barely a fluorescence signal in tetraphenylethene-functionalized siloxane (39). On the contrary, the PL peaked at 470 nm in FSNP-39-$N_3$ and FSNP-39-Glu under the same measurement conditions. The emission from FSNP-39-Glu is so strong that its intensity is 214-fold higher than that of tetraphenylethene-functionalized siloxane (39). The PL quantum yield of FSNP-39-Glu measured by an integrating sphere is pretty high (37.4%), which can be further enhanced by using higher dye loading and lower TEOS concentration for the sol-gel reaction.

The efficient light emission of FSNP-39-Glu in the solid state enables the same to be utilized as a fluorescent visualizer for specific targeting of cancer cells. HeLa cells and hepatocytes were incubated at different time intervals in serum-free media containing FSNP-39-Glu and their capability to take FSNP-39-Glu was tested under identical conditions. Fluorescence microscopy imaging was used to image the nanoparticles in cell lines treated at different incubation times. Since hepatocytes exhibit a much higher metabolic rate than HeLa cells, they take FSNP-39-Glu more efficiently as they need to utilize glucose as a raw material to produce enough energy for maintaining various cell activities. There may also be specific bioreceptors present on their surface, which can further facilitate the endocytosis. This is demonstrated in the photograph of hepatocytes taken after 3 h of incubation, which shows an obviously stronger fluorescence emission than that of the HeLa cells (FIGS. 51A and D). The photos taken after 5 and 12 hrs also display similar observations. Closer inspection shows that the fluorescence difference between FIG. 51A-C can be clearly discerned, while that between FIG. 51D-F is hard to distinguish, indicating that there is higher uptake efficiency of FSNP-39-Glu by hepatocytes and faster saturation in shorter incubation time.

Example 16

Synthesis of TPE-Containing Siloxane

Tetraethoxysilane (TEOS), dimethylsulfoxide (DMSO), 4-hydroxybenzophenone (6), 1,2-dibromoethane, 3-aminopropyltriethoxysilane (APS), tetrahydrofuran (THF), and other reagents were all purchased from Aldrich and used as received. 3-Azidopropyltriethoxysilane (31) was prepared by nucleophilic substitution of 3-chloropropyltriethoxysilane with sodium azide. Silole-functionalized siloxane (7) and sugar-bearing phenylacetylene (42) were prepared following the literature methods (*Chem. Eur. J.* 2010, 16, 4266 and *Macromolecules* 2007, 40, 2633). $^1$H and $^{13}$C NMR spectra were recorded on a Bruker ARX 400 spectrometer with tetramethylsilane (TMS; δ=0) as an internal standard.

TPE-containing siloxane (41) was synthesized according to the chemical reaction scheme, shown below.

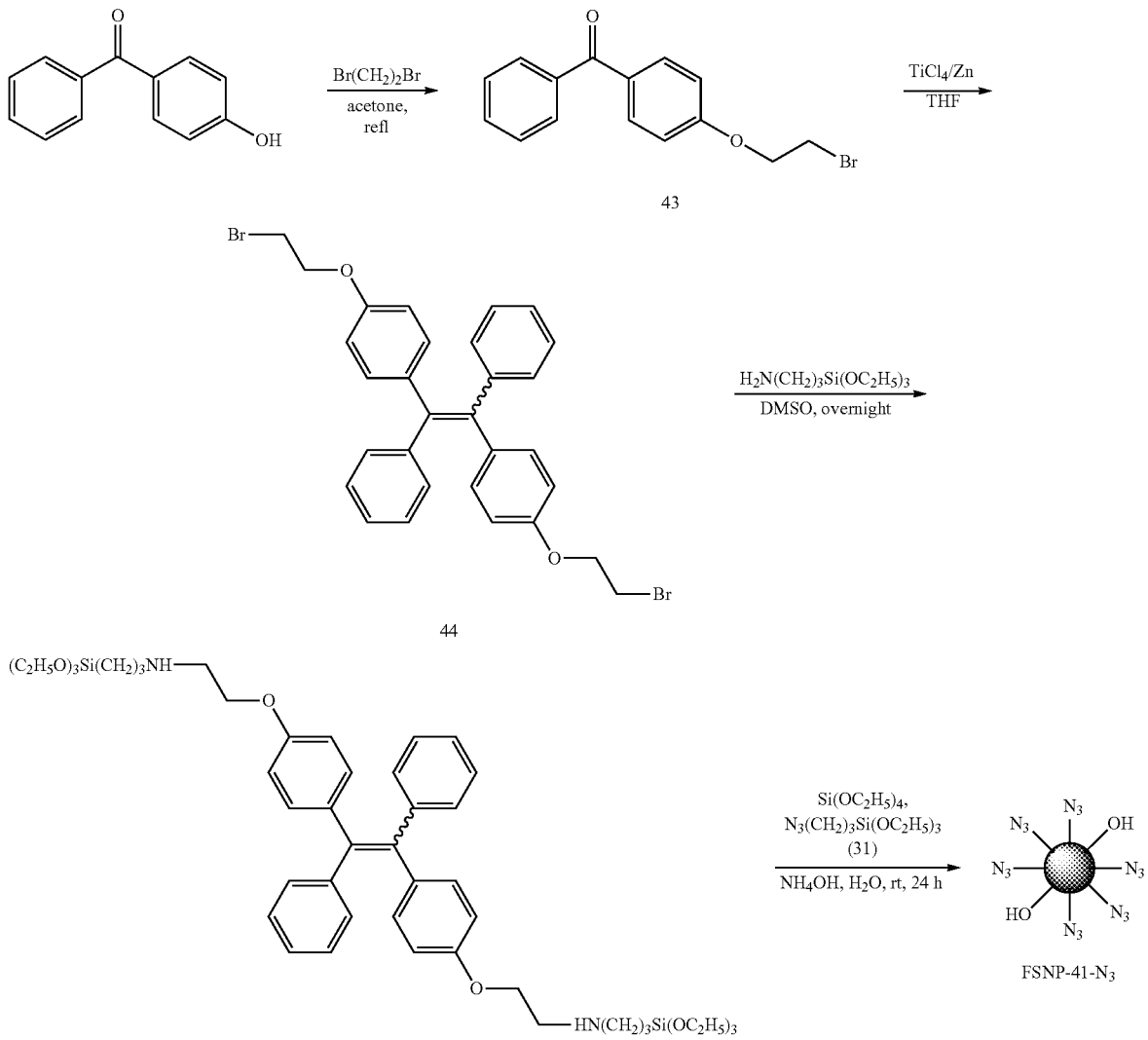

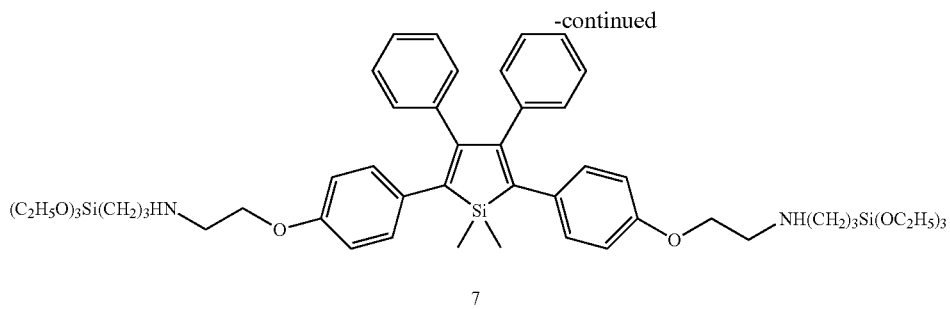
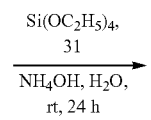
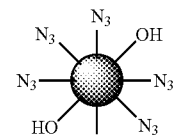
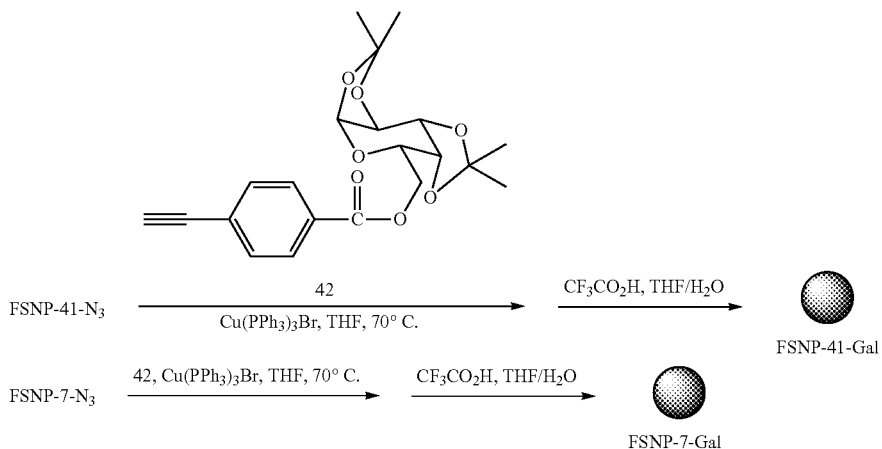

Synthesis of 4-(2-Bromoethoxy)benzophenone (43)

1,2-dibromoethane (9.39 g, 0.05 mol) and potassium carbonate (17.3 g, 0.125 mol) in 100 mL of acetone was added into a 250 mL round-bottom flask. 9.91 g (0.05 mol) of 4-hydroxybenzophenone dissolved in 25 mL of acetone was then added into the flask dropwise within 1 h under reflux. The mixture was heated until the solution color changed from yellow to white. After cooling to room temperature, the inorganic salt was filtered and the solid was washed with acetone several times. The filtrate was concentrated by a rotary evaporator and the residue was extracted with 200 mL of chloroform. The organic phase was washed with 100 mL of water three times, 100 mL of brine once, and then dried over sodium sulfate overnight. After filtration and solvent evaporation, the crude product was purified by a silica gel column using petroleum ether/ethyl acetate mixture (3:1 by volume) as eluent. A white solid of 4-(2-Bromoethoxy)benzophenone (43) was obtained in 60.0% yield (9.15 g). $^1$H NMR (400 MHz, CDCl$_3$), δ (TMS, ppm): 7.84 (d, 2H), 7.76 (d, 2H), 7.59 (t, 1H), 7.49 (t, 2H), 6.98 (d, 2H), 4.37 (t, 2H), 3.67 (t, 2H). $^{13}$C NMR (100 MHz, CDCl$_3$), δ(ppm): 195.5, 161.7, 138.2, 132.7, 132.1, 130.9, 129.8, 128.3, 114.2, 67.9, 28.7.

Synthesis of 1,2-Bis[4-(2-bromoethoxy)phenyl]-1,2-diphenylethene (44)

1.83 g (6 mmol) of 4-(2-Bromoethoxy)benzophenone (43) and 50 mL of THF were added into a vacuum-evacuated, nitrogen-filled 250 mL two-necked, round bottomed flask. The solution was cooled to −78° C., into which TiCl$_4$ (1.14 g, 6 mmol) and Zn dust (0.8 g, 12 mmol) were added. After reflux overnight, the reaction mixture was cooled to room temperature and filtered through a pad of silica gel. The filtrate was concentrated and the crude product was purified by a silica gel column using chloroform/hexane (1:1 by volume) as eluent. A white powder of 1,2-Bis[4-(2-bromoethoxy)phenyl]-1,2-diphenylethene (44) was obtained in 84.82% yield (3.22 g). $^1$H NMR (400 MHz, CDCl$_3$), δ (TMS, ppm): 7.07 (m, 6H), 7.01 (m, 4H), 6.95 (m, 4H), 6.67 (m, 4H), 4.23 (m, 4H), 3.61 (m, 4H). $^{13}$C NMR (100 MHz, CDCl$_3$), δ (ppm): 157.06, 144.6, 140.3, 137.6, 133.2, 131.9, 128.3, 126.9, 114.4, 68.2, 29.7.

TPE-functionalized siloxane (41) was prepared by stirring a mixture of 12 μmol of 1,2-Bis[4-(2-bromoethoxy)phenyl]-1,2-diphenylethene (44) and 28 μmol of APS in 100 μL of DMSO overnight. Water was carefully excluded to avoid possible hydrolysis of APS. The reaction mixture was concentrated under vacuum. The TPE-functionalized siloxane (41) was characterized by mass spectroscopy and used as luminogenic core for the preparation of FSNPs.

The adduct gives an [M$^+$+1] peak at m/z 859.4808 in its high-resolution mass spectrum (FIG. 52), confirming the occurrence of the coupling reaction and the formation of expected product (M$^+$, calcd. 858.4671).

Example 17

Preparation of Azide-Functionalized FSNPs by Reverse Microemulsion Method

The micelles were prepared at room temperature by sonication of a homogenous solution containing 30 mL cyclohexane, 7.2 mL Triton X-100, 5.6 mL n-heptanol, and 600 μL of water for 30 min. 800 μL of ammonia solution (28%) was then added and the solution was magnetically stirred for 15 min to obtain a transparent emulsion. After addition of 200 μL (12 μmol) of TPE-functionalized siloxane (41), the mixture was stirred for 15 min. Afterward, 300 μL of TEOS was injected. The reaction mixture was allowed to stir for 30 min and 100 μL of 3-azidopropyltriethoxysilane (31) was injected. Stirring was continued for 24 h at room temperature and the microemulsion was terminated by adding ethanol. The nanoparticles were centrifuged, washed with ethanol and water, and dried in vacuum at room temperature. Finally, FSNP-41-$N_3$ was dried in a vacuum oven at 60° C. for further surface functionalization. Similarly, FSNP-7-$N_3$ was fabricated by sol-gel reaction of 7 catalyzed by ammonium hydroxide followed by progressive reaction with TEOS and 3-azidopropyltriethoxysilane (31).

Example 18

Fabrication of Galactose-Functionalized FSNPs by Click Reaction

Galactopyranose-containing phenylacetylene (42) was synthesized according to the literature method (*Macromolecules* 2007, 40, 2633). The cycloaddition of 42 with FSNP-41-$N_3$ and FSNP-7-$N_3$ was carried out in THF in the presence of 6 mol % of Cu(PPh$_3$)$_3$Br at 60° C. for 24 h, affording FSNP-41-Gal and FSNP-7-Gal after acetal deprotection in acidic THF/water mixture.

Specifically, a click reaction of Galactopyranose-containing phenylacetylene (42) with FSNP-41-$N_3$ or FSNP-7-$N_3$ was carried out under nitrogen in a Schlenk tube. 120 mg (0.0202 mmol) of FSNP-41-$N_3$, 73.25 mg (0.0202 mmol) of Galactopyranose-containing phenylacetylene (42), and 11.28 mg (6 mol %) of Cu(PPh$_3$)$_3$Br were placed in a 15 mL Schlenk tube. 2 mL of THF was injected into the mixture. After stirring at 60° C. for 24 h, the reaction mixture was diluted with 3 mL of THF and centrifuged at 3000 rpm for 15 min. The obtained nanoparticles were washed with ethanol and water to remove the catalyst. The acetonide protecting groups on the surfaces of the nanoparticles were deprotected under a mild acidic condition. Trifluoroacetic acid/water mixture was an effective agent to cleave the acetal bonds. Briefly, 200 mg of nanoparticles were first suspended in 2 mL of THF and the mixture was then cooled to ~0° C. using an ice water bath. About 4 mL of a CF$_3$CO$_2$H/H$_2$O (3:1 by volume) mixture was dropped into the nanoparticle suspension under stirring. The ice-water bath was removed and the resultant nanoparticle suspension was allowed to stir at room temperature for 4 h. The reaction was terminated by pouring the nanoparticle suspension into deionized water. The obtained FSNP-41-Gal was repeatedly centrifuged, washed with water, and dried in vacuum at room temperature. Finally, FSNP-41-Gal was dispersed in deionized water or ethanol for further experiments. Similarly, FSNP-7-Gal was obtained by the above-mentioned procedures.

The galactose-functionalized FSNPs show high uniformity in shape and size, as revealed by the TEM and SEM analyses (FIGS. 53 and 54). The surfaces of FSNP-41-Gal and FSNP-7-Gal are somewhat rough, revealing the success of surface functionalization. The average sizes of FSNP-41-Gal and FSNP-7-Gal determined from the TEM micrographs were 46.27±3.73 nm and 46.66±4.04 nm, respectively. The images at high magnification show that the particles were indeed covered by a layer of biomolecules. The SEM and TEM images of both samples reveal well-separated and homogenous particles, suggesting that the surface functionalization process provided little alteration to their morphology and size. The mean diameter and size distribution of the FSNP-1-Gal and FSNP-2-Gal are determined by a zeta potential analyzer and the results are shown in FIG. 55. Both samples exhibit unimodal size distributions, meaning that the biomolecules were uniformly decorated on their surfaces. The mean diameters of FSNP-41-Gal and FSNP-7-Gal were measured to be 66.4 and 67.3 nm, respectively, with polydispersity of 0.005. The average sizes of the FSNPs obtained by zeta potential analyzer were somewhat larger than those determined from TEM. It is because the zeta potential analyzer gives the mean hydrodynamic diameters of FSNP-41-Gal and FSNP-7-Gal surrounded by galactose molecules with numerous hydroxyl groups in aqueous solution, whereas the TEM measurements demonstrate the sizes of FSNP-41-Gal and FSNP-7-Gal in the dry state and often show underestimated values due to particle shrinkage by the high power electron beam.

FIG. 56 shows the IR spectrum of FSNP-41-Gal; for comparison, the spectra of Galactopyranose-containing phenylacetylene (42) and FSNP-41-$N_3$ are also given in the same FIG. The spectrum of Galactopyranose-containing phenylacetylene (42) show characteristic absorption peaks at 2105 and 3247 cm$^{-1}$ associated with its C≡C and ≡CH stretching vibrations, respectively. These peaks are however, not observed in FSNP-41-Gal. The spectrum of FSNP-41-Gal also displays no azide stretching vibration of FSNP-41-$N_3$ at 2113 cm$^{-1}$. New peaks attributed to C=C and C=N stretching vibrations emerged albeit with weak intensities, revealing that the triple bonds of Galactopyranose-containing phenylacetylene (42) and the azide groups of FSNP-41-$N_3$ have been converted to triazole rings in FSNP-41-Gal. Similar results are shown for FSNP-7-Gal. Its spectrum shows absorptions peaks of Galactopyranose-containing phenylacetylene (42) and FSNP-7-$N_3$ but exhibit no C≡C, ≡C—H, and $N_3$ stretching vibrations at 2105, 3247 and 2113 cm$^{-1}$ (FIG. 57).

In a further embodiment, the chemical compositions of the FSNPs before and after the click reaction were investigated by X-ray photoelectron spectroscopy and the results are summarized in Table 6, below. Both FSNP-41-$N_3$ and FSNP-7-$N_3$ contain expected elements of nitrogen, oxygen, and silicon. After surface functionalization, the carbon content increases, whereas relatively lower intensities are observed for the nitrogen, oxygen, and silicon elements. Such comparison supports the success of grafting of Galactopyranose-containing phenylacetylene (42) on FSNPs.

TABLE 6

Chemical compositions of FSNP-41-$N_3$, FSNP-41-Gal, FSNP-7-$N_3$, and FSNP-7-Gal determined by XPS analyses

| FSNPs | carbon | nitrogen | oxygen | silicon |
|---|---|---|---|---|
| FSNP-41-$N_3$ | 21.62 | 5.21 | 49.27 | 23.90 |
| FSNP-41-Gal | 35.71 | 4.41 | 41.82 | 18.05 |
| FSNP-7-$N_3$ | 19.73 | 5.54 | 50.54 | 24.20 |
| FSNP-7-Gal | 35.86 | 4.92 | 41.58 | 17.64 |

FIG. 58 shows the TGA thermograms of the azide and galactose-functionalized fluorescent silica nanoparticles recorded under nitrogen at a heating rate of 10° C./min. FSNP-41-N₃ and FSNP-7-N₃ enjoy high thermal stability and degrade at temperatures at ~350° C. Even when heated to 600° C., more than 80% of their weight is retained, indicating that they are promising ceramic materials. FSNP-41-Gal and FSNP-7-Gal begin to lose their weights at similar temperatures. Their residual yields at 600° C., however, are lower. Since Galactopyranose-containing phenylacetylene (42) degrades completely at 800° C., the amount of Galactopyranose-containing phenylacetylene (42) grafted on the surfaces of FSNPs can be calculated by subtracting the weights of FSNP-41-N₃ and FSNP-7-N₃ from those of FSNP-41-Gal and FSNP-7-Gal at the same temperature, and are equal to 9.3 and 6.88%, respectively. The grafting efficiency is not high because the galactose moiety is sterically bulky. When certain amounts of such molecule are occupied on the nanoparticle surface, the remaining molecules of Galactopyranose-containing phenylacetylene (42) can hardly undergo a click reaction with the azide functionalities due to the severe steric hindrance.

The PL spectra of suspensions of TPE-functionalized siloxane (41), FSNP-41-N₃, and FSNP-41-Gal in ethanol solutions are shown in FIG. 59A. Upon photoexcitation, there was almost no fluorescence emission detected in TPE-functionalized siloxane (41). On the contrary, strong blue light emitted at 466 nm in FSNP-41-N₃ and FSNP-41-Gal, whose intensities are 253 and 218-folds higher than that of TPE-functionalized siloxane (41). In a similar fashion, adduct silole-APS conjugate (7) is nonemissive but FSNP-7-N₃ and FSNP-7-Gal emit intensely upon photoexcitation, thanks to the restriction of the intramolecular motions of the silole aggregates by the rigid silica network (FIG. 59B).

To test whether FSNP-41-Gal and FSNP-7-Gal can target specific cancer cells, HeLa and HepG2 cell lines were employed. FIG. 60 shows the fluorescent images of HeLa cells and HepG2 cultured in media containing FSNP-41-Gal and FSNP-7-Gal at different time intervals. The uptake efficiency in terms of fluorescence by HeLa and HepG2 cells is compared under identical conditions by employing the fluorescence microscopy imaging technique. The HepG2 cells express a high metabolic rate in order to produce enough energy for various activities to maintain cell life. The HeLa cells do have metabolism but the rate is much lower. Accordingly, it is likely that HepG2 shows a higher affinity to FSNP-41-Gal and FSNP-7-Gal and hence exhibits brighter fluorescence images. Moreover, there is a high density of asialoglycoprotein (ASGP-R) receptors present in hepatocytes (500,000 receptors per cell), which assist the endocytosis of FSNP-41-Gal and FSNP-7-Gal within membrane-bond vesicles or endosomes. This is so called receptor-mediated endocytosis. When FSNP-41-Gal and FSNP-7-Gal bind to the ASGP-R receptor, the nanoparticle-receptor complex is rapidly internalized and the receptor recycles back to the surface, resulting in high binding capacity and efficient particle uptake. Indeed, the images of HepG2 are much brighter than those of HeLa cells stained by FSNP-41-Gal under the same experimental conditions (FIG. 60). Careful inspection of the photos taken at different incubation times reveals the emission difference between the images in FIG. 60D-F is smaller than those in FIG. 60A-C, revealing a higher rate of nanoparticle uptake in HepG2 and thus resulting in faster emission saturation at earlier incubation time. Similar phenomenon is also found in HepG2 images stained by FSNP-7-Gal.

Example 19

Synthesis of 5-oxo-5-[3-(triethoxysilyl)propylamino]pentanoic acid

Tetraethoxysilane (TEOS), 3-aminopropyltriethoxysilane (43), dimethylsulfoxide (DMSO), succinic anhydride (44), 1,3-dicyclohexylcarbodiimide (DCC), 4-dimethylaminopyridine (DMAP), N-hydroxysuccinamide (NHS), and other reagents were purchased from Aldrich and used as received. TPE and silole-functionalized siloxanes (39 and 7) were synthesized according to the previous published method (*Chem. Eur. J.* 2010, 16, 4266). IR spectra were obtained on a Perkin-Elmer 16 PC FTIR spectrophotometer. 1H and ¹³C NMR spectra were recorded on a Bruker ARX 400 spectrometer with tetramethylsilane (TMS; δ=0) as an internal standard.

Compound 45, named 5-oxo-5-[3-(triethoxysilyl)propylamino]pentanoic acid, was prepared by reaction of 3-aminopropyltriethoxysilane with succinic anhydride, as shown in the chemical reaction scheme below.

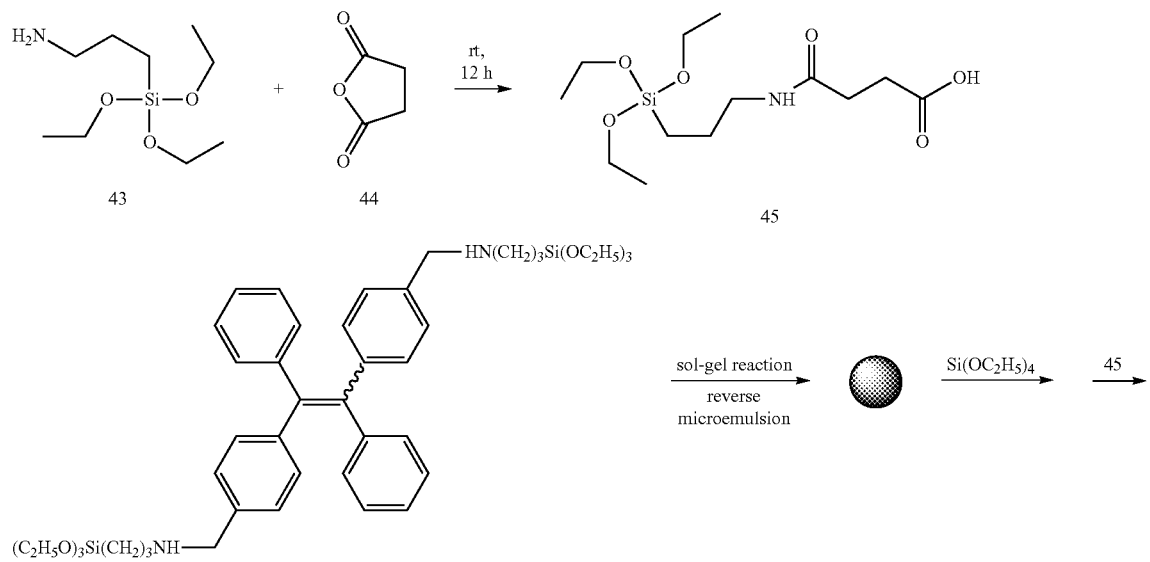

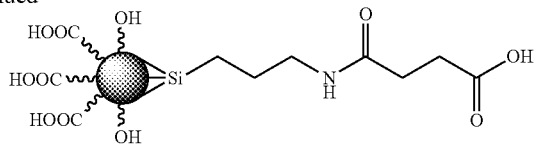

FSNP-39-COOH

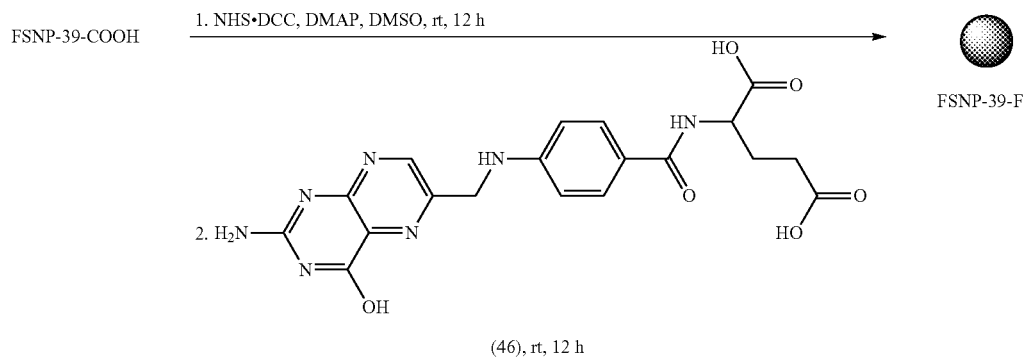

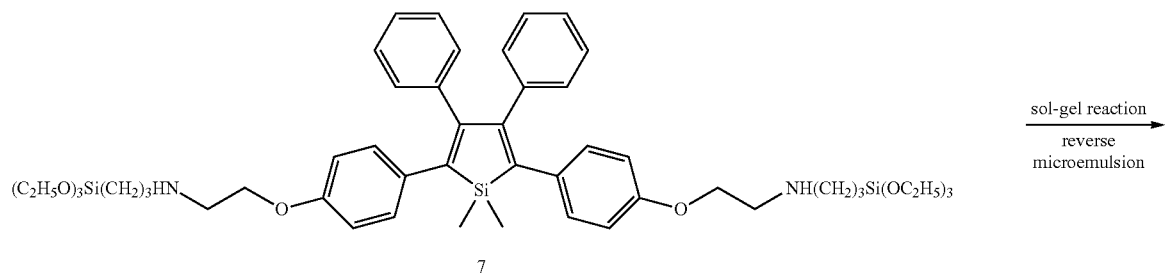

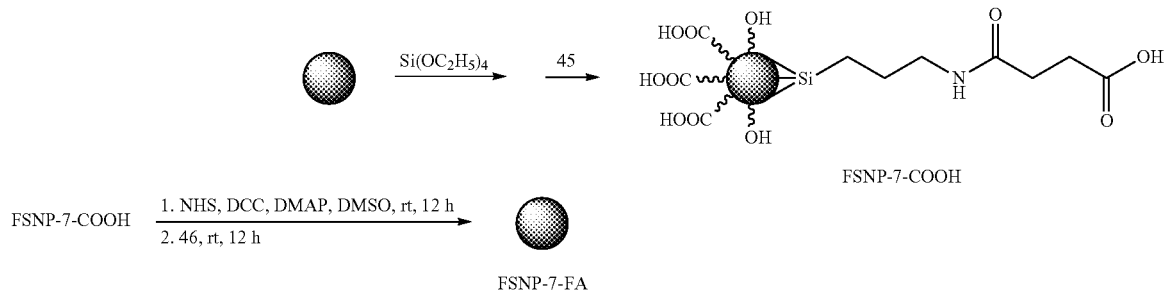

An equimolar mixture of 4.79 mL (20 mmol) of 3-aminopropyltriethoxysilane (43) and 2.0 g (20 mmol) of succinic anhydride (44) was reacted overnight at room temperature under nitrogen atmosphere. The product was extensively washed with methanol and used without further purification. Yellow oil. IR, ν (cm$^{-1}$): 3418 (NH), 3278 (OH), 2977 (CH$_2$), 1723 (CO), 1652 (CONH), 1563 (NH), 1026 (SiO). $^1$H NMR (400 MHz, DMSO-d$_6$), δ(TMS, ppm): 0.62 (t, 2H, S$_1$—CH$_2$), 1.14-1.25 (m, 9H, CH$_3$), 1.52 (t, 2H, CH$_2$), 2.38-2.49 [m, 4H, CO(CH$_2$)$_2$], 3.09 (m, 2H, NHCH$_2$), 3.83 (m, 6H, OCH$_2$), 7.91 (s, 1H, NH). $^{13}$C NMR (100 MHz, DMSO-d$_6$), δ (ppm): 7.38, 18.23, 22.79, 29.41, 30.17, 41.37, 56.09, 57.73, 170.86, 174.01.

Example 20

Preparation of Carboxylic Acid-Functionalized FSNPs

FSNP-39-COOH and FSNP-7-COOH were prepared by the reverse microemulsion method, as shown in the chemical reaction scheme, below.

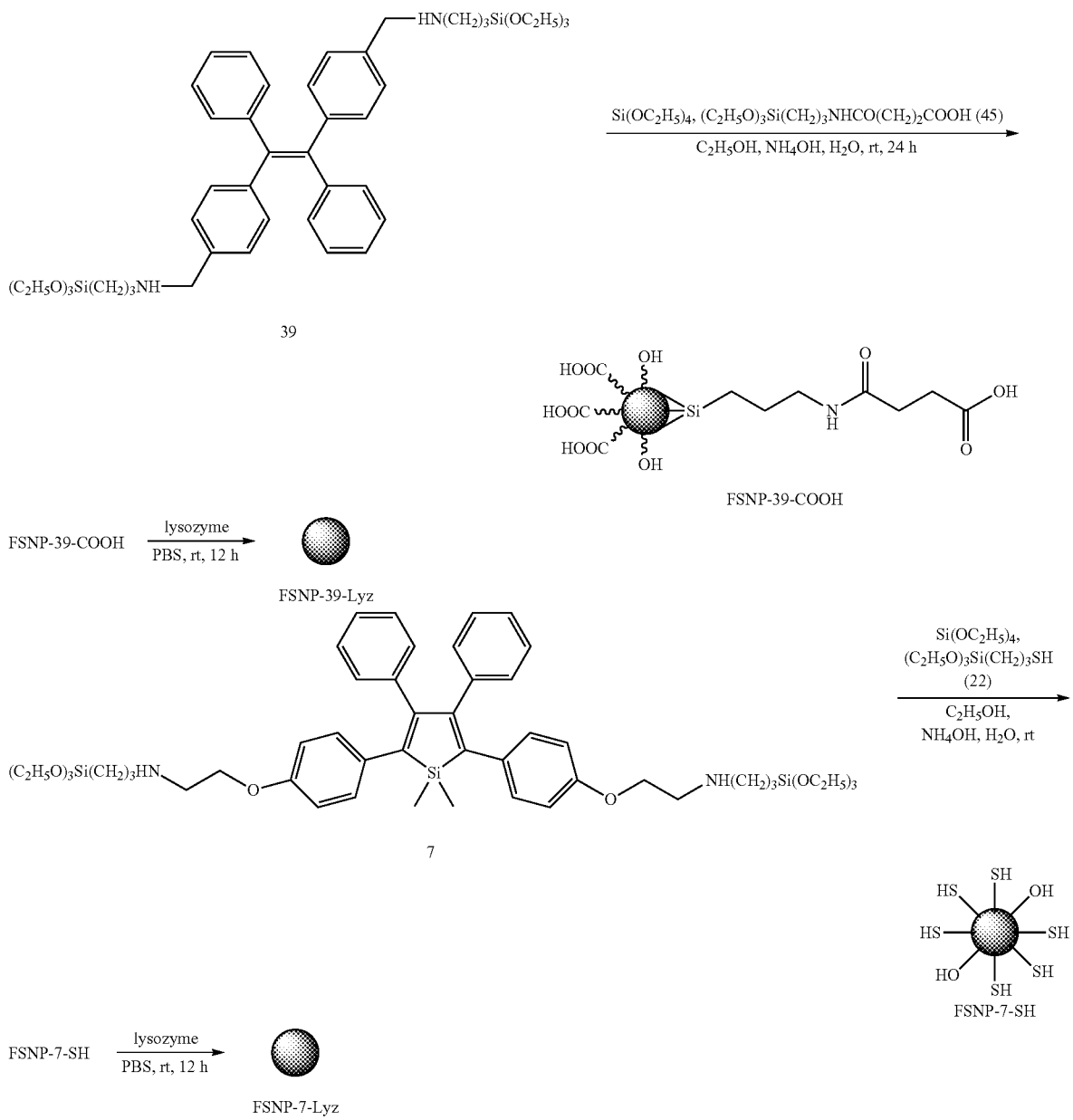

Micelles were prepared at room temperature by sonication of a homogenous solution containing 30 mL of cyclohexane, 7.2 mL of Triton X-100, 5.6 mL of n-heptanol, and 600 μL water for 30 min. 800 μL of 28% ammonia solution was then added. After magnetically stirring for 15 min to obtain a transparent emulsion, 200 μL (12 μmol) of TPE and silole-functionalized siloxanes (39 and 7) were added and the solution was stirred for another 15 min. After dropwise addition of 300 μL TEOS and stirring for 30 min, 100 μL (93.33 μmol) of 5-oxo-5-[3-(triethoxysilyl)propylamino] pentanoic acid (45) in DMSO was slowly added and the reaction was stirred for another 24 h at room temperature. Sol-gel reaction of TPE and silole-functionalized siloxanes (39 and 7) with TEOS in the presence of 5-oxo-5-[3-(triethoxysilyl)propylamino]pentanoic acid (45) catalyzed by ammonium hydroxide resulted in the formation of FSNP-39-COOH and FSNP-7-COOH with surfaces decorated with carboxyl acid groups. After the reaction was completed, the microemulsion was terminated by adding ethanol and FSNP-39-COOH and FSNP-7-COOH were centrifuged and washed with ethanol and water to remove the surfactant. The nanoparticles were dried in vacuum at room temperature and then 45° C. for further functionalization.

Example 21

Fabrication of Folic Acid-Functionalized FSNPs

FSNP-39-FA was prepared by amidation of FSNP-39-COOH with folic acid in the presence of NHS, DCC, and DMAP in DMSO.

Specifically, 100 mg (93 μmol) of FSNP-39-COOH, 80 mg of DCC, 3.0 mg of DMAP, and 11.5 mg (100 μmol) of NHS in 1.5 mL of DMSO were placed into a 15 mL Schlenk tube. After stirring at room temperature for 12 h, 41.20 mg (93 μmol) of folic acid pre-dissolved in 0.5 mL DMSO was added to the reaction mixture. After stirring at room temperature for 12 h, the mixture was diluted with 3 mL of DMSO and centrifuged at 3000 rpm for 15 min. The isolated FSNP-39-FA was washed with DMF and water to remove the catalytic by-product. The nanoparticles were washed with deionized water and ethanol several times to completely remove all the impurities. Finally, FSNP-39-FA was dispersed in deionized water or ethanol for further experiments. A similar procedure was used to prepare FSNP-7-FA.

The morphologies of FSNP-39-COOH, FSNP-7-COOH, FSNP-39-FA, and FSNP-7-FA were investigated by TEM and SEM analyses. The SEM image of FSNP-39-COOH shows discrete nanoparticles with relatively smooth surfaces (FIG. 61A). Although well-separated particles are also observed in FSNP-39-FA, their surfaces are somewhat rough. This suggests the success of the occurrence of amidation on the surface of FSNP-39-COOH and demonstrates that the post-functionalization provides litter alteration to the morphology of the resultant FSNPs. The TEM images of FSNP-39-FA shown in FIG. 62 also show that the particles have a rough surface when compared to FSNP-39-COOH. The average particle size is measured to be ~42.06±3.49 nm, which is slightly larger than that of FSNP-41-COOH (~43.33±2.45 nm).

FIG. 63 shows the SEM images of FSNP-7-COOH and FSNP-7-FA. The surface morphology of FSNP-7-COOH changes but only in a small extent after the post-functionalization. The TEM images taken before and after modification reveal that the particle size of FSNP-7-COOH (~50.02±3.62 nm) is slightly larger than that of FSNP-7-COOH (~51.79±2.37 nm) (FIG. 64). All the folic acid-functionalized FSNPs exhibit unimodal size distributions, suggesting that all the particles are uniformly functionalized.

The size and morphology of FSNP-39-COOH and FSNP-7-COOH are affected by many reaction parameters. The addition mode of TPE and silole-functionalized siloxanes (39 and 7) and the nature of solvent used for the dissolution of 5-oxo-5-[3-(triethoxysilyl)propylamino]pentanoic acid (45) have a strong influence on the shape and size of the resultant nanoparticles. For example, when TPE-functionalized siloxane (39), a viscous oil, was directly added to the reaction mixture, agglomeration of the particles occurred (FIG. 65A). In another case, if TPE-functionalized siloxanes (39) was premixed with a small amount of ethanol prior to the addition, monodispersed nanoparticles are generated (FIG. 65B). Nanoparticles with even better quality were obtained when a DMSO solution of 5-oxo-5-[3-(triethoxysilyl)propylamino]pentanoic acid (45) was used for the surface modification (FIG. 65C). The molecules of 5-oxo-5-[3-(triethoxysilyl)propylamino]pentanoic acid (45) may be better solvated in DMSO, thus allowing them to undergo sol-gel reaction with every single fluorescent silica nanoparticle in the suspension mixture. FIG. 65D-F show the TEM images of FSNP-7-COOH prepared using the same conditions as those in FIG. 65A-C. Discrete, uniform nanoparticles were observed as the surface functionalization was carried out using a solution of silole-functionalized siloxane (7) in DMSO.

XPS and EDX analyses were carried out to realize the composition of the FSNPs, and their chemical compositions are summarized in Table 7, below. All the FSNPs show the expected elements of nitrogen, oxygen, silicon, and carbon. The carbon and nitrogen contents of FSNP-39-FA and FSNP-7-FA are higher than their precursors FSNP-39-COOH and FSNP-7-CONHS. Similar results are also obtained from the EDX measurements, proving that folic acid has been successfully grafted on the surfaces of FSNP-39-COOH and FSNP-7-COOH. The success in bioconjugation of FA on FSNP-39-COOH and FSNP-7-COOH is also evidenced by the TGA analysis. As shown in FIG. 66, FSNP-39-COOH and FSNP-7-COOH are thermally quite stable and start to degrade at a temperature of ~300° C. Even when heated to 800° C., ~79% of their weight is retained. FSNP-39-FA and FSNP-7-FA also enjoy high thermal stability and degrade at similar temperatures with high residual yields at 800° C. Since folic acid decomposes completely at 750° C., the weight loss from 300 to 750° C. in FSNP-39-FA and FSNP-7-FA should be due to the degradation of FA and is equal to 5.10 and 6.65 wt %, respectively.

TABLE 7

Chemical compositions of the nanoparticles determined by EDX and XPS analyses

| FSNPs | carbon | nitrogen | oxygen | silicon |
|---|---|---|---|---|
| EDX | | | | |
| FSNP-39-COOH | 21.13 | 0.78 | 33.40 | 29.96 |
| FSNP-39-FA | 56.93 | 1.48 | 24.55 | 17.04 |
| FSNP-7-COOH | 21.48 | 0.20 | 39.98 | 38.35 |
| FSNP-7-FA | 58.13 | 2.25 | 20.71 | 18.92 |
| XPS | | | | |
| FSNP-39-COOH | 21.34 | 3.22 | 52.32 | 23.12 |
| FSNP-39-FA | 31.35 | 8.44 | 41.48 | 18.73 |
| FSNP-7-CONHS | 29.85 | 4.62 | 44.18 | 21.35 |
| FSNP-7-FA | 31.77 | 5.53 | 43.92 | 18.78 |

The PL spectra of suspensions of TPE-functionalized siloxanes (39), silole-functionalized siloxanes (7), FSNP-39-COOH, FSNP-7-COOH, FSNP-39-FA, and FSNP-7-FA in ethanol solutions are given in FIG. 67. Upon photoexcitation, there are almost no fluorescence signals in TPE-functionalized siloxanes (39). On the contrary, the PL peaked at 465 nm in FSNP-39-COOH and FSNP-39-FA under the same measurement conditions due to the restriction of intramolecular rotations of the TPE aggregates by the rigid silica network. FSNP-39-COOH and FSNP-39-FA are highly emissive (FIG. 67A), with an intensity 380-fold higher than that of TPE-functionalized siloxanes (39). Similar to TPE-functionalized siloxanes (39), silole-functionalized siloxanes (7) are nonemissive in the solution state, whereas the ethanol solutions of FSNP-7-COOH and FSNP-7-FA emit intensely upon UV irradiation (FIG. 67B). Under the same measurement conditions, the PL intensity of FSNP-7-FA is 94-fold higher than silole-functionalized siloxanes (7). The absolute PL quantum yields of FSNP-39-FA and FSNP-7-FA, measured by integrating sphere, are 38.0 and 47.0%, respectively, whose values can be further enhanced by increasing the luminogen loading and decreasing the TEOS concentration used for the nanoparticle fabrication.

The strong PL from FSNP-39-FA and FSNP-7-FA enable them to function as fluorescent visualizers for intracellular imaging. HeLa cells were chosen for the experiment since they are known to express high level of folate receptor (FR). The HeLa cells were incubated with FSNP-41-FA and FSNP-7-FA and the uptake efficiency at different time intervals was compared by means of the brightness of the fluorescent images shown in FIGS. 68 and 69. The cellular uptake of folate polymer micelles was reported to decline gradually after the first hour of incubation. If the incubation time is too short, the effect of FR-mediated endocytosis is not obvious. A long incubation time, however, may lead to fluorescence saturation and make the comparison among different formulations difficult. Here, the incubation time was chosen to be 1, 2, 3, and 8 h. As shown in FIG. 68A, after 1 h of incubation, strong fluorescence is observed in the cytoplasm of the cells as a result of the active folate receptor-mediated endocytosis. The PL from the HeLa cells incubated for 2, 3, and 8 h is similar to or weaker than that at 1 h, probably due to the fluorescence saturation by the maximum amount of FSNPs taken by the cells. The brightness of the images of HeLa cells stained by FSNP-7-FA increases progressively when the incubation time is prolonged from 1 to 2, and then 3 h. Further increment of the time to 8 h leads to no enhancement in the light emission.

Example 22

Preparation of Thiol-Functionalized FSNPs

Tetraethoxysilane (TEOS), 3-mercaptopropyltriethoxysilane (22), and other reagents were all purchased from Aldrich and used without further purification. Adduct TPE and silole-functionalized siloxanes (39 and 7) were prepared according to the previous published procedure (*Chem. Eur. J.* 2010, 16, 4266). 5-Oxo-5-[3-(triethoxysilyl)propylamino] pentanoic acid (45) was prepared by reaction of 3-aminopropyltriethoxysilane with succinic anhydride.

FSNP-39-COOH was prepared from TPE-functionalized siloxanes (39), TEOS, and 5-Oxo-5-[3-(triethoxysilyl)propylamino]pentanoic acid (45) by a one-pot, two-step sol-gel reaction. FSNP-SH, on the other hand, was prepared from silole-functionalized siloxanes (7), TEOS, and 3-mercaptopropyltriethoxysilane (22). About 12 µmol of silole-functionalized siloxanes (7) were added into a mixture of ethanol (32 mL), ammonium hydroxide (0.64 mL), and distilled water (3.9 mL). The solution was stirred at room temperature for 30 min after which an ethanol solution (5 mL) of TEOS (1 mL) was added dropwise. The solution was stirred at room temperature for 3 h to coat the luminogenic nanocores with silica shells followed by the drop-wise addition of 100 µL of 3-mercaptopropyltriethoxysilane (22) in DMSO. After stirring for 24 h at room temperature, the mixture was centrifuged and the nanoparticles were redispersed in ethanol under sonication for 5 min. Such process was repeated three times and FSNP-7-SH was finally dispersed in water or ethanol for further experiments.

The morphologies of FSNP-39-COOH and the FSNP-7-SH were investigated by TEM analysis. The TEM images of FSNP-39-COOH and FSNP-7-SH show discrete nanoparticles with smooth surfaces (FIG. 70). Both nanoparticles are monodispersed with spherical shapes and show no apparent agglomeration. When 5-Oxo-5-[3-(triethoxysilyl)propylamino]pentanoic acid (45) was added directly to the mixture without prior dissolution in DMSO, big lumps of particles were generated. Similar results were also observed when TPE-functionalized siloxanes (39) and TEOS were added simultaneously. The average particle sizes of FSNP-39-COOH and FSNP-7-SH were measured to be 163.43±10.29 and 188.02±8.67 nm, respectively. The size and distribution of FSNP-39-COOH and FSNP-7-SH were measured by a zeta potential analyzer. FSNP-39-COOH and FSNP-7-SH exhibit unimodal size distributions, suggesting that all the particles are uniformly functionalized (FIG. 71). The mean diameters of FSNP-39-COOH and FSNP-7-SH are 179.0 and 196.9 nm, respectively, with a polydispersity of 0.005. The values obtained by the zeta potential analyzer are larger than those determined from the TEM analysis because the zeta potential analyzer gives the mean hydrodynamic diameters of FSNP-39-COOH and FSNP-2-SH coated with carboxylic acid and thiol groups in the aqueous media, whereas the TEM measurements give the diameters of the FSNPs in the dry state coupled with particle shrinkage due to the high power electron beam.

FIG. 72 shows the PL spectra of suspensions of TPE-functionalized siloxanes (39), FSNP-39-COOH, silole-functionalized siloxanes (7), and FSNP-7-SH in ethanol solutions. Upon photoexcitation, there are almost no fluorescence signals in TPE-functionalized siloxanes (39) (FIG. 72A). On the contrary, a strong PL peak at 462 nm is observed in FSNP-39-COOH under the same measurement conditions. The emission from FSNP-39-COOH is so strong that its intensity is 243-fold higher than that of TPE-functionalized siloxanes (39). The same phenomena were also observed in silole-functionalized siloxanes (7) and FSNP-7-SH. Whereas silole-functionalized siloxanes (7) are practically nonemissive in the solution state, there is a PL peak at 485 nm in FSNP-7-SH, which is 36-fold stronger than that of silole-functionalized siloxanes (7). The PL quantum yield of FSNP-39-COOH and FSNP-7-SH, measured by an integrating sphere, is pretty high and is equal to 29.3 and 33.2%, respectively, which can be further enhanced by using higher dye loading and lower TEOS concentration for the sol-gel reaction.

Example 23

Lysozyme Adsorption at Different pH

The adsorption of lysozyme on FSNP-39-COOH and FSNP-7-SH was studied in buffer solutions with different pH at 25° C. 2000 µg of lysozyme were first dissolved in 2 mL of water and then mixed with 3 mL of buffer solution (pH=2). About mg of FSNP-39-COOH was suspended in the lysozyme buffer solution and the mixture was incubated at room temperature for 12 h. The same process was done for buffer solutions with pH=3-10. Similarly, in another set of experiments, 2000 µg of lysozyme were first dissolved in 2 mL of water and then mixed with 3 mL of buffer solution (pH=2). About 5 mg of FSNP-7-SH were suspended in the lysozyme buffer solution and the mixture was incubated at room temperature for 12 h. The same process was done for buffer solutions with pH=3-10. The mixtures were centrifuged and the UV absorptions of the supernatants were measured.

The absorption change in the buffer solutions of lysozyme before and after adsorption by FSNP-39-COOH and FSNP-7-SH at different pH at 25° C. is given in FIG. 73. For both FSNPs, the adsorption increases or the absorbance decreases with an increase in the pH value. Such observation agrees well with the previous observations that electrostatic attractions between the positively charged lysozyme and negatively charged silica are responsible for the adsorption. It is proposed that the lysozyme adsorption is less favorable in media with low pH values because in acidic conditions, the lysozyme molecules bear a higher positive charge (+8 at pH 8.0 and +10 at pH 4.0), which promotes protein-protein electrostatic repulsion. Although such interaction will be minimized at low lysozyme loading, it will reduce the chance for the protein molecules to encounter the nanoparticles. An alternative explanation for the lower adsorption efficiency at lower pH is the pH-induced change in the zeta potential of the silica, which results in decreased electrostatic attraction between the two components. At higher pH, the lysozyme molecules exhibit lower positive surface charge because of their high isoelectric point at pH 11. On the other hand, the silica shows a higher negative surface charge in basic media. Thus, solutions of high pH values should be more suitable for the lysozyme adsorption. It is noteworthy that the absorbance of the protein solutions drops to a larger extent after incubation with FSNP-39-COOH rather than FSNp-7-SH, revealing the former nanoparticles possess a higher adsorption capacity.

Colloidal stability is a key parameter for nanoparticles or colloidal systems and can be realized from their surface charges or zeta potentials. The nanoparticles are said to be colloidally stable if their surface charges are high at the workable pH, irrespective of the sign. The functional groups on the surfaces of FSNPs determine their charges and hence the zeta potentials at different pH. FSNP-39-COOH carries a high negative charge at high pH due to deprotonation of the carboxylic groups by acid-base reaction. At low pH, protonation of the silanol groups occurs, which endows the nanoparticles with a positive surface charge. The zeta potential of FSNP-7-SH is similar to that of FSNP-7-COOH in acidic media but is less negative at pH 5-10. At pH 12, both nanoparticles exhibit high negative surface charges and hence enjoy good colloidal stability (FIG. 77). Compared with carboxylic acid, the thiol group is less acidic and is less likely to undergo deprotonation in less basic solutions. This explains why at pH 10, its adsorption performance is poorer than FSNP-39-COOH.

Example 24

Lysozyme Adsorption at Different Protein Concentrations

The amounts of lysozyme adsorbed respectively by fixed concentrations of FSNP-39-COOH and FSNP-7-SH were determined by the following procedures. Briefly, mg of FSNP-COOH or FSNP-7-SH were added into 2 mL of aqueous lysozyme solutions with concentrations of 50, 100, 200, 500, 600, and 800 μg/mL. 3 mL of buffer solution were added to each suspension to obtain mixtures with pH=10. The mixtures were incubated for 12 h at room temperature under vigorous shaking. To determine the amount of lysozyme adsorbed on the particle surface, samples were withdrawn from each suspension and added into plastic centrifuge cuvettes. Subsequently, the cuvettes were centrifuged for 15 min at 3000 rpm at 25° C. The supernatants were transferred to fresh cuvettes and centrifuged again. The lysozyme concentrations of these supernatants were determined by measuring their UV absorption at 280 nm using a calibration curve. By subtracting the values used for the experiments from those in the supernatants, the amounts of lysozyme adsorbed by FSNP-39-COOH and FSNP-7-SH at different protein concentrations were determined.

FIGS. 74A and C show the absorption of buffer solutions of lysozyme at different concentrations before and after adsorption by fixed amounts of FSNP-39-COOH and FSNP-7-SH. The amounts of lysozyme adsorbed by the FSNPs are calculated by subtracting the amounts of protein used for the experiments from those of the supernatants by UV spectroscopy. With an increase in the protein concentration, the amount of lysozyme adsorbed by FSNP-39-COOH also becomes higher and reaches its maximum at 500 g/mL. Further increments of the concentration however, lead to no further adsorption. The amount of lysozyme adsorbed by FSNP-7-SH also increases with increasing protein concentration but quickly levels off at 200 μg/mL, further substantiating the previous discussion that FSNP-7-SH has a lower adsorption capacity than FSNP-39-COOH. A calibration curve of absorbance versus lysozyme concentration is established (FIG. 75) allowing quantitative determination of lysozyme adsorbed on FSNP-39-COOH and FSNP-7-SH from their absorbance. For 5 mg of FSNP-39-COOH and FSNP-7-SH, they can adsorb 209 and 86 μg of lysozyme, respectively. Thus, the functional FSNPs can be used as protein carriers or reactants for separating pure proteins from lysates.

Example 25

Lysozyme Adsorption at Different Nanoparticle Concentrations

The adsorption of a fixed amount of lysozyme by different concentrations of FSNP-39-COOH and FSNP-7-SH was investigated in buffer solutions (pH=10) at 25° C. In a typical experiment, 2 mL of lysozyme solution (400.0 μg/mL), 3 mL of buffer solution (pH=10), and 5, 10, 15, 20, and 25 mg of FSNP-39-COOH or FSNP-7-SH were added in small vials. The mixtures were incubated for 12 h and centrifuged. The supernatants were separated and their absorptions at 280 nm were determined. The amounts of lysozyme adsorbed by different concentrations of nanoparticles were calculated by subtracting the amounts of lysozyme used for the experiments from those in the supernatants.

The efficiency of lysozyme adsorption of FSNP-39-COOH and FSNP-7-SH was determined by dissolving fixed concentration of lysozyme (400 μg/mL) in solutions with varying amounts of FSNP-39-COOH and FSNP-7-SH. The amount of protein adsorbed on the nanoparticle surface is presented in FIG. 76. It is obvious that the protein adsorption process is strongly affected by the functional group present in the FSNPs. Almost all the lysozyme molecules are adsorbed by FSNP-39-COOH at a concentration of 25 mg/5 mL. On the contrary, less than half of the protein is adsorbed by FSNP-7-SH under the same conditions (FIG. 76B). If the electrostatic interactions between the protein and the nanoparticles govern the adsorption process, the higher uptake efficiency of FSNP-39-COOH than FSNP-7-SH suggests that the former nanoparticles possess a higher surface charge. The hydrophobic effect, however, does not play an important role as the surfaces of both FSNP-39-COOH and FSNP-7-SH are hydrophilic.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A fluorescent bioprobe for intracellular imaging comprising an aggregation induced emission luminogen and magnetite nanoparticles; wherein the luminogen has a backbone structure selected from the group consisting of:

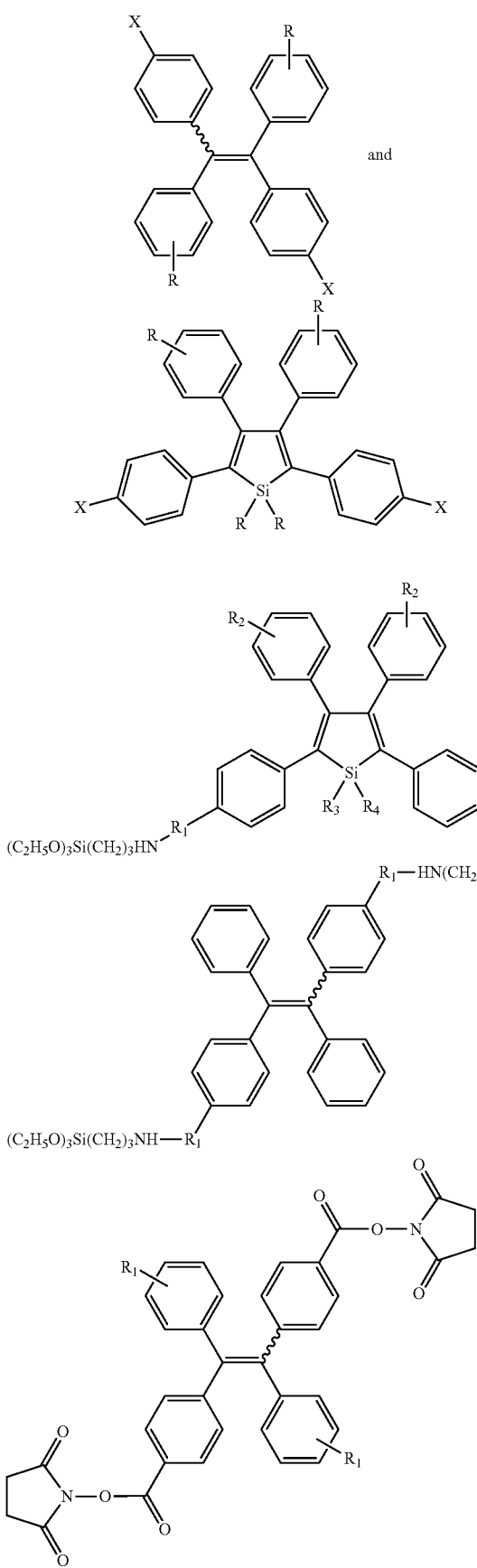

wherein

R is selected from the group consisting of H, alkyl, unsaturated alkyl, aryl, vinyl, acetyl, heteroalkyl, cycloalkyl, heterocycloalkyl, and heteroaryl;

X is selected from the group consisting of $(CH_2)_n$, $C_6H_5$, $(Ph)_n$, $O(CH_2)_n$, $NH(CH_2)_n$, $N[(CH_2)_n]_2$, $(OCH_2CH_2)_n$, $OCOR'C_2H$, COO-dioxopyrrolidine, $CONH(CH_2)_n$, $OR'NH(CH_2)_n$, $R'CH_2CH_2S(CH_2)_n$, $R'CHCHS(CH_2)_n$, $R'NH(CH_2)_n$, and R'-triazole-$(CH_2)_n$, wherein R' is independently selected from the group consisting of alkyl, unsaturated alkyl, aryl, vinyl, heteroalkyl, cycloalkyl, heterocycloalkyl, and heteroaryl; and n=0 to 20;

wherein X is capable of conjugating with a siloxane;

wherein the fluorescent bioprobe comprises magnetic fluorescent silica nanoparticles; and wherein the magnetic fluorescent silica nanoparticles are surface functionalized with one or more biomolecules selected from the group consisting of glucose, galactose, and folic acid.

2. The fluorescent bioprobe of claim 1, wherein the luminogen has a chemical structure selected from the group consisting of:

-continued
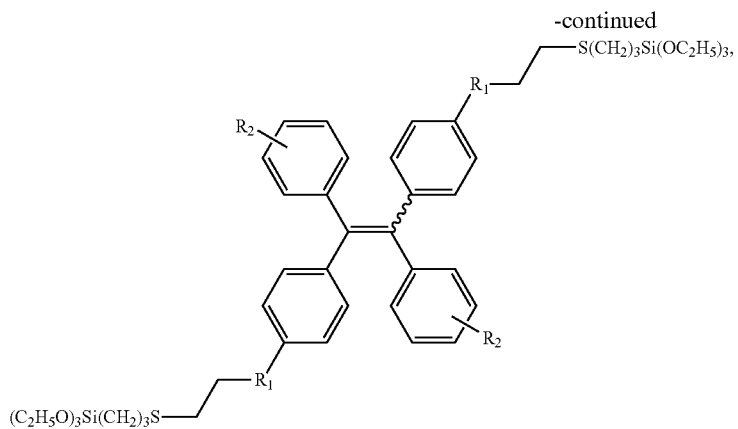
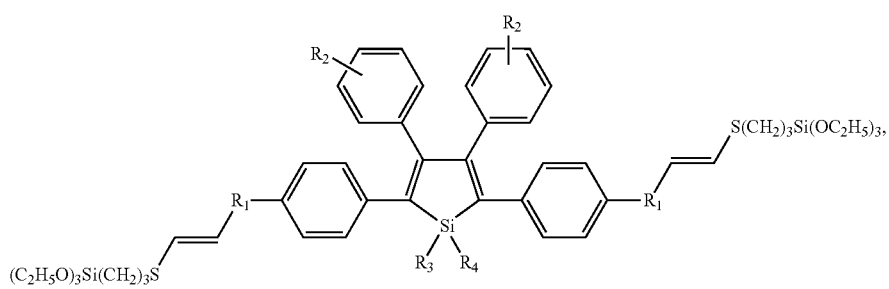
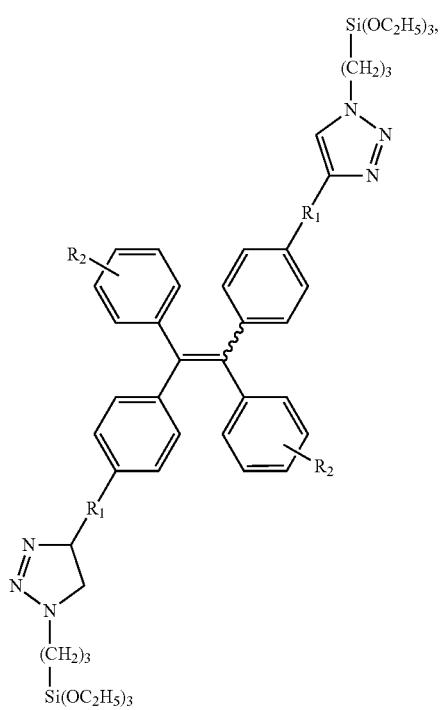
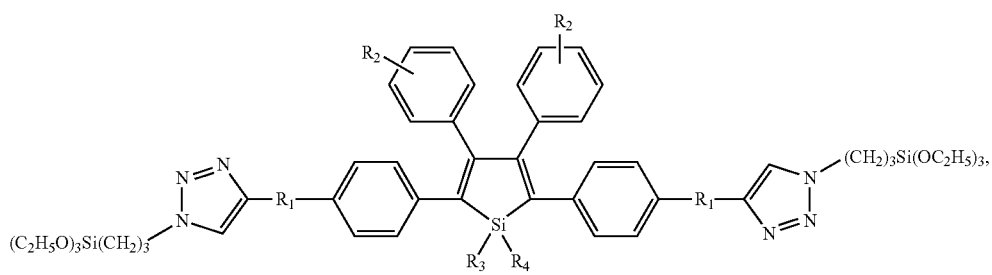

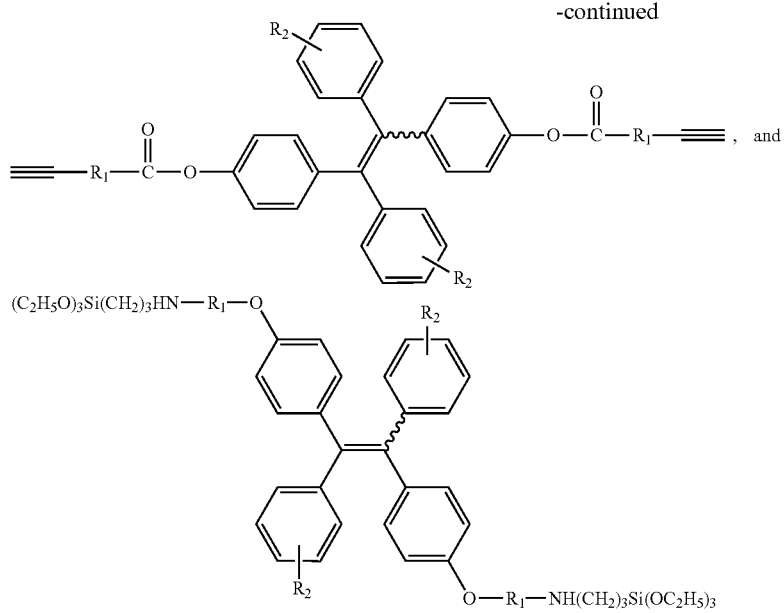

-continued wherein $R_1$ is a substituent selected from the group consisting of alkyl, unsaturated alkyl, aryl, vinyl, heteroalkyl, cycloalkyl, heterocycloalkyl, and heteroaryl, and wherein $R_2$, $R_3$, and $R_4$ are substituents independently selected from the group consisting of H, alkyl, unsaturated alkyl, aryl, vinyl, acetyl, heteroalkyl, cycloalkyl, heterocycloalkyl, and heteroaryl.

3. The fluorescent bioprobe of claim 1, wherein the magnetic fluorescent silica nanoparticles are also protein carriers.

4. The fluorescent bioprobe of claim 1, wherein the magnetic fluorescent silica nanoparticles exhibit aggregation-induced emission.

5. The fluorescent bioprobe of claim 1, wherein the magnetic fluorescent silica nanoparticles exhibit superparamagnetism.

6. The fluorescent bioprobe of claim 1, wherein the magnetic fluorescent silica nanoparticles exhibit negligible remanence and coercivity, wherein negligible remanence and coercivity indicate high magnetization.

7. The fluorescent bioprobe of claim 1, wherein the magnetic fluorescent silica nanoparticles emit light; and wherein the light emission increases with increased luminogen loading.

8. The fluorescent bioprobe of claim 1, wherein the aggregation induced emission luminogen is in solid form.

9. The fluorescent bioprobe of claim 1, wherein the magnetic fluorescent silica nanoparticles comprise magnetic cores covered by a silica shell.

10. The fluorescent bioprobe of claim 1, wherein the magnetic fluorescent silica nanoparticles are spherical with substantially uniform sizes and narrow particle distributions.

11. The fluorescent bioprobe of claim 1, wherein the magnetic fluorescent silica nanoparticles possess high surface charges, measured by zeta potential, and good colloidal stabilities, which result from high surface charges at a workable pH.

12. The fluorescent bioprobe of claim 1, wherein the aggregation induced emission luminogen is covalently bonded to a silica network through amine and amide functional groups.

13. The fluorescent bioprobe of claim 1, wherein the aggregation induced emission luminogen is covalently bonded to silica nanoparticles via alkyne-azide cycloaddition.

14. The fluorescent bioprobe of claim 1, wherein the aggregation induced emission luminogen is grafted onto the surface of silica nanoparticles.

15. The fluorescent bioprobe of claim 1, wherein the magnetic fluorescent silica nanoparticles are surface functionalized with one or more functional groups selected from the group consisting of amino, azido, carboxylic acid, and thiol functional groups.

16. The fluorescent bioprobe of claim 1, wherein the magnetic fluorescent silica nanoparticles are conjugated with the one or more biomolecules via an esterification reaction.

17. The fluorescent bioprobe of claim 1, wherein the magnetic fluorescent silica nanoparticles are nontoxic to living cells.

18. The fluorescent bioprobe of claim 1, wherein the magnetic fluorescent silica nanoparticles are effectively taken up by cancer cells.

19. The fluorescent bioprobe of claim 1, wherein the magnetic fluorescent silica nanoparticles can image cytoplasm of cancer cells.

20. The fluorescent bioprobe of claim 1, wherein the magnetic fluorescent silica nanoparticles can target specific cancer cells.

21. The fluorescent bioprobe of claim 1, wherein the magnetic fluorescent silica nanoparticles can adsorb protein molecules selected from the group consisting of bovine serum albumin (BSA) and lysozyme.

22. A process for preparing the bioprobe of claim 2 comprising a sol-gel reaction of silole-APS conjugate and tetraethoxysilane in a magnetic fluid of magnetite.

23. A process for preparing the bioprobe of claim 2 comprising a first sol-gel reaction of tetraphenylethene-containing siloxane, followed by a second sol-gel reaction with tetraethoxysilane.

24. A process for preparing the bioprobe of claim 1 comprising:
 (a) preparation of tetraphenylethene-containing siloxane and silole-containing siloxane;
 (b) sol-gel reactions of the tetraphenylethene-containing siloxane and the silole-containing siloxane; and
 (c) reactions of the tetraphenylethene-containing siloxane and silole-containing siloxane with tetraethoxysilane.

25. A process for preparing the bioprobe of claim 2 comprising:
(a) preparation of siloxane 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33);
(b) sol-gel reactions of siloxane 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33); and
(c) reactions of siloxane 1,2-Bis(4-{1-[2-(triethoxysilyl)ethyl]-4-triazolyl}phenyl)-1,2-diphenylethene (32) and 2,5-Bis(4-{1-[2-(triethoxysilyl)ethyl]-4-triazolyl}phenyl)-3,4-diphenyl-1,1-dimethylsilole (33) with tetraethoxysilane.

26. A process for preparing the bioprobe of claim 1 comprising surface grafting of the aggregation induced emission luminogen onto the magnetite nanoparticles.

27. A process for surface functionalization of the bioprobe of claim 1 comprising bioconjugation with glucose molecules using alkyne-azide cycloaddition.

28. A process for surface functionalization of the fluorescent bioprobe of claim 1 comprising a click reaction of sugar-bearing phenylacetylene with

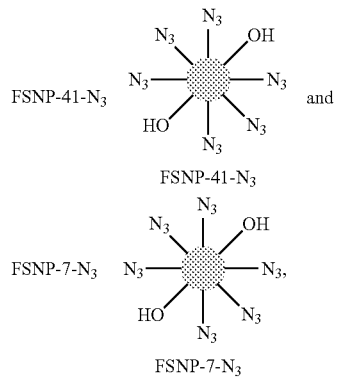

respectively.

29. A process for surface functionalization of the bioprobe of claim 1, comprising a reaction of folic acid with

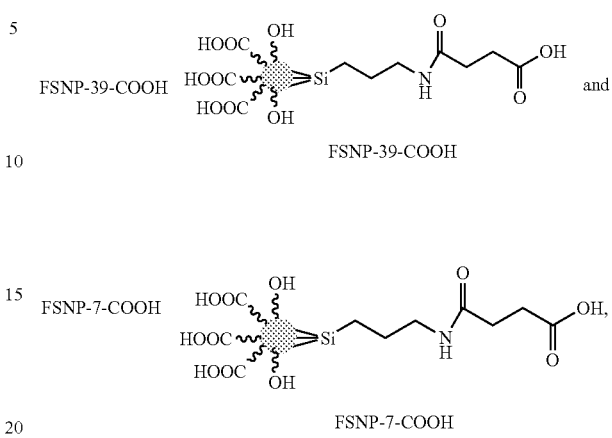

respectively.

30. A process for preparing lysozyme-decorated fluorescent silica nanoparticles comprising adsorption of lysozyme by

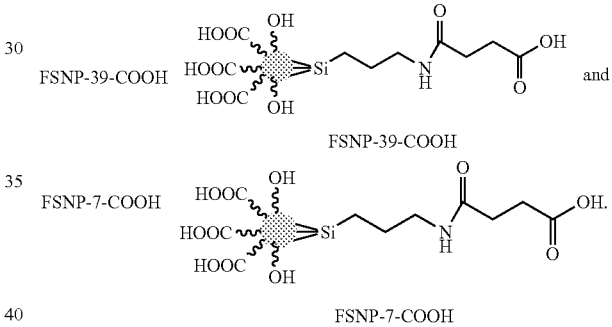

* * * * *